(12) United States Patent
Jo et al.

(10) Patent No.: US 8,450,279 B2
(45) Date of Patent: May 28, 2013

(54) CELL PERMEABLE NM23 RECOMBINANT PROTEINS, POLYNUCLEOTIDES ENCODING THE SAME, AND ANTI-METASTATIC COMPOSITION COMPRISING THE SAME

(75) Inventors: Daewoong Jo, Seoul (KR); Thi Thuy Nga Do, Jeollanam-do (KR); Kisuk Park, Seoul (KR)

(73) Assignee: Procell Therapeutics Inc., Seoul (KR)

( * ) Notice: Subject to any disclaimer, the term of this patent is extended or adjusted under 35 U.S.C. 154(b) by 513 days.

(21) Appl. No.: 12/676,182

(22) PCT Filed: Sep. 4, 2008

(86) PCT No.: PCT/KR2008/005221
§ 371 (c)(1),
(2), (4) Date: Mar. 3, 2010

(87) PCT Pub. No.: WO2009/031835
PCT Pub. Date: Mar. 12, 2009

(65) Prior Publication Data
US 2010/0323971 A1  Dec. 23, 2010

Related U.S. Application Data

(60) Provisional application No. 60/969,714, filed on Sep. 4, 2007.

(51) Int. Cl.
*C12N 15/12* (2006.01)
(52) U.S. Cl.
USPC .......... 514/19.8; 514/1.2; 514/21.6; 514/21.7
(58) Field of Classification Search
USPC ................................ 514/19.3, 19.8
See application file for complete search history.

(56) References Cited

FOREIGN PATENT DOCUMENTS

| CA | 2 336 223 | 8/2001 |
|---|---|---|
| EP | 1033405 A2 * | 9/2000 |
| EP | 1 127 576 A1 | 8/2001 |

(Continued)

OTHER PUBLICATIONS

Hiroshi Harada, et al., "Antitumor Protein Therapy; Application of the Protein Transduction Domain to the Development of a Protein Drug for Cancer Treatment", Breast Cancer, Japanese Breast Cancer Society, vol. 13, No. 1, XP-002544010, Jan. 1, 2006, pp. 16-26.

(Continued)

*Primary Examiner* — Christina Bradley
*Assistant Examiner* — Kristina M Hellman
(74) *Attorney, Agent, or Firm* — Oblon, Spivak, McClelland, Maier & Neustadt, L.L.P.

(57) ABSTRACT

The present invention discloses cell permeable Nm23 recombinant proteins where a macromolecule transduction domain (MTD) is fused to a metastasis suppressor Nm23. Also disclosed are polynucleotides encoding the cell permeable Nm23 recombinant proteins, an expression vector containing the cell permeable Nm23 recombinant protein, and a pharmaceutical composition for preventing metastasis which contains the cell permeable Nm23 recombinant protein as an effective ingredient. The cell permeable Nm23 recombinant proteins of the present invention can induce KSR phosphorylation and inactivation and inhibit Ras-mediated MAPK cascade by efficiently introducing a metastasis suppressor Nm23 into a cell. Therefore, the cell permeable Nm23 recombinant proteins of the present invention can be effectively used as an anti-metastatic agent capable of preventing cancer metastasis by inhibiting the proliferation, differentiation and migration of cancer cells.

21 Claims, 20 Drawing Sheets

FOREIGN PATENT DOCUMENTS

| | | |
|---|---|---|
| WO | WO 91/05793 A1 | 5/1991 |
| WO | WO 95/34295 A1 | 12/1995 |
| WO | WO 98/11232 A2 | 3/1998 |
| WO | WO 0175067 A2 * | 10/2001 |
| WO | WO 02/083179 A2 | 10/2002 |
| WO | WO 2008/093982 A1 | 8/2008 |

OTHER PUBLICATIONS

Alvaro Leone, et al., "Reduced Tumor Incidence, Metastatic Potential, and Cytokine Responsiveness of nm23-Transfected Melanoma Cells", Cell, Cell Press, vol. 65, No. 1, XP002326572, Apr. 5, 1991, pp. 25-35.

Extended European Search Report issued on Feb. 4, 2011 in the corresponding European Application No. 08829132.3.

Anna D'Angelo, et al., "Prune cAMP Phosphodiesterase Binds nm23-H1 and Promotes Cancer Metastasis", Cancer Cell, vol. 5, No. 2, Feb. 2004, pp. 137-149.

Daewoong Jo, et al., "Epigenetic Regulation of Gene Structure and Function with a Cell-Permeable Cre Recombinase", Nature Biotechnology, vol. 19, Oct. 2001, pp. 929-933.

Daewoong Jo, et al., "Intracellular Protein Therapy with SOCS3 Inhibits Inflammation and Apoptosis", Nature Medicine, vol. 11, No. 8, Aug. 2005, pp. 892-898.

Qing Lin, et al., "Enhanced Cell-Permeant Cre Protein for Site-Specific Recombination in Cultured Cells", BMC Biotechnology, Oct. 22, 2004, pp. 1-13.

Mike S. S. Chang, et al., "Dissecting Intracellular Signaling Pathways with Membrane-Permeable Peptides", Science STKE, vol. 47, pl1. [DOI: 10.1126/stke.2000.47.pl1], Aug. 29, 2000, pp. 1-10.

Nicholas J. MacDonald, et al., "A Serine Phosphorylation of Nm23, and Not Its Nucleoside Diphosphate Kinase Activity, Correlates with Suppression of Tumor Metastatic Potential", The Journal of Biological Chemistry, vol. 268, No. 34, Issue of Dec. 5, Received for Publication on May 20, 1993, pp. 25780-25789.

Patricia S. Steeg, "Breast Cancer Advocacy and Basic Research: A Scientist's Perspective", Breast Disease, 10(5,6), 1998, pp. 47-50.

Fabio Gervasi, et al., "nm23 Influences Proliferation and Differentiation of PC12 Cells in Response to Nerve Growth Factor", Cell Growth and Differentiation, vol. 7, Dec. 1996, pp. 1689-1695.

Renzo Hirayama, et al., "Positive Relationship Between Expression of Anti-metastatic Factor (nm23 Gene Product or Nucleoside Diphosphate Kinase) and Good Prognosis in Human Breast Cancer", Journal of the National Cancer Institute, Brief Communications, vol. 83, No. 17, Sep. 4, 1991, pp. 1249-1253.

Toshihiro Nakayama, et al., "Expression in Human Hepatocellular Carcinoma of Nucleoside Diphosphate Kinase, a Homologue of the nm23 Gene Product", Journal of the National Cancer Institute, Reports, vol. 84. No. 17, Sep. 2, 1992, pp. 1349-1354.

Alvaro Leone, et al., "Transfection of Human nm23-H1 into the Human MDA-MB-435 Breast Carcinoma Cell Line: Effects on Tumor Metastatic Potential, Colonization and Enzymatic Activity", Oncogene, 8, 1993, pp. 2325-2333.

Alvaro Leone, et al., "Reduced Tumor Incidence, Metastatic Potential, and Cytokine Responsiveness of nm23-Transfected Melanoma Cells", Cell, vol. 65, Apr. 5, 1991, pp. 25-35.

Alvaro Leone, et al., "Evidence for nm23 RNA Overexpression, DNA Amplification and Mutation in Aggressive Childhood Neuroblastomas", Oncogene, 8, 1993, pp. 855-865.

Nicholas J. MacDonald, et al., "Site-directed Mutagenesis of nm23-H1", vol. 271, No. 41, Issue of Oct. 11, The Journal of Biological Chemistry, Received for Publication on Mar. 11, 1996, pp. 25107-25116.

Deborah K. Morrison, et al., "KSR: a MAPK Scaffold of the Ras Pathway?", Journal of Cell Science, 114 (9), 2001, pp. 1609-1612.

W Richard Burack, et al., "Signal Transduction: Hanging on a Scaffold", Current Opinion in Cell Biology, 12, 2000, pp. 211-216.

Tony Pawson, et al., "Signaling Through Scaffold, Anchoring, and Adaptor Proteins", American Association for the Advancement of Science, Science, New Series, vol. 278, No. 5346, Dec. 19, 1997, pp. 2075-2080.

Toru Yoshida, et al., "Microsatellite Instability in Gallbladder Carcinoma: Two Independent Genetic Pathways of Gallbladder Carcinogenesis", Journal of Gastroenterology, 35, 2000, pp. 768-774.

Melanie T. Hartsough, et al., "Nm23-H1 Metastasis Suppressor Phosphorylation of Kinase Suppressor of Ras via a Histidine Protein Kinase Pathway", The Journal of Biological Chemistry, vol. 277, No. 35, Issue of Aug. 30, Received for Publication on Apr. 1, 2002, pp. 32389-32399.

* cited by examiner

M: Marker
1: HN       −513bp
2: $HM_1N$   −549bp
3: $HNM_1$   −549bp
4: $HM_1NM_1$ −585bp 1: $HM_2N$     −537bp
2: $HNM_2$     −537bp
3: $HM_2NM_2$ −561bp
4: $HM_3N$     −540bp
5: $HNM_3$     −540bp
6: $HM_3NM_3$ −567bp M: Marker
1: HN        −513bp
2: HM₁N      −549bp
3: HNM₁      −549bp
4: HM₁NM₁    −585bp M: Marker
1: HM₂N      −537bp
2: HNM₂      −537bp
3: HM₂NM₂    −561bp
4: HM₃N      −540bp
5: HNM₃      −540bp
6: HM₃NM₃    −567bp M: Marker
1: HN      −513bp
2: HM$_1$N    −549bp
3: HNM$_1$    −549bp
4: HM$_1$NM$_1$  −585bp M: Marker
1: HM$_2$N     −537bp
2: HNM$_2$     −537bp
3: HM$_2$NM$_2$  −561bp
4: HM$_3$N     −540bp
5: HNM$_3$     −540bp
6: HM$_3$NM$_3$  −567bp

Fig. 10b

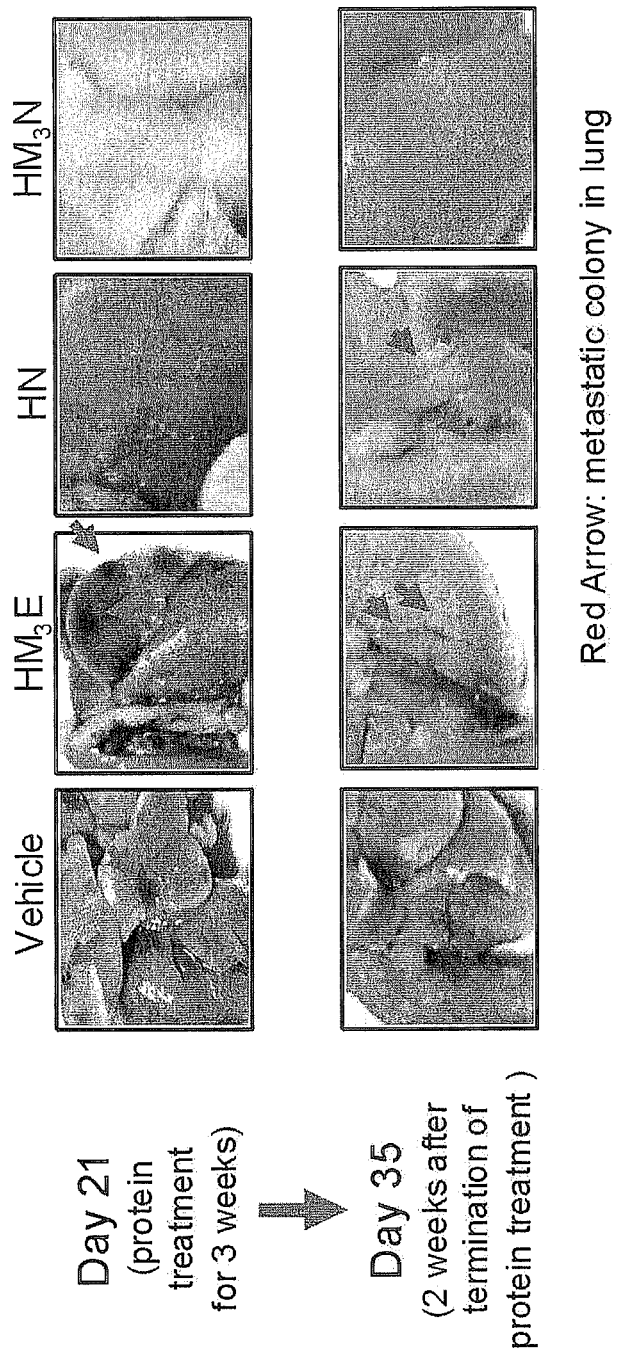

# CELL PERMEABLE NM23 RECOMBINANT PROTEINS, POLYNUCLEOTIDES ENCODING THE SAME, AND ANTI-METASTATIC COMPOSITION COMPRISING THE SAME

CROSS-REFERENCE TO RELATED APPLICATIONS

This application is a National Stage of PCT/KR08/005221 filed Sep. 4, 2008 and claims the benefit of U.S. 60/969,714 filed Sep. 4, 2007.

TECHNICAL FIELD

The present invention relates to cell permeable Nm23 recombinant proteins in which a metastasis suppressor Nm23 is fused to a macromolecule transduction domain (MTD), polynucleotides encoding the same, expression vectors for producing the same, and anti-metastatic pharmaceutical compositions including the same as effective ingredients for inhibiting metastasis.

BACKGROUND ART

Nm23 gene has been reported to encode proteins involved in the development and differentiation of a normal tissue, and its expression is decreased in various metastatic cells. Nm23 proteins belong to a tumor metastasis suppressor and generally consist of 150 to 180 amino acids. Nm23 proteins contain a leucine zipper motif and exhibit nucleoside diphosphate kinase (NDPK) activity. Two human Nm23 homologues, Nm23-H1 and Nm23-H2, consist of 152 amino acids having molecular weights of 17,143 and 17,294, respectively. In particular, it has been found that Nm23-H1 plays an important role in tumor metastasis and other various cell mechanisms including cell proliferation, embryogenesis, differentiation and tumorigenesis.

The mechanisms by which Nm23 affects tumor development and metastasis have not yet been clearly investigated. NDPK transfers a phosphoryl group between nucleoside triphosphate and nucleoside diphosphate via a covalent phosphoenzyme intermediate. For such a phosphorylation, histidine 118 of each Nm23-H1 and Nm23-H2 is served as a target site. Apart from the NDPK-mediated histidine phosphorylation, serine autophosphorylation was observed in Nm23 (MacDonald N J et al., *J. Biol. Chem.* 268: 25780-25789, 1993). When melanoma cells of Nm23 transfected mice were compared with a control cell, there was a direct correlation between the in vivo phosphorylation level of Nm23 serine and the inhibition of tumor metastatic potential. Serine phosphorylation of mouse Nm23 is inhibited by cAMP in vivo, while by forskolin in vitro, which demonstrates that the phosphorylation is controlled by signal transduction pathways.

Initially, Nm23 expression was reported to closely correlate to mouse melanoma cell lines with poor metastatic potential. The relationship between Nm23 reduced expression and tumor metastasis has been regarded as direct evidence to support the fact that Nm23 functions as a tumor metastasis suppressor (Steeg, P. S., *Breast Dis.* 10: 47-50, 1998). Inducible overexpression of Nm23 exhibited remarkably reduced metastatic potential in a highly metastatic cancer cell line. The Nm23 gene cloned as a putative tumor metastasis suppressor gene exhibits serine/threonine specific phosphotransferase and histidine protein kinase activities, as well as NDPK activity. Further, the expression of Nm23 is reduced as hematopoietic stem cells (HSC) are differentiated, which suggests that Nm23 is an important factor for anti-differentiation in those cells (Gervasi, F. et al., *Cell Growth Differ* 7: 1689-95, 1996). It has been found that Nm23 exhibits a strong inhibitory effect on tumor metastasis upon temporary transfection in forced inducible gene expression and in vitro metastasis model systems of human tumors (Hirayama, R. et al., *J. Natl. Cancer Inst.* 83: 1249-50, 1991; Nakayama, T. et al., *J. Natl. Cancer Inst.* 84: 1349-54, 1992; Leone, A. et al., Oncogene 8: 2325-33, 1993; Leone, A. et al., *Oncogene* 8: 855-65, 1993). In contrast, Nm23 mutation, leading to the loss of NDPK activity, had no influence on the inhibitory function of Nm23 in breast cancer cells (MacDonald, N. J. et al., *J. Biol. Chem.* 271:25107-16, 1996).

The most authentic evidence for the fact that Nm23 is a metastasis suppressor is revealed when the Nm23 gene is transfected into tumor cell lines. In metastatically competent cells, the administration of high dose Nm23 showed reduced metastatic activity by 40 to 98% as compared with a control transfectant (Leone, A. et al, *Cell* 65: 25-35, 1991; Leone, A. et al., *Oncogene* 8:2325-33, 1993).

Recently, it has been reported that Nm23 interacts with a kinase suppressor of Ras (KSR) discovered in the Drosophilae (*Drosophilar melanogaster*) and nematode (*Caenorhabditis elegans*) systems (Morrison, D. K., *J. Cell Sci.* 114: 1609-12, 2001). KSR is a scaffold protein of a mitogen-activated protein kinase (MAPK) cascade (Burack, W. R. and Shaw, A. S., *Curr. Opin. Cell Biol.* 12: 211-6, 2000; Pawson, T. and Scott, J. D., *Science* 278: 2075-80, 1997). Such scaffold protein is necessary to enhance the rate of phosphorylation and contribute to the specificity and stabilization of the phosphorylation pathway. Once the MAPK signal transduction pathway is activated by active Ras, KSR is forcedly dephosphorylated, and then, serve as a scaffold for the activation of MAPK cascade. During this process, Nm23 phosphorylates KSR serine 392, which is a binding site for another associated protein of KSR. If the serine 392 is mutated, Nm23 phosphorylates KSR serine 434. The metastatic inhibitory activity of Nm23 has been clearly demonstrated by the fact that metastatic potential is inhibited in various tumor cells transfected with Nm23 gene (Yoshida, T. et al., *J Gastroenterol.* 35: 768-74, 2000). In cells activated by the stimulation of the MAPK cascade, the interaction between Nm23 and KSR induces KSR phosphorylation in vitro in a complicated manner via a histidine-dependent pathway (Hartsough, M. T. et al., *J. Biol. Chem.* 277: 32389-99, 2002). Further, the in vivo association of KSR and Nm23 inhibits the phenotypic effect of active Ras which activates the MAPK cascade.

Accordingly, the administration of high dose Nm23 protein may phosphorylate and inactivate KSR in vivo, leading to the inhibition of Ras-mediated MAPK cascade. The present inventors have therefore believed that the inhibition of MAPK signal transduction pathway mediated by re-phosphorylation of KSR may inhibit cell proliferation, differentiation and migration of cancer cells and exhibit anti-metastatic effect in various human cancers, and endeavored to develop new anti-metastatic agents by using the Nm23 protein.

Meanwhile, small molecules derived from synthetic compounds or natural compounds can be transported into the cells, whereas macromolecules, such as proteins, peptides, and nucleic acids, cannot. It is widely understood that macromolecules larger than 500 kDa are incapable of penetrating the plasma membrane, i.e., the lipid bilayer structure, of live cells. To overcome this problem, a macromolecule intracellular transduction technology (MITT) was developed (Jo et al., *Nat. Biotech.* 19: 929-33, 2001), which allows the delivery of therapeutically effective macromolecules into cells, making the development of new drugs using peptides, proteins and genetic materials possible. According to this method, if a target macromolecule is fused to a hydrophobic macromolecule transduction domain (MTD) and other cellular delivery regulators, synthesized, expressed, and purified in the form of a recombinant protein, it can penetrate the plasma membrane lipid bilayer of the cells, be accurately delivered to a target site, and then, effectively exhibit its therapeutic effect. Such MTDs facilitate the transport of many impermeable materials which are fused to peptides, proteins, DNA, RNA, synthetic compounds, and the like into the cells.

Accordingly, the inventors of the present invention have developed a method of mediating the transport of a metastasis suppressor Nm23 into the cells, where cell permeable Nm23 recombinant proteins are engineered by fusing a MTD to the metastasis suppressor Nm23. Such cell permeable Nm23 recombinant proteins have been found to efficiently mediate the transport of a metastasis suppressor Nm23 into the cells in vivo as well as in vitro and can be used as anti-metastatic agents for inhibiting metastasis occurring in various human cancers.

DISCLOSURE

Technical Problem

Accordingly, the objective of the present invention is to provide cell permeable Nm23 recombinant proteins as an anti-metastatic agent which is effective for preventing metastasis in various kinds of human cancers by inhibiting proliferation, differentiation and migration of cancer cells.

Technical Solution

One aspect of the present invention relates to cell permeable Nm23 recombinant proteins capable of mediating the transport of a metastasis suppressor Nm23 into a cell by fusing a macromolecule transduction domain (MTD) having cell permeability to the metastasis suppressor protein.

Another aspect of the present invention relates to polynucleotides encoding the above cell permeable Nm23 recombinant proteins.

The present invention also relates to expression vectors containing the above polynucleotides, and transformants transformed with the above expression vectors.

Another aspect of the present invention relates to a method of producing cell permeable Nm23 recombinant proteins involving culturing the above transformants.

Another aspect of the present invention relates to a pharmaceutical composition including the above cell permeable Nm23 recombinant proteins as an effective ingredient for inhibiting metastasis.

DESCRIPTION OF DRAWINGS

FIGS. 10a and 10b are photographs of an invasion analysis showing the inhibitory effect of cell permeable Nm23 recombinant proteins according to the present invention on metastasis.

FIG. 12a is a photograph illustrating the inhibitory effect on metastasis in a mouse lung tissue extracted from a mouse administered with the cell permeable Nm23 recombinant protein according to the present invention.

BEST MODE FOR CARRYING OUT THE INVENTION

Figure 1:
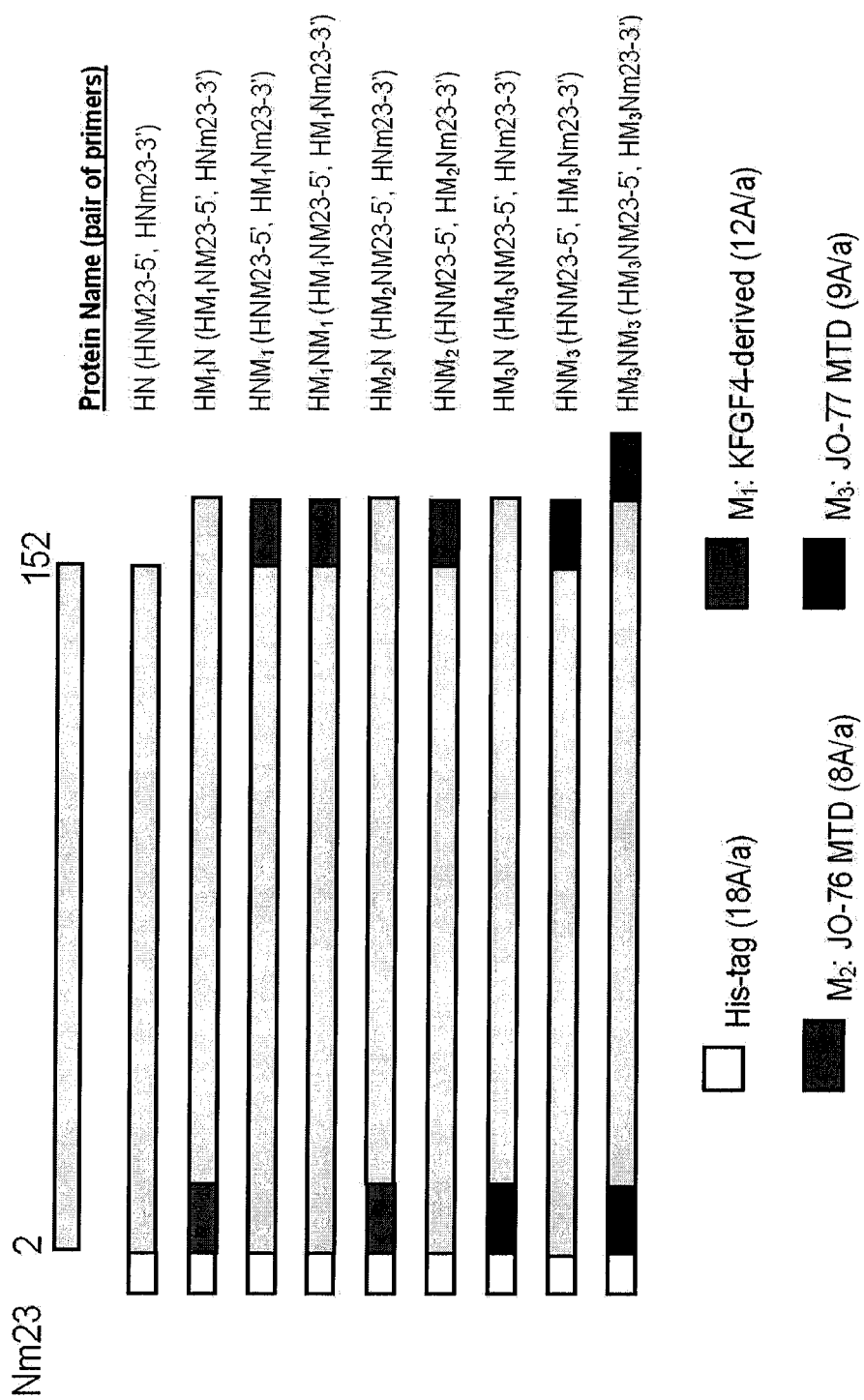
FIG. 1 is a schematic diagram illustrating the structures of cell permeable Nm23 recombinant proteins being fused to one of a kFGF4-derived MTD, JO-76 MTD and JO-77 MTD and constructed in the full-length forms according to the present invention.

The present invention provides cell permeable Nm23 recombinant proteins (CP-Nm23) capable of mediating the transport of a metastasis suppressor Nm23 into a cell in which the metastasis suppressor Nm23 is fused to a macromolecule transduction domain and, thereby, imparted with cell permeability; and polynucleotides encoding each of the cell permeable Nm23 recombinant proteins.

The present invention is characterized in that a metastasis suppressor Nm23 which is a macromolecule incapable of being introduced into a cell is fused to a specific macromolecule transduction domain (hereinafter, "MTD") peptide so as to provide cell permeability, and thus, can be effectively transported into a cell. The MTD peptide may be fused to the N-terminus, the C-terminus, or both termini of the metastasis suppressor Nm23.

The present invention relates to cell permeable Nm23 recombinant proteins that are engineered by fusing a metastasis suppressor Nm23 to one of three MTD domains capable of mediating the transport of a macromolecule into a cell.

The term "cell permeable Nm23 recombinant protein" as used herein refers to a covalent bond complex bearing a MTD and a metastasis suppressor protein Nm23, where they are functionally linked by genetic fusion or chemical coupling. Here, the term "genetic fusion" refers to a co-linear, covalent linkage of two or more proteins or fragments thereof via their individual peptide backbones, through genetic expression of a polynucleotide molecule encoding those proteins.

Nm23 is a metastasis suppressor protein which inhibits the proliferation, differentiation and migration of cancer cells and induces apoptosis by controlling the MAPK signal transduction cascade which is mediated by KSR phosphorylation. Nm23 has an amino acid sequence represented by SEQ ID NO: 2, while a polynucleotide encoding the same has a nucleotide sequence represented by SEQ ID NO: 1. Nm23 functions as an important target protein in signal transduction cascades including KSR and Ras-mediated MAPK.

It has been reported that Nm23 is an endogeneous protein and exhibits NDP (nucleotide diphosphate)-kinase enzyme activity (Biggs et al., *Cell* 63, 933-940, 1990). Nm23 has also been found to be a transcription factor and cell differentiation inhibitor (I factor) (Postel et al., *Science* 261, 478-480, 1993; Okabe-Kado et al., *Biochim. Biophys. Acta.* 1267, 101-106, 1995).

In humans, eight nm23 isotypes (nm23-H1, nm23-H2, DR-nm23, nm23-H4, nm23-H5, nm23-H6, nm23-H7, and nm23-H8) have been identified to date, all of which are implicated in the regulation of metastasis (Rosengard et al., *Nature* 342, 177-180, 1989; Charpin C. et al., *Int. J. Cancer* 74, 416-420, 1997). In certain embodiments, cell permeable recombinant proteins for Nm23-H1 have been constructed, but are not limited thereto.

For the MTD capable of being fused to the metastasis suppressor Nm23, cell permeable peptides having an amino acid sequence selected from the group consisting of SEQ ID NOS: 4, 6, 8, and 37 to 227 may be used. The MTD having one of the amino acid sequences represented by SEQ ID NOS: 4, 6, 8 and 37 to 227 is a cell permeable polypeptide which is capable of mediating the transport of a biologically active molecule, such as a polypeptide, a protein domain, or a full-length protein across the cell membrane. Suitable MTDs for the present invention include a hydrophobic region showing cell membrane targeting activity by forming a helix structure at a signal peptide which is composed of an N-terminal domain, a hydrophobic domain and a C-terminal domain containing a secreted protein cleavage site. These MTDs can directly penetrate the cell membrane without causing any cell damage, transport a target protein into a cell, and thus, allow the target protein to exhibit its desired function.

The MTDs having the amino acid sequences represented by SEQ ID NOS: 4, 6, 8, and 37 to 227 and capable of being fused to a metastasis suppressor Nm23 according to the present invention are summarized in the following Tables 1a to 11.

TABLE 1a

| MTD Origin | Amino acid sequence | SEQ ID NO |
|---|---|---|
| JO-01CAC04038 putative NLP/P60-family secreted protein [*Streptomyces coelicolor* A3(2)] | Ala Val Val Val Cys Ala Ile Val Leu Ala Ala Pro | 37 |
| JO-02NP_057021 phosphatidylinositol glycan, class T precursor [*Homo sapiens*] | Pro Leu Ala Leu Leu Val Leu Leu Leu Leu Gly Pro | 38 |
| JO-03NP_072171 chorionic somatomammotropin hormone 2 isoform 3 [*Homo sapiens*] | Leu Leu Leu Ala Phe Ala Leu Leu Cys Leu Pro | 39 |
| JO-04NP_932156 nudix-type motif 9 isoform a [*Homo sapiens*] | Leu Leu Gly Ala Leu Ala Ala Val Leu Leu Ala Leu Ala | 40 |
| JO-05NP_057327 NAD(P)H: quinone oxidoreductase type 3, polypeptide A2 [*Homo sapiens*] | Pro Val Leu Leu Ala Leu Gly Val Gly Leu Val Leu Leu Gly Leu Ala Val | 41 |
| JO-06CAD55300 putative secreted protein. [*Streptomyces coelicolor* A3(2)] | Ala Ala Ala Ala Val Leu Leu Ala Ala | 42 |
| JO-07NP_629514 secreted protein [*Streptomyces coelicolor* A3(2)] | Ile Val Val Ala Val Val Val Ile | 43 |

TABLE 1a-continued

| MTD Origin | Amino acid sequence | SEQ ID NO |
|---|---|---|
| JO-08CAB57190 putative secreted chitin binding protein [*Streptomyces coelicolor* A3(2)] | Ala Val Leu Ala Pro Val Val Ala Val | 44 |
| JO-09CAB51015 putative secreted protein [*Streptomyces coelicolor* A3(2)] | Leu Ala Val Cys Gly Leu Pro Val Val Ala Leu Leu Ala | 45 |
| JO-10NP_625021 glycosyl hydrolase (secreted protein) [*Streptomyces coelicolor* A3(2)] | Leu Gly Gly Ala Val Val Ala Ala Pro Val Ala Ala Ala Val Ala Pro | 46 |
| JO-11NP_630686 secreted protein [*Streptomyces coelicolor* A3(2)] | Leu Leu Leu Val Leu Ala Val Leu Leu Ala Val Leu Pro | 47 |
| JO-12NP_057329 dehydrogenase/reductase (SDR family) member 8 [*Homo sapiens*] | Leu Leu Ile Leu Leu Leu Leu Pro Leu Leu Ile Val | 48 |
| JO-13NP_639877 putative secreted protein [*Streptomyces coelicolor* A3(2)] | Leu Ala Ala Ala Ala Leu Ala Val Leu Pro Leu | 49 |
| JO-14NP_699201 protease inhibitor 16 precursor [*Homo sapiens*] | Phe Leu Met Leu Leu Leu Pro Leu Leu Leu Leu Val Ala | 50 |
| JO-15NP_639871 putative secreted protein [*Streptomyces coelicolor* A3(2)] | Ala Ala Ala Ala Ala Ala Leu Gly Leu Ala Ala Ala Val Pro Ala | 51 |
| JO-16CAB85250 putative secreted protein [*Neisseria meningitidis* Z2491] | Leu Leu Leu Ala Ala Leu Leu Leu Ile Ala Phe Ala Ala Val | 52 |

TABLE 1b

| MTD Origin | Amino acid sequence | SEQ ID NO |
|---|---|---|
| JO-17NP_626397 small secreted hydrophilic protein [*Streptomyces coelicolor* A3(2)] | Ala Leu Ala Ala Val Val Leu Ile Pro Leu Gly Ile Ala Ala | 53 |
| JO-18CAB38593 putative secreted protein [*Streptomyces coelicolor* A3(2)] | Ala Ala Leu Ala Leu Gly Val Ala Ala Ala Pro Ala Ala Ala Pro Ala | 54 |
| JO-19CAB57190 putative secreted chitin binding protein [*Streptomyces coelicolor* A3(2)] | Ala Ala Leu Ile Gly Ala Val Leu Ala Pro Val Val Ala Val | 55 |
| JO-20NP_626007 secreted cellulose-binding protein [*Streptomyces coelicolor* A3(2)] | Ala Ala Gly Ile Ala Val Ala Ile Ala Ala Ile Val Pro Leu Ala | 56 |
| JO-21NP_625632 secreted protein [*Streptomyces coelicolor* A3(2)] | Ile Ala Val Ala Ile Ala Ala Ile Val Pro Leu Ala | 57 |
| JO-22CAC31790 putative secreted protein [*Mycobacterium leprae*] | Val Ala Met Ala Ala Ala Ala Val Leu Ala Ala Pro Ala Leu Ala | 58 |
| JO-23NP_630266 secreted Protein [*StrePtomyces coelicolor* A3(2)] | Leu Ala Val Leu Val Leu Leu Val Leu Leu Pro | 59 |
| JO-24NP_630165 secreted Protein [*StrePtomyces coelicolor* A3(2)] | Val Val Ala Val Leu Ala Pro Val Leu | 60 |
| JO-25NC_003888 secreted Protein [*StrePtomyces coelicolor* A3(2)] | Ala Ala Leu Leu Leu Pro Leu Leu Leu Leu Leu Pro | 61 |
| JO-26NP_627363 secreted Protein [*StrePtomyces coelicolor* A3(2)] | Pro Ala Ala Val Ala Ala Leu Leu Val Ile | 62 |
| JO-27NP_631288 secreted Protein [*StrePtomyces coelicolor* A3(2)] | Leu Leu Ile Ala Ala Leu Leu Pro | 63 |
| JO-28NP_630325 secreted Protein [*StrePtomyces coelicolor* A3(2)] | Ala Ala Val Val Leu Leu Pro Leu Ala Ala Ala Pro | 64 |
| JO-29NP_631289 secreted Protein [*StrePtomyces coelicolor* A3(2)] | Ala Ala Ala Ala Ala Ala Leu Leu Val Pro | 65 |
| JO-30CAB51015 Putative secreted Protein [*StrePtomyces coelicolor* A3(2)] | Leu Pro Val Val Ala Leu Leu Ala | 66 |

TABLE 1b-continued

| MTD | Origin | Amino acid sequence | SEQ ID NO |
|---|---|---|---|
| JO-31 | NP_629515 chitinase C (secreted Protein) [StrePtomyces coelicolor A3(2)] | Ala Ala Ala Leu Ala Ala Pro Leu Ala Leu Pro | 67 |
| JO-32 | NP_940995 C1q and tumor necrosis factor related Protein 1 isoform 1 [Homo saPiens] | Leu Leu Leu Ala Leu Leu Leu Ala Ala | 68 |
| JO-33 | NP_854150 POSSIBLE CONSERVED SECRETED PROTEIN [Mycobacterium bovis AF2122/97] | Ala Val Ala Val Val Ala Leu Leu | 69 |

TABLE 1c

| MTD | Origin | Amino acid sequence | SEQ ID NO |
|---|---|---|---|
| JO-34 | NP_630361 Probable secreted Protein [StrePtomyces coelicolor A3(2)] | Leu Leu Leu Ile Ile Val Leu Leu Ile Val Pro | 70 |
| JO-35 | P39790 Extracellular metalloProtease Precursor | Leu Ala Leu Ala Ala Ala Val Val Pro | 71 |
| JO-36 | CAA19252 Putative liPoProtein [StrePtomyces coelicolor A3(2)] | Pro Ala Ala Leu Ala Leu Leu Leu Val Ala | 72 |
| JO-37 | P_625685 large secreted Protein [StrePtomyces coelicolor A3(2)] | Ile Val Ala Leu Leu Leu Val Pro Leu Val Leu Ala Ile Ala Ala Val Leu | 73 |
| JO-38 | NP_625685 large secreted Protein [StrePtomyces coelicolor A3(2)] | Ile Val Ala Leu Leu Leu Val Pro | 74 |
| JO-39 | NP_625685 large secreted Protein [StrePtomyces coelicolor A3(2)] | Pro Leu Val Leu Ala Ile Ala Ala Val Leu | 75 |
| JO-40 | NP_808800 golgi PhosPhoProtein 2 [Homo sapiens] | Pro Leu Val Leu Ala Ala Leu Val Ala | 76 |
| JO-41 | NP_626993 selected Protein [StrePtomyces coelicolor A3(2)] | Ala Ala Ala Leu Leu Ala Val Ala | 77 |
| JO-42 | NP_004863 thymic dendritic cell-derived factor 1 [Homo saPiens] | Pro Leu Leu Leu Leu Ala Leu Ala | 78 |
| JO-43 | NP_631398 secreted Protein [StrePtomyces coelicolor A3(2)] | Ala Leu Ala Leu Val Val Ala | 79 |
| JO-44 | NP_627373 Penicillin-binding Protein (secreted Protein) [StrePtomyces coelicolor A3(2)] | Val Ala Ala Val Val Val Ala Ala | 80 |
| JO-45 | NP_056226 sulfatase modifying factor 2 [Homo sapiens] | Pro Leu Leu Pro Leu Leu Leu Leu Val | 81 |
| JO-46 | NP_854998 Conserved hypothelial secreted protein [Mycobacterium bovis AF2122/97] | Val Val Leu Val Val Val Leu Pro Leu Ala Val Leu Ala | 82 |
| JO-47 | NP_627512 secreted Protein [StrePtomyces coelicolor A3(2)] | Ala Ala Ala Val Pro Val Leu Val Ala Ala | 83 |
| JO-48 | NP_110448 phospholipase A2, group XIIA [Homo sapiens] | Pro Ala Leu Leu Leu Leu Leu Leu Ala Ala Val Val | 84 |
| JO-49 | NP_003245 tissue inhibitor of metallo-proteinase 1 precursor [Homo sapiens] | Pro-Leu Ala Ile Leu Leu Leu Leu Leu Ile Ala Pro | 85 |
| JO-50 | NP_002978 small inducible cytokine A17 precursor [Homo sapiens] | Pro Leu Leu Ala Leu Val Leu Leu Leu Ala Leu Ile Ala | 86 |
| JO-51 | NP_001012495 stromal cell derived factor 1 isoform gamma precursor [Mus musculus] | Val Val Ala Val Leu Ala Leu Val Leu Ala Ala Leu | 87 |

TABLE 1d

| MTD Origin | Amino acid sequence | SEQ ID NO |
|---|---|---|
| JO-52NP 775628 ficolin 3 isoform 2 precursor [*Homo sapiens*] | Pro Leu Leu Leu Leu Leu Pro Ala Leu | 88 |
| JO-53NP 624483 secreted protein [*Streptomyces coelicolor* A3(2)] | Leu Ala Ala Val Ala Ala Leu Ala Val Val Val Pro | 89 |
| JO-54NP_997465 HERV-FRD provirus ancestral Env polyprotein [*Homo sapiens*] | Leu Leu Leu Leu Val Leu Ile Leu Pro Leu Ala Ala | 90 |
| JO-55NP_854234 posible conserved secreted protein [*Mycobacterium bovis* AF2122/97] | Leu Ala Val Val Val Val Ala Ala Val | 91 |
| JO-56P23284 Peptidyl-prolyl cis-trans isomerase B precursor (PPIase) (Rotamase) (Cyclophilin B) | Val Leu Leu Ala Ala Ala Leu Ile Ala | 92 |
| JO-57CAD05047 hypothetical secreted protein [*Salmonella enterica* subsp. *Enterica serovar* Typhi] | Leu Ile Ala Leu Leu Ala Ala Pro Leu Ala | 93 |
| JO-58P05067 Amyloid beta A4 protein precursor (APP) (ABPP) (Alzheimer disease amyloid protein) | Leu Ala Leu Leu Leu Leu Ala Ala | 94 |
| JO-59NP_004878 small inducible cytokine B14 precursor [*Homo sapiens*] | Leu Leu Ala Ala Ala Leu Leu Leu Leu Leu Leu Ala | 95 |
| JO-60NP_626589 secreted protein [*Streptomyces coelicolor* A3(2)] | Val Ile Ile Ala Leu Ile Val Ile Val Ala | 96 |
| JO-61NP_626589 secreted protein [*Streptomyces coelicolor* A3(2)] | Val Val Leu Val Val Ala Ala Val Leu Ala Leu | 97 |
| JO-62NP_856548 SOLUBLE SECRETED ANTIGEN MPB53 [*Mycobacterium bovis* AF2122/97] | Val Ala Val Ala Ile Ala Val Val Leu | 98 |
| JO-63NP_629854 secreted protein [*Streptomyces coelicolor* A3(2)] | Pro Leu Ile Val Val Ala Ala Ala Val Val Ala Val | 99 |
| JO-64AAB59058 lambda receptor protein [*Escherichia coli*] | Pro Leu Ala Val Ala Val Ala Ala Val Ala Ala | 100 |
| JO-65NP_825185 NLP/P60-family secreted protein [*Streptomyces avermitilis* MA-4680] | Ala Ala Ile Ala Leu Val Ala Val Val Leu | 101 |
| JO-66NP_626568 secreted protein [*Streptomyces coelicolor* A3(2)] | Ala Ala Ala Leu Ala Ala Ile Ala Val Ile | 102 |
| JO-67NP_626568 secreted protein [*Streptomyces coelicolor* A3(2)] | Ala Ala Ala Pro Ala Val Ala Ala | 103 |

TABLE 1e

| MTD Origin | Amino acid sequence | SEQ ID NO |
|---|---|---|
| JO-68NP_625639 secreted protein [*Streptomyces coelicolor* A3(2)] | Leu Leu Leu Ala Ala Leu Pro | 104 |
| JO-69CAC32053 putative secreted protein [*Mycobacterium leprae*] | Ala Leu Leu Ala Val Val Ala Ala | 105 |
| JO-70NP_630954 secreted protein [*Streptomyces coelicolor* A3(2)] | Ala Val Val Val Val Leu Pro Ile Leu Leu | 106 |
| JO-71P97300 Neuroplastin precursor (Stromal cell-derived receptor 1) (SDR-1) | Ala Leu Ala Leu Leu Leu Leu Val Pro | 107 |
| JO-72AAA41949 Rat parotid gland acidic proline-rich protein mRNA, S complete CD | Leu Val Val Leu Leu Ala Ala Leu Leu Val Leu | 108 |
| JO-73AAA17887 *Drosophila melanogaster* spatzle (spz) gene | Pro Val Leu Leu Leu Leu Ala Pro | 109 |

TABLE 1e-continued

| MTD | Origin | Amino acid sequence | SEQ ID NO |
|---|---|---|---|
| JO-74 | NP_627867 conserved secreted protein [*Streptomyces coelicolor* A3(2)] | Ala Leu Ala Val Val Ala Ala Pro | 110 |
| JO-75 | NP_631283 secreted protein [*Streptomyces coelicolor* A3(2)] | Val Ile Val Ala Leu Leu Ala Val | 111 |
| JO-76 | NP_003231 endometrial bleeding associated factor preproprotein [*Homo sapiens*] | Ala Leu Val Leu Pro Leu Ala Pro | 6 |
| JO-77 | CAB76313 putative secreted protein [*Streptomyces coelicolor* A3(2)] | Ala Val Ala Leu Leu Ile Leu Ala Val | 8 |
| JO-78 | P07198 Xenopsin precursor [Contains: Xenopsin precursor fragment (XPF); Xenopsin] | Val Leu Leu Ala Val Ile Pro | 112 |
| JO-79 | NP_631293 secreted protein [*Streptomyces coelicolor* A3(2)] | Leu Ile Val Ala Ala Val Val Val Val Ala Val Leu Ile | 113 |
| JO-80 | NP_626373 secreted protein [*Streptomyces coelicolor* A3(2)] | Ala Val Val Val Ala Ala Pro | 114 |
| JO-81 | NP_624952 secreted cellulose-binding protein [*Streptomyces coelicolor* A3(2)] | Leu Ala Ala Val Leu Leu Leu Ile Pro | 115 |
| JO-82 | NP_009104 protease, serin, 23 precursor [*Homo sapiens*] | Leu Leu Leu Leu Leu Leu Ala Val Val Pro | 116 |
| JO-83 | AAK63068 phytotoxic protein PcF precursor [*Phytophthora cactorum*] | Ala Val Ala Leu Val Ala Val Val Ala Val Ala | 117 |
| JO-84 | NC_003903 *Streptomyces coelicolor* A3(2) plasmid SCP1, complete sequence | Leu Val Ala Ala Leu Leu Ala Val Leu | 118 |

TABLE 1f

| MTD | Origin | Amino acid sequence | SEQ ID NO |
|---|---|---|---|
| JO-85 | NP_629842 peptide transport system secreted peptide binding protein [*Streptomyces coelicolor* A3(2)] | Leu Leu Ala Ala Ala Ala Ala Leu Leu Leu Ala | 119 |
| JO-86 | NP_854067 Posible secreted protein [*Mycobacterium bovis* AF2122/97] | Leu Ala Val Leu Ala Ala Ala Pro | 120 |
| JO-87 | NP_627802 secreted protein [*Streptomyces coelicolor* A3(2)] | Val Val Val Leu Leu Val Leu Leu Ala Leu Val Val Val | 121 |
| JO-88 | NP_627802 secreted protein [*Streptomyces coelicolor* A3(2)] | Val Val Ile Ala Val Val Pro | 122 |
| JO-89 | NP_624483 secreted protein [*Streptomyces coelicolor* A3(2)] | Leu Ala Ala Val Ala Ala Leu Ala Val Val | 123 |
| JO-90 | NP_627802 secreted protein [*Streptomyces coelicolor* A3(2)] | Val Leu Leu Val Leu Leu Ala Leu Val | 124 |
| JO-91 | NP_625203 secreted protein [*Streptomyces coelicolor* A3(2)] | Pro Val Leu Val Pro Ala Val Pro | 125 |
| JO-92 | NP_630960 secreted protein [*Streptomyces coelicolor* A3(2)] | Pro Ala Leu Ala Leu Ala Leu Ala | 126 |
| JO-93 | NP_630670 secreted protein [*Streptomyces coelicolor* A3(2)] | Ala Ala Ala Ala Pro Ala Leu Ala | 127 |
| JO-94 | NP_630493 secreted protein [*Streptomyces coelicolor* A3(2)] | Ile Val Leu Pro Val Leu Ala Ala Pro | 128 |
| JO-95 | CAC29994 putative secreted protein [*Mycobacterium leprae*] | Leu Val Leu Leu Leu Leu Pro Leu Leu Ile | 129 |

TABLE 1f-continued

| MTD | Origin | Amino acid sequence | SEQ ID NO |
|---|---|---|---|
| JO-96 | NP_624483 secreted protein [*Streptomyces coelicolor* A3(2)] | Leu Ala Ala Val Ala Pro Ala Leu Ala Val Val | 130 |
| JO-97 | NP_037375 secretogranin III [*Homo sapiens*] | Ile Leu Val Leu Val Leu Pro Ile | 131 |
| JO-98 | NP_009199 V-set and immunoglobulin domain containing 4 [*Homo sapiens*] | Ile Leu Leu Pro Leu Leu Leu Leu Pro | 132 |
| JO-99 | NP_733650 secreted hydrolase [*Streptomyces coelicolor* A3(2)] | Ile Ala Pro Ala Val Val Ala Ala Leu Pro | 133 |
| JO-100 | NP_057540 transmembrane protein 9 [*Homo sapiens*] | Leu Leu Leu Val Ala Val Val Pro Leu Leu Val Pro | 134 |
| JO-76 | CAI74362 hypothetical protein [*Theileria annulata*] | Leu Ile Leu Leu Leu Leu Pro Ile Ile | 135 |
| JO-102 | NP-630671 secreted protein [*Streptomyces coelicolor* A3(2)] | Ala Val Leu Ala Ala Pro Ala Val Leu Val | 136 |
| JO-77 | NP_065695 TMEM9 domain family, member B [*Homo sapiens*] | Leu Ala Leu Pro Val Leu Leu Leu Ala | 137 |
| JO-104 | P06908 Pulmonary surfactant-associated protein A precursor (SP-A) (PSP-A) (PSAP) | Leu Ala Leu Ala Leu Leu Leu | 138 |

TABLE 1g

| MTD | Origin | Amino acid sequence | SEQ ID NO |
|---|---|---|---|
| JO-105 | NP_639721 putative secreted protein [*Streptomyces coelicolor* A3(2)] | Val Ala Val Pro Leu Leu Val Val Ala | 139 |
| JO-106 | NP_854954 CONSERVED PROBABLE SECRETED PROTEIN [*Mycobacterium bovis* AF2122/97] | Ala Val Ala Val Ala Pro Val Ala Ala Ala Ala | 140 |
| JO-107 | NP_627759 secreted protein [*Streptomyces coelicolor* A3(2)] | Ala Ala Ala Val Val Ala Ala Val Pro Ala Ala | 141 |
| JO-108 | NP_003842 cellular repressor of E1A-stimulated genes [*Homo sapiens*] | Ala Leu Leu Ala Ala Leu Leu Ala Pro | 142 |
| JO-109 | NP_003842 cellular repressor of E1A-stimulated genes [*Homo sapiens*] | Leu Leu Ala Leu Leu Val Pro | 143 |
| JO-110 | NP_003842 cellular repressor of E1A-stimulated genes [*Homo sapiens*] | Ala Leu Leu Ala Ala Leu Leu Ala Leu Leu Ala Leu Leu Val | 144 |
| JO-111 | NP_000589 *Homo sapiens* insulin-like growth factor binding protein 3 (IGFBP3) | Ala Ala Ala Leu Pro Leu Leu Val Leu Leu Pro | 145 |
| JO-112 | CAB594459 putative secreted protein [*Streptomyces coelicolor* A3(2)] | Ala Ala Ala Val Pro Ala Ala Leu Ala Pro | 146 |
| JO-113 | NP_628917 secreted protein [*Streptomyces coelicolor* A3(2)] | Ala Ala Leu Ala Val Ala Ala Leu Ala Ala | 147 |
| JO-114 | NP_624695 secreted protein [*Streptomyces coelicolor* A3(2)] | Ala Val Leu Ala Ala Ala Val Pro | 148 |
| JO-115 | NP_624695 secreted protein [*Streptomyces coelicolor* A3(2)] | Val Ala Ala Leu Pro Ala Pro Ala | 149 |
| JO-116 | NP_624791 secreted protein [*Streptomyces coelicolor* A3(2)] | Ala Leu Ala Leu Ala Val Pro Ala Val Leu Pro | 150 |
| JO-117 | CAB45579 putative secreted protein [*Streptomyces coelicolor* A3(2)] | Ala Ala Leu Leu Pro Ala Ala Val Ala Val Pro | 151 |
| JO-118 | NP_627066 secreted protein [*Streptomyces coelicolor* A3(2)] | Ala Val Val Val Ala Leu Ala Pro | 152 |

TABLE 1g-continued

| MTD | Origin | Amino acid sequence | SEQ ID NO |
|---|---|---|---|
| JO-119 | NP_630174 secreted substrate-binding protein [*Streptomyces coelicolor* A3(2)] | Ala Ala Ala Val Ala Leu Pro Ala Ala Ala Ala Leu Leu Ala | 153 |
| JO-120 | P06727 Apolipoprotein A-IV precursor (Apo-AIV) (ApoA-IV) *Homo sapiens* | Ala Val Val Leu Pro Leu Ala Leu Val Ala Val Ala Pro | 154 |
| JO-121 | Q62087 Serum paraoxonase/lactonase 3. *Mus musculus* | Leu Val Ala Leu Pro Leu Leu Pro | 155 |
| JO-122 | NP_627123 probable secreted penicillin-binding protein [*Streptomyces coelicolor* A3(2)] | Val Val Val Pro Leu Leu Leu Ile Val Pro | 156 |

TABLE 1h

| MTD | Origin | Amino acid sequence | SEQ ID NO |
|---|---|---|---|
| JO-123 | CAC30224 putative secreted hydrolase [*Mycobacterium leprae*] | Leu Ala Val Val Leu Ala Val Pro | 157 |
| JO-124 | OZZQAM circumsporozoite protein precursor-*Plasmodium cynomolgi* | Leu Leu Ala Val Pro Ile Leu Leu Val Pro | 158 |
| JO-125 | Q15166 Serum paraoxonase/lactonase 3 [*Homo sapiens*] | Leu Val Ala Leu Val Leu Leu Pro | 159 |
| JO-126 | NP_060220 all-trans-13,14-dihydroretinol saturase [*Homo sapiens*] | Leu Val Leu Leu Leu Ala Val Leu Leu Leu Ala Val Leu Pro | 160 |
| JO-127 | AL627273 *Salmonella enterica* serovar Typhi (*Salmonella typhi*) strain CT18 | Leu Leu Ala Pro Val Val Ala Leu Val Ile Leu Pro | 161 |
| JO-128 | NP_625987 secreted protein [*Streptomyces coelicolor* A3(2)] | Val Leu Ala Val Leu Ala Val Pro Val Leu Leu Leu Pro | 162 |
| JO-129 | CAB45474 putative secreted protein [*Streptomyces coelicolor* A3(2)] | Val Val Ile Ala Val Val Pro Val Val Val | 163 |
| JO-130 | CAB45474 putative secreted protein [*Streptomyces coelicolor* A3(2)] | Leu Leu Val Leu Leu Ala Leu Val Val Val Pro | 164 |
| JO-131 | CAB36605 putative secreted protein [*Streptomyces coelicolor* A3(2)] | Val Leu Leu Ala Leu Pro Val Val Ala Ala Pro | 165 |
| JO-132 | NP_628377 NLP/P60-family secreted protein [*Streptomyces coelicolor* A3(2)] | Ala Val Val Val Pro Ala Ile Val Leu Ala Ala Pro | 166 |
| JO-133 | CAB59594 putative secreted protein [*Streptomyces coelicolor* A3(2)] | Ala Val Leu Val Pro Ala Ala Ala Leu Val Pro | 167 |
| JO-134 | NP_624974 secreted protein [*Streptomyces coelicolor* A3(2)] | Val Val Ala Ala Leu Pro Leu Val Leu Pro | 168 |
| JO-135 | NP_733682 secreted ATP/GTP binding protein [*Streptomyces coelicolor* A3(2)] | Ala Ala Val Ala Leu Pro Ala Ala Ala Pro | 169 |
| JO-136 | P27169 Serum paraoxonase/arylesterase 1 (PON 1) (Serum aryldialkylphosphatase 1) (A-esterase 1) *Homo sapiens* | Leu Ile Ala Leu Pro Leu Leu Pro | 170 |
| JO-137 | P52430 Serum paraoxonase/arylesterase 1 (PON 1) (Serum aryldialkylphosphatase 1) (A-esterase 1) *Homo sapiens* | Leu Leu Ala Leu Pro Leu Val Leu Val Leu Ala Leu Pro | 171 |

TABLE 1i

| MTD | Origin | Amino acid sequence | SEQ ID NO |
|---|---|---|---|
| JO-138 | NP_626569 secreted protein [Streptomyces coelicolor A3(2)] | Ile Val Pro Leu Leu Leu Ala Ala Pro | 172 |
| JO-139 | NP_940995 C1q and tumor necrosis factor related protein 1 isoform 1 [Homo sapiens] | Leu Leu Leu Ala Pro Leu Leu Leu Ala Pro | 173 |
| JO-140 | NP_626174 large secreted protein [Streptomyces coelicolor A3(2)] | Leu Ala Ala Leu Pro Val Ala Ala Val Pro | 174 |
| JO-141 | CAB83860 putative protein-export integral membrane protein [Neisseria meningitidis Z2491] | Ala Leu Ala Val Ile Val Leu Val Leu Leu | 175 |
| JO-142 | NP_001009551 cornichon-like isoform 2 [Homo sapiens] | Leu Ala Leu Leu Leu Pro Ala Ala Leu Ile | 176 |
| JO-143 | NP_626808 secreted protein [Streptomyces coelicolor A3(2)] | Ala Leu Leu Pro Leu Leu Ala Val Val Leu Pro | 177 |
| JO-144 | NP_639798 putative secreted protein [Streptomyces coelicolor A3(2)] | Ala Ile Ala Val Pro Val Leu Ala Ala Pro | 178 |
| JO-145 | NP_000492 Homo sapiens elastin (supravalvular aortic stenosis) | Ala Ala Ala Pro Val Leu Leu Leu Leu Leu | 179 |
| JO-146 | NP_630680 secreted sugar binding protein [Streptomyces coelicolor A3(2)] | Ala Ala Ala Val Ala Val Leu Ala Leu Ala Pro | 180 |
| JO-147 | CAB56129 putative secreted protein [Streptomyces coelicolor A3(2)] | Ala Ala Leu Ala Ala Leu Val Val Ala Ala Pro | 181 |
| JO-148 | NP_625109 secreted solute-binding lipo-protein [Streptomyces coelicolor A3(2)] | Ala Ala Leu Ala Ala Val Pro Leu Ala Leu Ala Pro | 182 |
| JO-149 | NP_733579 secreted sugar-binding protein [Streptomyces coelicolor A3(2)] | Ala Leu Ala Val Ala Ala Pro Ala Leu Ala Leu Leu Pro | 183 |
| JO-150 | NP_630126 secreted chitinase (secreted protein) [Streptomyces coelicolor A3(2)] | Ala Ala Leu Pro Ala Ala Ala Pro | 184 |
| JO-151 | NP_630126 secreted chitinase (secreted protein) [Streptomyces coelicolor A3(2)] | Ala Ala Ala Pro Val Ala Ala Val Pro | 185 |
| JO-152 | NP_872425 secretory protein LOC348174 [Homo sapiens] | Leu Leu Ala Val Leu Leu Ala Leu Leu Pro | 186 |
| JO-153 | NP_630107 secreted protein [Streptomyces coelicolor A3(2)] | Val Leu Ala Leu Leu Val Ala Val Val Pro | 187 |

TABLE 1j

| MTD | Origin | Amino acid sequence | SEQ ID NO |
|---|---|---|---|
| JO-154 | NP_733688 peptide-binding transport protein [Streptomyces coelicolor A3(2)] | Ala Leu Val Val Pro Ala Ala Val Pro | 188 |
| JO-155 | NP_629904 secreted protein [Streptomyces coelicolor A3(2)] | Ala Val Val Leu Pro Leu Leu Leu Pro | 189 |
| JO-156 | YP_177852 MCE-FAMILY PROTEIN MCE3A [Mycobacterium tuberculosis H37Rv] | Ala Val Ile Pro Val Ala Val Leu Val Pro | 190 |
| JO-157 | CAA19627 putative secreted solute binding protein [Streptomyces coelicolor A3(2)] | Ala Ala Ala Val Pro Ala Ala Val Leu Ala Pro | 191 |
| JO-158 | NP_639884 putative large secreted protein [Streptomyces coelicolor A3(2)] | Val Ala Val Pro Val Val Leu Ala Ile Leu Pro | 192 |
| JO-159 | P24327 Foldase protein prsA precursor | Ile Ala Ile Ala Ala Ile Pro Ala Ile Leu Ala Leu | 193 |

TABLE 1j-continued

| MTD | Origin | Amino acid sequence | SEQ ID NO |
|---|---|---|---|
| JO-160 | CAB84808 putative membrane lipoprotein [*Neisseria meningitidis* Z2491] | Ala Leu Ile Ala Pro Ala Leu Ala Ala Pro | 194 |
| JO-161 | NP_639883 putative large secreted protein [*Streptomyces coelicolor* A3(2)] | Ala Ala Ile Ala Leu Val Ala Pro Ala Leu | 195 |
| JO-162 | NP_639883 putative large secreted protein [*Streptomyces coelicolor* A3(2)] | Leu Ala Pro Ala Val Ala Ala Ala Pro | 196 |
| JO-163 | NP_627362 secreted protein [*Streptomyces coelicolor* A3(2)] | Val Ala Ile Ile Val Pro Ala Val Val Ala Ile Ala Leu Ile Ile | 197 |
| JO-164 | NP_627362 secreted protein [*Streptomyces coelicolor* A3(2)] | Ala Val Val Ala Ile Ala Leu Ile Ile | 198 |
| JO-165 | NP_624625 secreted protein [*Streptomyces coelicolor* A3(2)] | Leu Ala Ala Val Pro Ala Ala Ala Pro | 199 |
| JO-166 | NP_624625 secreted protein [*Streptomyces coelicolor* A3(2)] | Ala Val Ala Ala Leu Pro Leu Ala Ala Pro | 200 |
| JO-167 | NP_624625 secreted protein [*Streptomyces coelicolor* A3(2)] | Leu Ala Ala Pro Ala Ala Ala Ala Pro | 201 |
| JO-168 | NP_626936 secreted protein [*Streptomyces coelicolor* A3(2)] | Leu Ala Ala Val Val Pro Val Ala Ala Ala Val Pro | 202 |
| JO-169 | NP_626936 secreted protein [*Streptomyces coelicolor* A3(2)] | Val Ala Ala Pro Ala Ala Ala Ala Pro | 203 |
| JO-170 | NP_626936 secreted protein [*Streptomyces coelicolor* A3(2)] | Ala Val Pro Val Pro Val Pro Leu | 204 |

TABLE 1k

| MTD | Origin | Amino acid sequence | SEQ ID NO |
|---|---|---|---|
| JO-171 | NP_085072 matrilin 2 isoform b precursor [*Homo sapiens*] | Leu Leu Ile Leu Pro Ile Val Leu Leu Pro | 205 |
| JO-172 | CAB94057 putative secreted protein [*Streptomyces coelicolor* A3(2)] | Ala Leu Ala Leu Pro Ala Leu Ala Ile Ala Pro | 206 |
| JO-173 | NP_624384 secreted protein [*Streptomyces coelicolor* A3(2)] | Ala Val Ile Pro Ile Leu Ala Val Pro | 207 |
| JO-174 | NP_733505 large, multifunctional secreted protein [*Streptomyces coelicolor* A3(2)] | Leu Ile Leu Leu Leu Pro Ala Val Ala Leu Pro | 208 |
| JO-175 | CAB45630 putative secreted protein [*Streptomyces coelicolor* A3(2)] | Ile Val Leu Ala Pro Val Pro Ala Ala Ala | 209 |
| JO-176 | NP_627887 secreted protein [*Streptomyces coelicolor* A3(2)] | Val Val Val Val Pro Val Leu Ala Ala Ala Ala | 210 |
| JO-177 | P06832 *Bacillolysin* precursor | Leu Val Ala Val Ala Ala Pro | 211 |
| JO-178 | NP_625998 secreted protein [*Streptomyces coelicolor* A3(2)] | Leu Val Leu Ala Ala Pro Ala Ala Leu Pro | 212 |
| JO-179 | NP_625057 secreted protein [*Streptomyces coelicolor* A3(2)] | Leu Ile Ala Pro Ala Ala Ala Val Pro | 213 |
| JO-180 | NP_443750 ADP-ribosyltransferase 5 precursor [*Homo sapiens*] | Ala Leu Ala Ala Leu Pro Ile Ala Leu Pro | 214 |
| JO-181 | CAB84257 putative secreted protein [*Neisseria meningitidis* Z2491] | Ala Val Leu Leu Leu Pro Ala Ala Ala | 215 |
| JO-182 | P00634 Alkaline phosphatase precursor (APase) | Ile Ala Leu Ala Leu Leu Pro Leu Leu | 216 |
| JO-183 | NP_000933 peptidylprolyl isomerase B precursor [*Homo sapiens*] | Val Leu Leu Ala Ala Ala Leu Ile Ala Pro | 217 |

TABLE 1k-continued

| MTD | Origin | Amino acid sequence | SEQ ID NO |
|---|---|---|---|
| JO-184 | CAB71258 putative secreted protein [Streptomyces coelicolor A3(2)] | Ala Pro Ala Val Leu Pro Pro Val Val Val Ile | 218 |
| JO-185 | CAC31847 possible secreted protein [Mycobacterium leprae] | Val Val Gly Leu Leu Val Ala Ala Leu | 219 |
| JO-186 | NP_626948 secreted protein [Streptomyces coelicolor A3(2)] | Ala Ala Ile Ala Ala Ala Ala Pro Leu Ala Ala | 220 |
| JO-187 | NP_059120 cat eye syndrome critical region protein 1 isoform a precursor [Homo sapiens] | Leu Leu Leu Ala Val Ala Pro | 221 |
| JO-188 | NP_006519 tissue factor pathway inhibitor 2 [Homo sapiens] | Leu Ile Leu Leu Leu Pro Leu Ala Ala Leu | 222 |

TABLE 1l

| MTD | Origin | Amino acid sequence | SEQ ID NO |
|---|---|---|---|
| JO-189 | P97299 Secreted frizzled-relating protein 2 precursor (sFRP-2) (Secreted apoptosis-relating protein 1) | Ala Leu Leu Leu Leu Val Leu Ala | 223 |
| JO-190 | NP_071447 tubulointerstitial nephritis antigen-like 1 | Leu Leu Leu Leu Leu Leu Pro Leu Ala | 224 |
| JO-191 | NP_056322 epidermal growth factor-like protein 6 precursor [Homo sapiens] | Leu Ala Leu Pro Leu Leu Leu Pro | 225 |
| JO-192 | NP_628035 secreted penicillin-binding protein [Streptomyces coelicolor A3(2)] | Leu Leu Val Leu Pro Leu Leu Ile | 226 |
| JO-193 | NP_683880 cathepsin H isoform b precursor [Homo sapiens] | Leu Pro Leu Leu Pro Ala Ala Leu Val | 227 |
| kFGF4-derived MTD | kaposi fibroblast growth factor 4, kFGF4 | Ala Ala Val Leu Leu Pro Val Leu Leu Ala Ala Pro | 228 |

In some embodiments, the present invention may employ a kaposi fibroblast growth factor 4 (kFGF4)-derived MTD having the nucleotide sequence of SEQ ID NO: 3 and the amino acid sequence of SEQ ID NO: 4 (hereinafter, "MTD$_1$"), a JO-76 MTD having the nucleotide sequence of SEQ ID NO: 5 and the amino acid sequence of SEQ ID NO: 6 which is a hypothetical protein derived from *Theileria annulata* (hereinafter, "MTD$_2$"), and a JO-77 MTD having the nucleotide sequence of SEQ ID NO: 7 and the amino acid sequence of SEQ ID NO: 8 which belongs to member B of a human TMEM9 domain family (hereinafter, "MTD$_3$"), as the MTD capable of mediating the transport of the metastasis suppressor Nm23 into a cell.

The cell permeable Nm23 recombinant proteins according to the present invention have a structure where one of the three MTDs (kFGF4-derived MTD: MTD$_1$, JO-76: MTD$_2$, JO-77: MTD$_3$) is fused to one terminus or both termini of a metastasis suppressor protein Nm23, and a SV40 large T antigen-derived nuclear localization sequence (NLS)(nucleotide sequence of SEQ ID NO: 9, amino acid sequence of SEQ ID NO:10) and a histidine-tag (His-Tag) affinity domain for easy purification are fused to one terminus of the resulting construct.

In another embodiment, the present invention relates to the construction of eight full-length forms of a cell permeable Nm23 recombinant protein by using one of a kFGF4-derived MTD, a JO-76 MTD and a JO-77 MTD.

As used herein, the term "full-length form" refers to a construct including the entire amino acid sequence of the metastasis suppressor protein Nm23 which does not contain any deletion, addition, insertion or substitution of one or more amino acid residues in the amino acid sequence of SEQ ID NO: 2. However, it should be obvious to a skilled person in the art that Nm23 derivatives including various kinds of modifications through the deletion, addition, insertion or substitution of one or more amino acid residues in the amino acid sequence of SEQ ID NO: 2 that is made within the scope of not causing a deterioration of the Nm23 anti-metastatic effect can be used in the present invention.

Referring to FIG. 1, the full-length forms of the cell permeable Nm23 recombinant protein are as follows:

1) His-MTD$_1$-Nm23 (HM$_1$N), where a kFGF4-derived MTD is fused to the N-terminus of a full-length Nm23, 2) His-Nm23-MTD$_1$ (HNM$_1$), where a kFGF4-derived MTD is fused to the C-terminus of a full-length Nm23, 3) His-MTD$_1$-Nm23-MTD$_1$ (HM$_1$NM$_1$) where a kFGF4-derived MTD is fused to both termini of a full-length Nm23, 4) His-MTD$_2$-Nm23 (HM$_2$N), where a JO-76 MTD is fused to the N-terminus of a full-length Nm23, 5) His-Nm23-MTD$_2$ (HNM$_2$), where a JO-76 MTD is fused to the C-terminus of a full-length Nm23, 6) His-MTD$_3$-Nm23 (HM$_3$N), where a JO-77 MTD is fused to the N-terminus of a full-length Nm23, 7) His-Nm23-MTD$_3$ (HNM$_3$), where a JO-77 MTD is fused to the C-terminus of a full-length Nm23, and 8) His-MTD$_3$-Nm23-MTD$_3$ (HM$_3$NM$_3$), where a JO-77 MTD is fused to both termini of a full-length Nm23, where a His-tag and a NLS derived from SV40 large T antigen are covalently coupled to the N-terminus of the above constructs.

As for the full-length forms of the cell permeable Nm23 recombinant protein constructed by using a kFGF4-derived MTD as described above, His-MTD$_1$-Nm23 (HM$_1$N) has an amino acid sequence represented by SEQ ID NO: 22, while a polynucleotide encoding the same has a nucleotide sequence represented by SEQ ID NO: 21; His-Nm23-MTD$_1$ (HNM$_1$) has an amino acid sequence represented by SEQ ID NO: 24, while a polynucleotide encoding the same has a nucleotide sequence represented by SEQ ID NO: 23; and His-MTD$_1$-Nm23-MTD$_1$ (HM$_1$NM$_1$) has an amino acid sequence represented by SEQ ID NO: 26, while a polynucleotide encoding the same has a nucleotide sequence represented by SEQ ID NO: 25.

As for the full-length forms of the cell permeable Nm23 recombinant protein constructed by using a JO-76 MTD as described above, His-MTD$_2$-Nm23 (HM$_2$N) has an amino acid sequence represented by SEQ ID NO: 28, while a polynucleotide encoding the same has a nucleotide sequence represented by SEQ ID NO: 27; and His-Nm23-MTD$_2$ (HNM$_2$) has an amino acid sequence represented by SEQ ID NO: 30, while a polynucleotide encoding the same has a nucleotide sequence represented by SEQ ID NO: 29.

As for the full-length forms of the cell permeable Nm23 recombinant protein constructed by using a JO-77 MTD as described above, His-MTD$_3$-Nm23 (HM$_3$N) has an amino acid sequence represented by SEQ ID NO: 32, while a polynucleotide encoding the same has a nucleotide sequence represented by SEQ ID NO: 31; His-Nm23-MTD$_3$ (HNM$_3$) has an amino acid sequence represented by SEQ ID NO: 34, while a polynucleotide encoding the same has a nucleotide sequence represented by SEQ ID NO: 33; and His-MTD$_3$-Nm23-MTD$_3$ (HM$_3$NM$_3$) has an amino acid sequence represented by SEQ ID NO: 36, while a polynucleotide encoding the same has a nucleotide sequence represented by SEQ ID NO: 35.

As a control for the cell permeable Nm23 recombinant proteins, His-Nm23 (HN), where a full-length Nm23 is fused only to a NLS derived from SV40 large T antigen and a histidine-tag (His-Tag) without any MTD, is constructed. The control protein has an amino acid sequence represented by SEQ ID NO: 20, while a polynucleotide encoding the same has a nucleotide sequence represented by SEQ ID NO: 19.

Further, the present invention provides an expression vector containing the polynucleotide encoding each of the cell permeable Nm23 recombinant proteins described above, and a transformant capable of producing each of the cell permeable Nm23 recombinant proteins at high levels, which is obtainable by transforming a host cell using the expression vector.

As used herein, the term "expression vector" is a vector capable of expressing a target protein or a target RNA in a suitable host cell. The nucleotide sequence of the present invention may be present in a vector in which the nucleotide sequence is operably linked to regulatory sequences capable of providing for the expression of the nucleotide sequence by a suitable host cell.

Within an expression vector, the term "operably linked" is intended to mean that the nucleotide sequence of interest is linked to the regulatory sequence(s) in a manner which allows for expression of the nucleotide sequence. The term "regulatory sequence" is intended to include promoters, enhancers, and other expression control elements. Such operable linkage with the expression vector can be achieved by conventional gene recombination techniques known in the art, while site-directed DNA cleavage and linkage are carried out by using conventional enzymes known in the art.

The expression vectors suitable for the present invention may include plasmid vectors, cosmid vectors, bacteriophage vectors, viral vectors and the like, but are not limited thereto. The expression vectors for use in the present invention may contain a signal sequence or a leader sequence for membrane targeting or secretion, as well as regulatory sequences such as a promoter, an operator, an initiation codon, a termination codon, a polyadenylation signal, an enhancer and the like. The promoter may be a constitutive or an inducible promoter. Further, the expression vector may include one or more selectable marker genes for selecting the host cell containing the expression vector, and may further include a nucleotide sequence that enables the vector to replicate in the host cell in question.

The expression vector constructed according to the present invention may be exemplified by pET28a(+)-HNM$_1$ where the polynucleotide encoding the recombinant protein HNM$_1$ where a kFGF4-derived MTD is fused to the C-terminus of a full-length Nm23 is inserted into a cleavage site of NdeI restriction enzyme within the multiple cloning sites (MCS) of a pET-28a(+) vector.

In another embodiment, the polynucleotide of the present invention is cloned into a pET-28a(+) vector (NOVAGEN, USA) bearing a His-tag sequence so as to fuse six histidine residues to the N-terminus of the cell permeable Nm23 recombinant protein to allow easy purification.

Accordingly, the cell permeable Nm23 recombinant protein expressed in the above expression vector has a structure where one of a kFGF4-derived MTD, a JO-76 MTD and a JO-77 MTD is fused to the full-length or truncated Nm23, and a His-tag and NLS are linked to the N-terminus thereof.

The present invention further provides a transformant capable of producing each of the cell permeable Nm23 recombinant proteins at high levels which is obtainable by transforming a host cell using the expression vector. The host cell suitable for the present invention may be eukaryotic cells, such as E. coli. In one embodiment of the present invention, E. coli used as a host cell is transformed with the expression vector, for example, pET28a(+)-HNM$_1$ containing the polynucleotide encoding the cell permeable recombinant protein HNM$_1$ where a kFGF4-derived MTD is fused to the C-terminus of a full-length Nm23 according to the present invention so as to produce the cell permeable Nm23 recombinant protein at high levels. Methods for transforming bacterial cells are well known in the art, and include, but are not limited to, biochemical means such as transformation, transfection, conjugation, protoplast fusion, calcium phosphate-precipitation, and application of polycations such as diethylaminoethyl (DEAE) dextran, and mechanical means such as electroporation, direct microinjection, microprojectile bombardment, calcium phosphate (CaPO$_4$) precipitation, calcium chloride (CaCl$_2$) precipitation, PEG-mediated fusion and liposome-mediated method.

In some embodiments, the transformants obtained by transforming E. coli DH5α with the expression vector containing the cell permeable Nm23 recombinant protein HM$_3$N where a JO-77 MTD is fused to the N-terminus of a full-length Nm23, and the expression vector containing the cell permeable Nm23 recombinant protein HNM$_3$ where a JO-77

MTD is fused to the C-terminus thereof, respectively, were deposited under accession numbers KCTC-11380BP and KCTC-11381BP, respectively, with the Korean Collection for Type Cultures (KCTC), Korea Research Institute of Bioscience and Biotechnology (KRIBB), 52, Oun-Dong, Yusong-Ku, Taejon 305-333, Republic of Korea. All deposits referred to herein were made on Aug. 28, 2008 in accordance with the Budapest Treaty, and all restrictions imposed by the depositor on the availability to the public of the deposited biological material will be irrevocably removed upon the granting of the patent.

The present invention provides a method of producing the cell permeable Nm23 recombinant proteins at high levels, which includes the step of culturing the above transformant.

The method of the present invention may be carried out by culturing the transformant in a suitable medium under suitable conditions for expressing a cell permeable Nm23 recombinant protein of the present invention in the expression vector introduced into the transformant. Methods for expressing a recombinant protein by culturing a transformant are well known in the art, and for example, may be carried out by inoculating a transformant in a suitable medium for growing the transformant, performing a subculture, transferring the same to a main culture medium, culturing under suitable conditions, for example, supplemented with a gene expression inducer, isopropyl-β-D-thiogalactoside (IPTG) and, thereby, inducing the expression of a recombinant protein. After the culture is completed, it is possible to recover a "substantially pure" recombinant protein from the culture solution. The term "substantially pure" means that the recombinant protein and polynucleotide encoding the same of the present invention are essentially free of other substances with which they may be found in nature or in vivo systems to the extent practical and appropriate for their intended use.

A recombinant protein of the present invention obtained as above may be isolated from the inside or outside (e.g., medium) of host cells, and purified as a substantially pure homogeneous polypeptide. The method for polypeptide isolation and purification is not limited to any specific method. In fact, any standard method may be used. For instance, chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide. As for chromatography, affinity chromatography, ion-exchange chromatography, hydrophobic chromatography, gel filtration chromatography, reverse phase chromatography, adsorption chromatography, etc., for example, may be used (Maniatis et al., *Molecular Cloning*: A Laboratory Manual, Cold Spring Harbor Laboratory, Cold Spring Harbor, N.Y., 1982; Sambrook et al., *Molecular Cloning*: A Laboratory Manual, 2d Ed., Cold Spring Harbor Laboratory Press, 1989; Deutscher, M., *Guide to Protein Purification Methods Enzymology* vol. 182. Academic Press. Inc., San Diego, Calif., 1990).

Meanwhile, the recombinant protein expressed in the transformants according to the present invention can be classified into a soluble fraction and an insoluble fraction according to protein characteristics during the protein purification process. If the majority of the expressed recombinant proteins are present in the soluble fraction, the recombinant protein can be isolated and purified according to the method as described above. However, when the majority of the expressed recombinant proteins are present in the insoluble fraction, i.e., as inclusion bodies, the recombinant proteins are first solubilized by using polypeptide denaturing agents, e.g., urea, guanidine HCl, or detergents, and then, purified by performing a series of centrifugation, dialysis, electrophoresis and column chromatography. Since there is the risk of losing the recombinant protein's activity due to a structural modification caused by the polypeptide denaturing agent, the process of purifying the recombinant protein from the insoluble fraction requires desalting and refolding steps. That is, the desalting and refolding steps can be performed by dialysis and dilution with a solution that does not include a polypeptide denaturing agent or by centrifugation with a filter. Further, if a salt concentration of the solution used for the purification of a recombinant protein from a soluble fraction is relatively high, such desalting and refolding steps may be performed.

In some embodiments, it has been found that the cell permeable Nm23 recombinant protein of the present invention mostly exists in the insoluble fraction as an inclusion body. In order to purify the recombinant protein from the insoluble fraction, the insoluble fraction may be dissolved in a lysis buffer containing a non-ionic surfactant such as Triton X-100, subjected to ultrasonification, and then centrifuged to separate a precipitate. The separated precipitate may be dissolved in a buffer supplemented with a strong denaturing agent, such as urea, and centrifuged to separate the supernatant. The above separated supernatant is purified by means of a histidin-tagged protein purification kit and subjected to ultrafiltration, for example, by using an amicon filter for salt removal and protein refolding, thereby obtaining a purified recombinant protein of the present invention.

Further, the present invention provides an anti-metastatic pharmaceutical composition including the cell permeable Nm23 recombinant protein as an effective ingredient for preventing metastasis by inhibiting the proliferation, differentiation and migration of cancer cells and inducing apoptosis.

The metastasis suppressor Nm23, which functions as an important target protein for signal transduction cascades including KSR and Ras-mediated MAPK, can control the MAPK signal transduction cascade mediated by KSR phosphorylation, and thus, inhibit the proliferation, differentiation and migration of cancer cells and induce apoptosis. Therefore, the cell permeable Nm23 recombinant proteins of the present invention can be effectively used as an anti-metastatic agent capable of preventing and/or treating cancer metastasis.

The cell permeable Nm23 recombinant proteins of the present invention can activate cell signaling mechanisms involved in the activation of ATM and p53 that induce cell cycle arrest and apoptosis in response to DNA damage or oncogenic signals by efficiently introducing a metastasis suppressor protein Nm23 into a cell. Therefore, the cell permeable Nm23 recombinant proteins of the present invention can be effectively used as an anti-metastatic agent for treating various kinds of human cancers.

The pharmaceutical composition comprising the recombinant protein of the present invention as an effective ingredient may further include pharmaceutically acceptable carriers suitable for oral administration or parenteral administration. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (*Remington's Pharmaceutical Sciences*, 19th ed., Mack Publishing Company, Easton, Pa., 1995). The carriers for oral administration may include lactose, starch, cellulose derivatives, magnesium stearate, stearic acid and the like. In case of oral administration, the recombinant protein of the present invention can be formulated in the form of chewable tablets, buccal tablets, troches, capsules, elixir, suspensions, syrup, wafers or combination thereof by mixing with the carriers. Further, the carriers for parenteral administration may include water, suitable oil, saline, aqueous glucose, glycol and the like, and may further include stabilizers and preservatives. The stabilizers suitable for the present invention may include antioxidants such as sodium bisulfite, sodium sulfite and ascorbic acid. Suitable preservatives may include benzalconium chloride, methly-paraben, propyl-paraben and chlorobutanol.

The pharmaceutical composition of the present invention may be formulated into various parenteral or oral administration forms. Representative examples of the parenteral formulation include those designed for administration by injection. For injection, the recombinant proteins of the present invention may be formulated in aqueous solutions, specifically in physiologically compatible buffers or physiological saline buffer. These injection formulations may be formulated by conventional methods using one or more dispersing agents, wetting agents and suspending agents. For oral administration, the proteins can be readily formulated by combining the proteins with pharmaceutically acceptable carriers well known in the art. Such carriers enable the proteins of the invention to be formulated as tablets, pills, capsules, liquids, gels, syrups, slurries, suspensions and the like, for oral ingestion by a patient to be treated. Such oral solid formulations may include suitable excipients such as diluents (e.g., lactose, dextrose, sucrose, mannitol, sorbitol cellulose and/or glycin) and lubricants (e.g., colloidal silica, talc, stearic acid, magnesium stearate, calcium stearate, and/or polyethylene glycol). The tablets may include binders, such as aluminum silicate, starch, gelatin, gum tragacanth, methyl cellulose, hydroxypropylmethyl-cellulose, sodium carboxymethylcellulose, and/or polyvinylpyrrolidone (PVP), and disintegrating agents, such as cross-linked polyvinylpyrrolidone, agar, or alginic acid or a salt thereof such as sodium alginate. If desired, absorbents, coloring agents, flavoring agents and/or sweeteners may be added. The formulations can be prepared by mixing, granulating or coating according to conventional methods well-known in the art.

If necessary, the pharmaceutical compositions of the present invention may further include pharmaceutical additives, such as preservatives, antioxidants, emulsifiers, buffering agents and/or salts for regulating osmosis and other therapeutically effective materials, and can be formulated according to conventional methods known in the art.

In addition, the pharmaceutical composition of the present invention can be administered via oral routes or parenteral routes such as intravenously, subcutaneously, intranasally or intraperitoneally. The oral administration may include sublingual application. The parenteral administration may include drip infusion and injection such as subcutaneous injection, intramuscular injection, intravenous injection and introtumoral injection.

The total effective amount of the recombinant protein of the present invention can be administered to patients in a single dose or can be administered by a fractionated treatment protocol, in which multiple doses are administered over a more prolonged period of time. Although the amount of the recombinant protein or nucleic acid encoding the same in the pharmaceutical composition of the present invention may vary depending on the severity of diseases, the protein or the nucleic acid may be generally administered several times a day at an effective dose of 5 to 20 mg. However, a suitable dose of the recombinant protein in the pharmaceutical composition of the present invention may depend on many factors, such as age, body weight, health condition, sex, disease severity, diet and excretion of patients, as well as the route of administration and the number of treatments to be administered. In view of the above factors, any person skilled in the art may determine the effective dose of the recombinant protein as an anti-metastatic agent for preventing metastasis in various human cancers. The pharmaceutical composition of the present invention containing the recombinant protein has no special limitations on its formulation, administration route and/or administration mode insofar as it exhibits the effects of the present invention.

EXAMPLES

The following examples are provided to illustrate the embodiments of the present invention in more detail, but are by no means intended to limit its scope.

Example 1

Construction of Cell Permeable Nm23 Recombinant Proteins (CP-Nm23)

Eight full-length forms of a cell permeable Nm23 (CP-Nm23) recombinant protein were constructed by using one of a kFGF4-derived MTD ($MTD_1$), a JO-76MTD ($MTD_3$) and a JO-77 MTD ($MTD_2$) as a macromolecule transduction domain.

Referring to FIG. 1, the full-length forms of CP-Nm23 recombinant constructs were as follows:

1) His-$MTD_1$-Nm23 ($HM_1N$), where a kFGF4-derived MTD is fused to the N-terminus of a full-length Nm23, 2) His-Nm23-$MTD_1$ ($HNM_1$), where a kFGF4-derived MTD is fused to the C-terminus of a full-length Nm23, 3) His-$MTD_1$-Nm23-$MTD_1$ ($HM_1NM_1$) where a kFGF4-derived MTD is fused to both termini of a full-length Nm23, 4) His-$MTD_2$-Nm23 ($HM_2N$), where a JO-76 MTD is fused to the N-terminus of a full-length Nm23, 5) His-Nm23-$MTD_2$ ($HNM_2$), where a JO-76 MTD is fused to the C-terminus of a full-length Nm23, 6) His-$MTD_3$-Nm23 ($HM_3N$), where a JO-77 MTD is fused to the N-terminus of a full-length Nm23, 7) His-Nm23-$MTD_3$ ($HNM_3$), where a JO-77 MTD is fused to the C-terminus of a full-length Nm23, and 8) His-$MTD_3$-Nm23-$MTD_3$ ($HM_3NM_3$), where a JO-77 MTD is fused to both termini of a full-length Nm23, where a His-tag and a NLS derived from SV40 large T antigen are covalently coupled to the N-terminus of the above constructs.

In order to prepare the full-length CP-Nm23 recombinant constructs, polymerase chain reactions (PCRs) were carried out by using the oligonucleotides described in Table 1 below as a primer pair specific for each recombinant construct and a human Nm23 cDNA (SEQ ID NO: 1) as a template. The forward and reverse primers for amplifying $HM_1N$ have nucleotide sequences represented by SEQ ID NOS: 13 and 12, respectively; those for amplifying $HNM_1$ have nucleotide sequences represented by SEQ ID NOS: 11 and 14, respectively; those for amplifying $HM_1NM_1$ have nucleotide sequences represented by SEQ ID NOS: 13 and 14, respectively; those for amplifying $HM_2N$ have nucleotide sequences represented by SEQ ID NOS: 15 and 12, respectively; those for amplifying $HNM_2$ have nucleotide sequences represented by SEQ ID NOS: 11 and 16, respectively; those for amplifying $HM_3N$ have nucleotide sequences represented by SEQ ID NOS: 17 and 12, respectively; those for amplifying HNM$_3$ have nucleotide sequences represented by SEQ ID NOS: 11 and 18, respectively; and those for amplifying HM$_3$NM$_3$ have nucleotide sequences represented by SEQ ID NOS: 17 and 18, respectively.

The oligonucleotides as a forward and reverse primer set specific for each recombinant protein are summarized in Table 2 below.

TABLE 2

| Primer | SEQ ID NO | Sequence |
|---|---|---|
| HN-5' (30 nts) | 11 | CCG CAT ATG GCC AAC TGT GAG CGT ACC TCC |
| HN-3' (33 nts) | 12 | CCG CAT ATG TCA TTC ATA GAT CCA GTT CTG AGC |
| HM$_1$N-5' (72 nts) | 13 | CCG CAT ATG GCA GCC GTT CTT CTC CCT GTT CTT CTT GCC GCA CCC GCC AAC TGT GAG CGT ACC TTC ATT GCG |
| HNM$_1$-3' (72 nts) | 14 | CCG CAT ATG TCA GGG TGC GGC AAG AAG AAC AGG GAG AAG AAC GGC TGC TTC ATA GAT CCA GTT CTG AGC ACA |
| HM$_2$N-5' (60 nts) | 15 | CCG CAT ATG GCG CTG GTG CTG CCG CTG GCG CCG GCC AAC TGT GAG CGT ACC TTC ATT GCG |
| HNM$_2$-3' (60 nts) | 16 | CCG CAT ATG TCA CGG CGC CAG CGG CAG CAC CAG CGC TTC ATA GAT CCA GTT CTG AGC ACA |
| HM$_3$N-5' (63 nts) | 17 | CCG CAT ATG GCG GTG GCG CTG CTG ATT CTG GCG GTG GCC AAC TGT GAG CGT ACC TTC ATT GCG |
| HNM$_3$-3' (63 nts) | 18 | CCG CAT ATG TCA CAC CGC CAG AAT CAG CAG CGC CAC CGC TTC ATA GAT CCA GTT CTG AGC ACA |

Figure 2A:
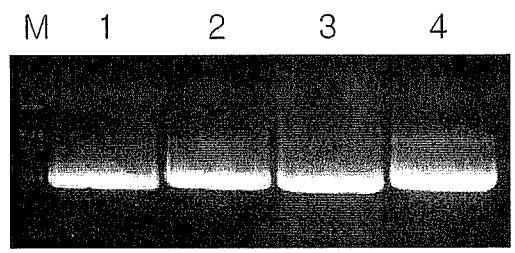
FIG. 2a is a photograph of an agarose gel electrophoresis analysis showing PCR-amplified DNA fragments encoding cell permeable Nm23 recombinant proteins being fused to a kFGF4-derived MTD and constructed in the full-length forms according to the present invention.
Figure 2B:
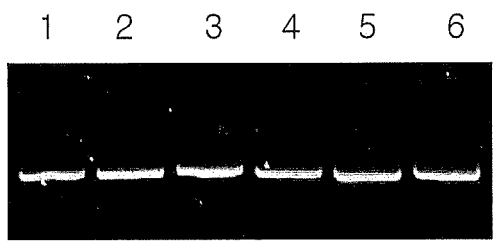
FIG. 2b is a photograph of an agarose gel electrophoresis analysis showing PCR-amplified DNA fragments encoding cell permeable Nm23 recombinant proteins being fused to each of JO-76 and JO-77 MTDs and constructed in the full-length forms according to the present invention.

The PCR was performed in a 50 μl reaction mixture containing 100 ng of human Nm23 cDNA as a template, 0.2 mM dNTP mixture (dGTP, dATP, dTTP, and dCTP, each at 2 mM), 0.6 μM of each primer, 5 of 10×Taq buffer, 1 μl of Taq polymerase (TAKARA, Japan). The PCR was performed for 25 cycles at 94° C. for 45 seconds, at 53° C. for 45 seconds and at 72° C. for 45 seconds after the initial denaturation of 94° C. for 2 minutes, followed by the final extension at 72° C. for 5 minutes. After the PCR was completed, the amplified PCR product was digested with restriction enzyme NdeI and loaded onto a 1.0% agarose gel and fractionated. As shown in FIGS. 2a and 2b, it was confirmed that the expected fragment for each recombinant construct fused to one of a kFGF4-derived MTD, a JO-76 MTD and a JO-77 MTD was successfully amplified.

Figure 3A:
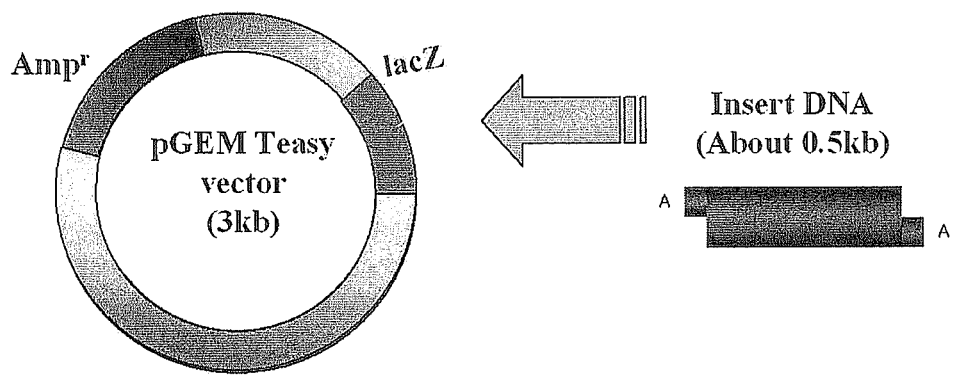
FIG. 3a is a schematic diagram illustrating the subcloning of a PCR product encoding a cell permeable Nm23 recombinant protein into the pGEM-T Easy vector according to the present invention.

The DNA band of expected size was excised from the gel, eluted, and purified by using a QIAquick™ Gel extraction kit (QIAGEN, USA). The eluted DNA was precipitated with ethanol and resuspended in distilled water for ligation. As shown in FIG. 3a, the PCR amplified DNA fragment containing the coding region was subcloned into a pGEM-T Easy vector (PROMEGA, Madison Wis. USA) with a T4 ligase according to the TA cloning method, and then, followed by transformation of E. coli DH5α competent cells with the pGEM-T Easy vector. The cells were plated onto LB plate media supplemented with 50 μg/ml of ampicillin and cultured at 37° C. for overnight. After the recombinant fragment-inserted pGEM-T Easy vector was isolated by treating with restriction enzyme NdeI 37° C. for 1 hour, it was subjected to a 0.8% agarose gel electrophoresis.

Figure 3B:
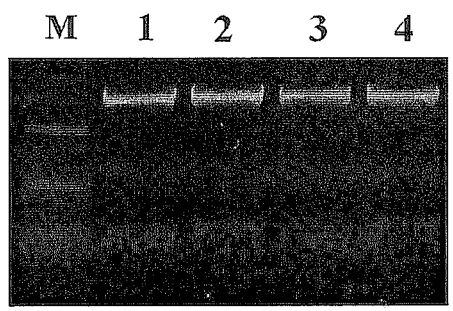
FIGS. 3b and 3c are photographs of an agarose gel electrophoresis analysis showing the PCR products encoding the cell permeable Nm23 recombinant proteins from FIGS. 2a and 2b subcloned in the pGEM-T Easy vector according to the present invention, respectively.
Figure 3C:
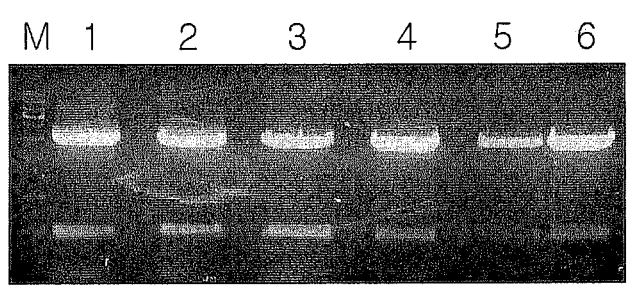

As shown in FIG. 3b, the DNA fragments of about 0.5 kb for the full-length forms and vector fragments of about 3 kb were detected, confirming that the insert DNA of the CP-Nm23 recombinant construct was appropriately subcloned into the pGEM-T Easy vector.

Figure 4A:
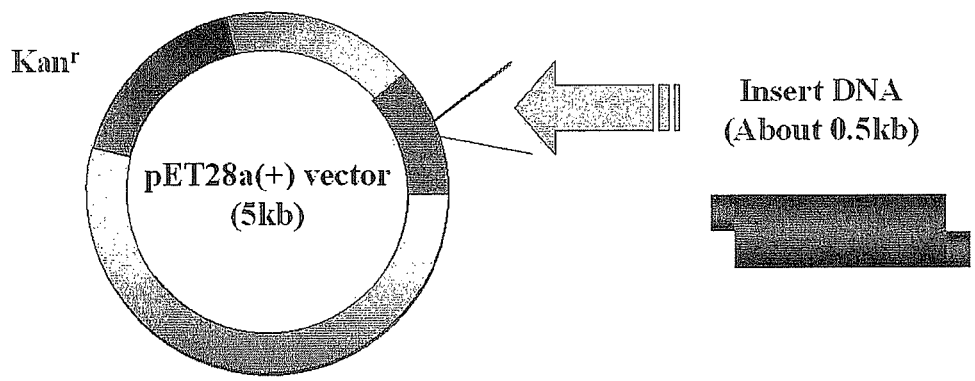
FIG. 4a is a schematic diagram illustrating the cloning of a recombinant DNA fragment encoding a cell permeable Nm23 recombinant protein into the pET 28(+) vector according to the present invention.

A pET-28(+)a vector (NOVAGEN, Madison, Wis.) bearing a histidine-tag and a T7 promoter was digested with a restriction enzyme NdeI ( ENZYNOMICS, Korea). The pGEM-T Easy vector fragments containing the CP-Nm23 recombinant fragment and pET-28(+)a vector fragment were purified by using a QIAquick™ Gel extraction kit. Each of the pGEM-T Easy vector fragments was cloned into the pre-treated pET-28a(+) with a T4 ligase at 16° C. for 12 hours, followed by transformation of E. coli DH5α competent cells with the resulting pET-28a(+) vector (FIG. 4a).

Figure 4B:
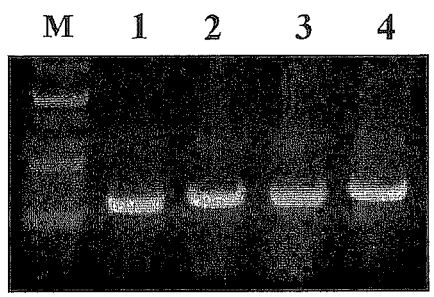
FIGS. 4b and 4c are photographs of an agarose gel electrophoresis analysis showing the recombinant DNA fragments encoding the cell permeable Nm23 recombinant proteins subcloned in the pET 28(+) vector according to the present invention.
Figure 4C:
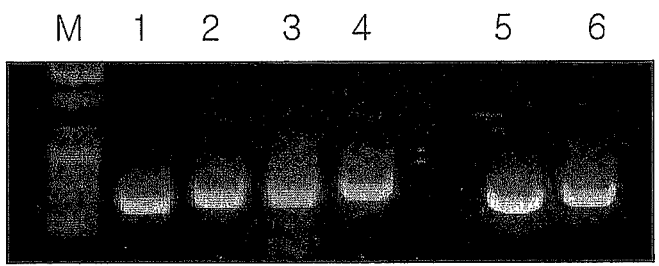

After the clones were treated with the restriction enzyme NdeI (Enzynomics, Korea) and subjected to 0.8% agarose gel electrophoresis, it was verified that DNA fragments of about 0.5 kb for the full-length forms and vector fragments of about 5 kb were detected, confirming the cloning of the insert DNA of CP-Nm23 recombinant construct into pET-28a(+) vector, as shown in FIG. 4b.

The successfully cloned expression vectors for expressing cell permeable Nm23 recombinant proteins were designated pET28a(+)-HM$_1$N, pET28a(+)-HNM$_1$, pET28a(+)-HM$_1$NM$_1$, pET28a(+)-HM$_2$N, pET28a(+)-HNM$_2$, pET28a(+)-HM$_3$N, pET28a(+)-HNM$_3$ and pET28a(+)-HM$_3$NM$_3$, respectively. Among them, the E. coli transformants DH5α/HM$_3$Nm23 and DH5α/HNm23M$_3$ obtained by transforming E. coli DH5α with the expression vectors pET28a(+)-HM$_3$N and pET28a(+)-HNM$_3$, respectively, were deposited on Aug. 28, 2008 in accordance with the Budapest Treaty under accession numbers KCTC-11380BP and KCTC-11381BP with the Korean Collection for Type Cultures (KCTC), Korea Research Institute of Bioscience and Biotechnology (KRIBB), 52, Oun-Dong, Yusong-Ku, Taejon 305-333, Republic of Korea.

The results of sequencing analysis are as follows:

As for the full-length forms of the cell permeable Nm23 recombinant protein constructed by using a kFGF4-derived MTD, His-MTD$_1$-Nm23 (HM$_1$N) has an amino acid sequence represented by SEQ ID NO: 22, while a polynucleotide encoding the same has a nucleotide sequence represented by SEQ ID NO: 21; His-Nm23-MTD$_1$ (HNM$_1$) has an amino acid sequence represented by SEQ ID NO: 24, while a polynucleotide encoding the same has a nucleotide sequence represented by SEQ ID NO: 23; and His-MTD$_1$-Nm23-MTD$_1$ (HM$_1$NM$_1$) has an amino acid sequence represented by SEQ ID NO: 26, while a polynucleotide encoding the same has a nucleotide sequence represented by SEQ ID NO: 25.

As for the full-length forms of the cell permeable Nm23 recombinant protein constructed by using a JO-76 MTD, His-MTD$_2$-Nm23 (HM$_2$N) has an amino acid sequence represented by SEQ ID NO: 28, while a polynucleotide encoding the same has a nucleotide sequence represented by SEQ ID NO: 27; and His-Nm23-MTD$_2$ (HNM$_2$) has an amino acid sequence represented by SEQ ID NO: 30, while a polynucleotide encoding the same has a nucleotide sequence represented by SEQ ID NO: 29.

As for the full-length forms of the cell permeable Nm23 recombinant protein constructed by using a JO-77 MTD as described above, His-MTD$_3$-Nm23 (HM$_3$N) has an amino acid sequence represented by SEQ ID NO: 32, while a polynucleotide encoding the same has a nucleotide sequence represented by SEQ ID NO: 31; His-Nm23-MTD$_3$ (HNM$_3$) has an amino acid sequence represented by SEQ ID NO: 34, while a polynucleotide encoding the same has a nucleotide sequence represented by SEQ ID NO: 33; and His-MTD$_3$-Nm23-MTD$_3$ (HM$_3$NM$_3$) has an amino acid sequence represented by SEQ ID NO: 36, while a polynucleotide encoding the same has a nucleotide sequence represented by SEQ ID NO: 35.

As a control for the cell permeable Nm23 recombinant proteins, His-Nm23 (HN), where a full-length Nm23 is fused only to a nuclear localization sequence (NLS) derived from SV40 large T antigen and a histidine-tag (His-Tag) without any MTD, was constructed. The control protein has an amino acid sequence represented by SEQ ID NO: 20, while a polynucleotide encoding the same has a nucleotide sequence represented by SEQ ID NO: 19.

Example 2

Expression of Recombinant Proteins

<2-1>Selection of Optimal Bacterial Strains

To select the optimal bacterial strain for the expression of cell permeable Nm23 recombinant proteins prepared in Example 1 above, the following experiments were carried out in *E. coli* BL21(DE3), BL21-Gold(DE3), BL21-CodonPlus (DE3) and BL21-Gold(DE3) pLysS strains (STRATAGENE, USA), all of which contain the LacI promoter.

First, each of the expression vectors pET28a(+)-HM$_1$N, pET28a(+)-HNM$_1$, pET28a(+)-HM$_1$NM$_1$, and pHN (control) was transformed into *E. coli* BL21(DE3), BL21-Gold (DE3), BL21-CodonPlus(DE3) and BL21-Gold(DE3) pLysS strains, respectively, according to the heat shock method. Further, each of the expression vectors pET28a(+)-HM$_2$N, pET28a(+)-HNM$_2$, pET28a(+)-HM$_3$N, pET28a(+)-HNM$_3$ and pET28a(+)-HM$_3$NM$_3$ was transformed into *E. coli* BL21-Gold(DE3) strain, respectively, according to the heat shock method. After the transformation, the cells were cultured in an LB agar plate containing 50 μg/ml of kanamycin. Colonies formed on the plate were grown in 1 in of LB medium at 37° C. overnight, followed by culturing at 37° C. in 100 μl of LB medium with vigorous shaking until the optical density 600 (OD$_{600}$) reached 0.5. IPTG (isopropyl-β-D-thiogalactoside) was then added thereto at a final concentration of 0.7 mM to induce the expression of the CP-Nm23 recombinant proteins. Protein induction was prolonged for 2 hours at 30° C. The *E. coli* culture solutions were harvested by centrifugation at 4° C., 7,000×g for 20 minutes, resuspended in a lysis buffer (100 mM NaH$_2$PO$_4$, 10 mM Tris-HCl, 8 M urea, pH 8.0), and subjected to ultrasonication on ice using a sonicator equipped with a probe. The cell lysates were centrifuged at 14,000×g for 15 minutes, so as to separate an insoluble fraction from a soluble fraction. The thus obtained soluble and insoluble fractions of CP-Nm23 recombinant proteins expressed in the *E. coli* strain with IPTG were loaded on a SDS-PAGE gel.

Figure 5:
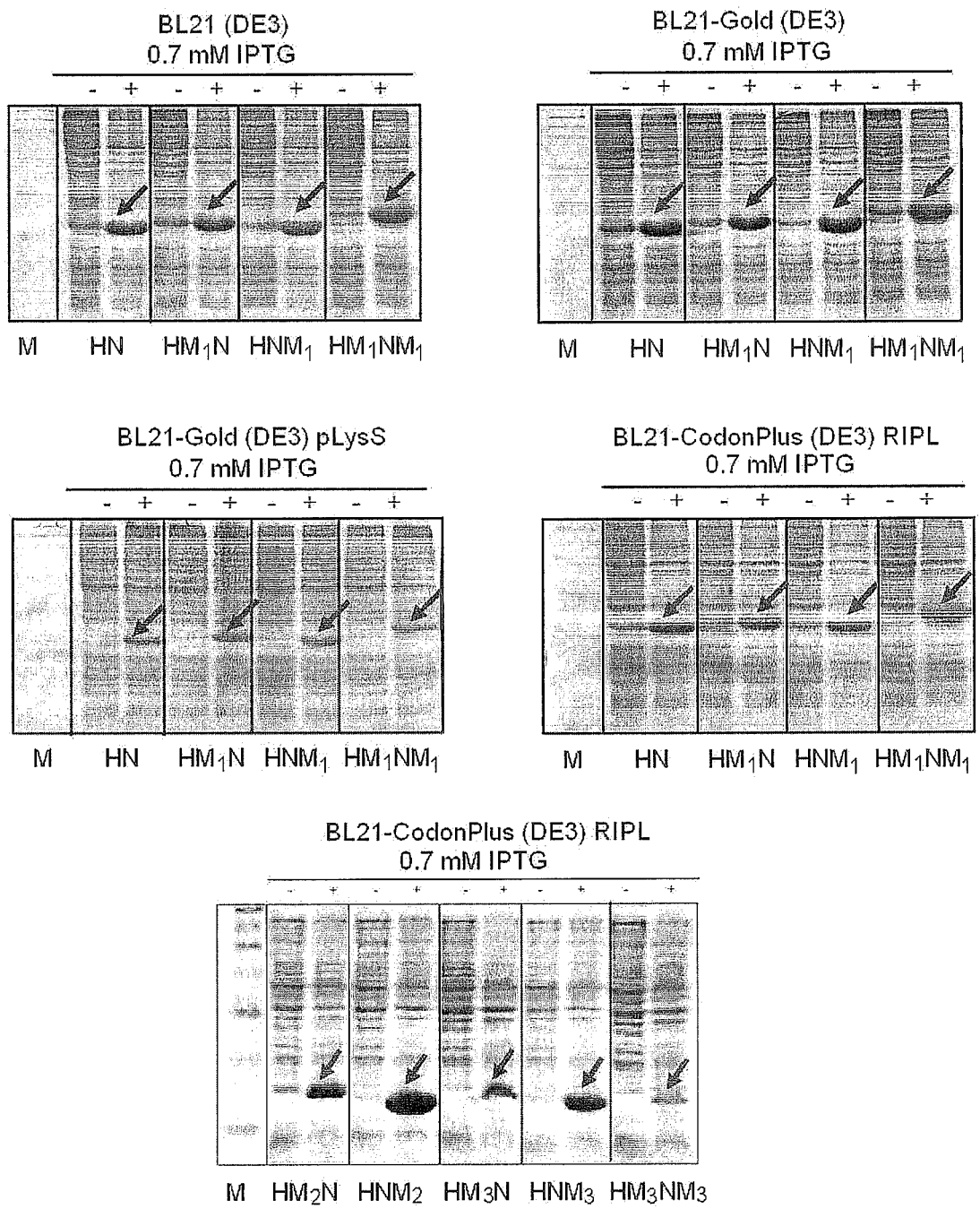
FIG. 5 is a photograph of a SDS-PAGE analysis showing the inducible expression of cell permeable Nm23 recombinant proteins according to the present invention in various kinds of host cells.

As shown in FIG. 5, although some cell permeable Nm23 recombinant proteins were expressed at a relatively low level in BL21-Gold (DE3), most cell permeable Nm23 recombinant proteins showed the highest expression level in the strain. According to these results, BL21-Gold (DE3) was selected as the optimal strain for the expression of the cell permeable Nm23 recombinant proteins according to the present invention.

<2-2>Expression of Recombinant Proteins

Each of the expression vectors pET28a(+)-HM$_1$N, pET28a (+)-HNM$_1$, pET28a(+)-HM$_1$NM$_1$, pET28a(+)-HM$_2$N, pET28a(+)-HNM$_2$, pET28a(+)-HM$_3$N, pET28a(+)-HNM$_3$ and pET28a(+)-HM$_3$NM$_3$ was transformed into *E. coli* BL21-Gold(DE3), selected as the optimal strain in section <2-1> of Example 2 above, followed by inducing their expression through the addition of 0.7 mM IPTG, according to the same method described in section <2-1> of Example 2. After that, soluble and insoluble fractions of CP-Nm23 recombinant proteins obtained therefrom were loaded on a SDS-PAGE gel.

Figure 6:
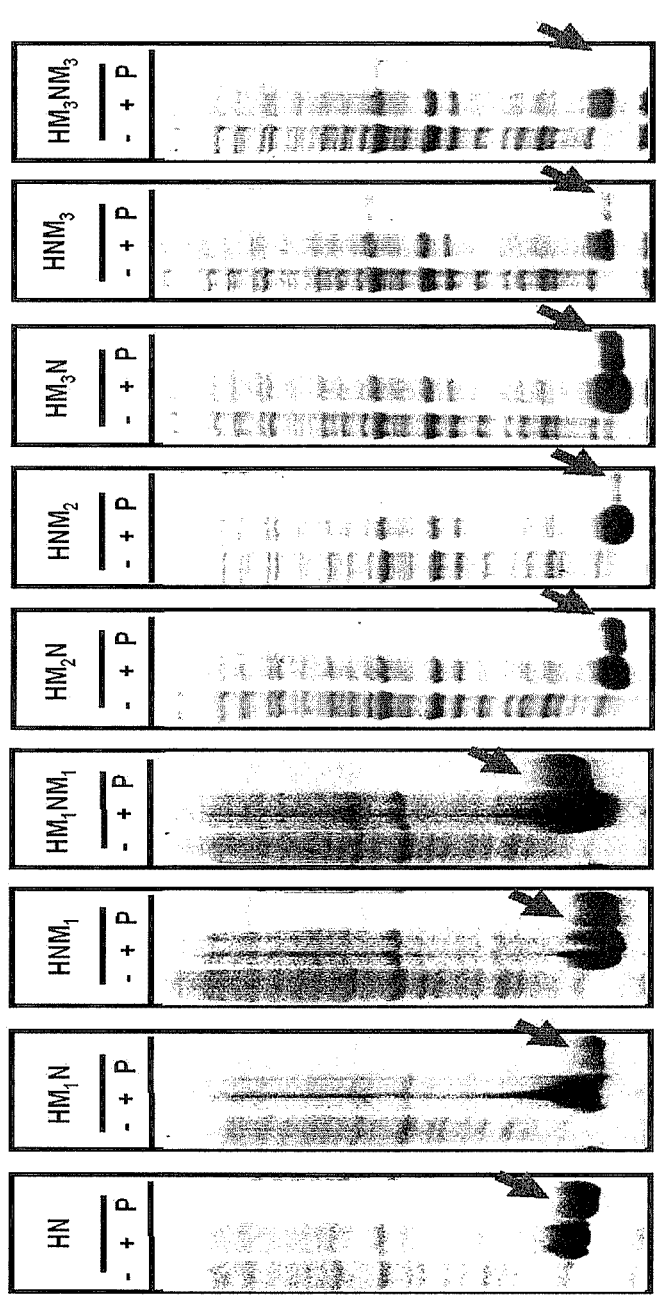
FIG. 6 is a photograph of a SDS-PAGE analysis showing the purification of cell permeable Nm23 recombinant proteins expressed from the transformants where the expression vector according to the present invention is transformed into.

As shown in FIG. 6, it was confirmed that the cell permeable Nm23 recombinant proteins (19 to 20 kDa) expressed in the host cell were mostly included in the insoluble fraction as an inclusion body, and their expression was significantly increased in the presence of IPTG.

Example 3

Purification and Refolding of Recombinant Proteins

<3-1>Purification of Recombinant Proteins

The inducible expression of cell permeable Nm23 recombinant proteins in an *E. coli* system leads to the formation of insoluble aggregates, which are known as inclusion bodies. To completely solubilize these inclusion bodies, all of the above expressed proteins were denatured by dissolving them in 8 M urea used as a strong denaturing agent.

First, the BL21 Gold(DE3) strains transformed with each of the expression vectors pET28a(+)-HM$_1$N, pET28a(+)-HNM$_1$, pET28a(+)-HM$_1$NM$_1$, pET28a(+)-HM$_2$N, pET28a (+)-HNM$_2$, pET28a(+)-HM$_3$N, pET28a(+)-HNM$_3$, pET28a (+)-HM$_3$NM$_3$ and pET28a(+)-HM (control) were cultured in 1 l of an LB medium as described in Example 2. Each culture solution was harvested by centrifugation, gently resuspended in 20 of a lysis buffer (HN and HNM$_1$: 50 mM NaH$_2$PO$_4$, 300 mM NaCl, 10 mM imidazole, pH 8.0; other CP-Nm23: 100 mM NaH$_2$PO$_4$, 10 mM Tris-HCl, 8 M urea, pH 8.0) without forming bubbles, and subjected to ultrasonication on ice using a sonicator equipped with a microtip. The cells were intermittently sonicated for 30 seconds, followed by cooling for 10 seconds, while setting the power to 25% of the maximum power. The total sonication time was 5 minutes. The cell lysates were centrifuged at 4° C., 4,000×g for 20 minutes, so as to separate the supernatant and the cellular debris pellet. The supernatant was loaded onto a Ni-NTA agarose resin where nitrilotriacetic acid agarose was charged with nickel (Ni). The Ni-NTA agarose resin was equilibrated with the lysis buffer. The supernatant was allowed to absorb onto the resin by gently shaking (using a rotary shaker) at 4° C. for 8 hours or more. The resin absorbed with the inclusion bodies containing the recombinant protein was centrifuged at 4° C., 1,000×g for 5 minutes, to remove the reaction solution and washed with a washing buffer (HN and HNM$_1$: 50 mM NaH$_2$PO$_4$, 300 mM NaCl, 10 mM imidazole, pH 6.3; other CP-Nm23: 100 mM NaH$_2$PO$_4$, 10 mM Tris-HCl, 8 M urea, pH 6.3) five times to remove nonspecific absorbed materials. After washing, the proteins absorbed to the resin were eluted with an elution buffer (HN and HNM$_1$: 50 mM NaH$_2$PO$_4$, 300 mM NaCl, 10 mM imidazole, pH 4.5; other CP-Nm23: 100 mM NaH$_2$PO$_4$, 10 mM Tris-HCl, 8 M urea, pH 4.5) with stirring for 2 hours or more under acidic conditions of pH 4.5. The eluted proteins were analyzed with 12% SDS-PAGE gel electrophoresis, stained with Coomassie Brilliant Blue R by gently shaking, and destained with a destaining solution.

According to the results shown in FIG. 6, all of the cell permeable Nm23 recombinant proteins fused to a kFGF4-derived MTD, a JO-76 MTD and a JO-77 MTD, respectively, were detected as a single band corresponding to about 19 to 20 kDa, which confirms that the cell permeable Nm23 recombinant proteins of the present invention have been purified from the insoluble fraction.

<3-2> Refolding of Recombinant Proteins

Since the cell permeable Nm23 recombinant proteins of the present invention purified from the insoluble fraction as described in section <3-1> of Example 3 above were denatured by a strong denaturing agent, such as 8 M urea, the denatured proteins must be converted into an active form by a refolding process, as follows.

First, the purified recombinant proteins were subjected to a refolding process by dialyzing them against a refolding buffer (0.55 M guanidine HCl, 0.88 M L-arginine, 50 mM Tris-HCl, 150 mM NaCl, 1 mM EDTA, 100 mM NDSB, 1 mM glutathione oxidized, and 1 mM glutathione reduced) at 4° C. for 24 hours, thereby removing the denaturing agent. All of the refolded recombinant proteins were dialyzed against a cell culture medium DMEM (Dulbecco's Modified Eagle Medium) by using a dialysis bag (Snakeskin pleated, PIERCE) at 4° C. for 10 hours while stirring. The medium was replaced with fresh DMEM every 3 hours. The cell permeable Nm23 recombinant proteins of the present invention converted into their active form through the refolding process were used in the following experiments.

Example 4

Quantitative Cell Permeability Analysis of Nm23 Recombinant Proteins

In order to quantitatively determine the cell permeability of the cell permeable Nm23 recombinant proteins according to the present invention, the introduction of the proteins into the cell was analyzed by FACS (fluorescence-activated cell sorting) in an animal model, as follows.

The cell permeable Nm23 recombinant proteins refolded into their active form in section <3-2> of Example 3 above were labeled with FITC (fluorescein-5-isothiocyanate, MOLECULAR PROBE). The recombinant protein (2 to 20 mg) was mixed with 1 µl of FITC at a concentration of 333 mg/ml and reacted in a dark room at room temperature for 1 hour with gentle stirring. The reaction solution was subjected to a dialysis against DMEM at 4° C. for 2 days until the unreacted FITC was completely removed, thereby obtaining FITC-conjugated recombinant proteins. Thus obtained FITC-conjugated recombinant proteins were subjected to a Bradford protein assay to measure the protein concentration. As a result, each of the FITC-conjugated recombinant proteins was measured to have a concentration of about 0.7 µg/µl.

Meanwhile, RAW 264.7 cells derived from mouse macrophage were maintained in DMEM supplemented with 10% fetal bovine serum and 1% penicillin/streptomycin (500 mg/ml) and incubated at 37° C. in a humidified atmosphere of 5% $CO_2$ in air.

After the incubation, the cells were treated with 10 µM of each of the FITC-conjugated recombinant proteins ($HM_1N$, $HNM_1$, $HM_1NM_1$, $HM_3N$, $HNM_3$ and $HM_3NM_3$) prepared above, followed by further culturing them for 1 hour at 37° C. Subsequently, the cells were treated with trypsin/EDTA (T/E, INVITROGEN) to remove cell surface bound proteins, washed with cold PBS (phosphate buffered saline) three times, and then, subjected to flow cytometry analysis by using a CELLQUEST PRO software program of the FACS (fluorescence-activated cell sorting) Calibur system (BECKTON-DICKINSON). The cell concentration of each sample was $1 \times 10^4$ cells/µl, and the analysis was performed twice or more. The cell permeability of the cell permeable Nm23 recombinant proteins according to the present invention was determined by comparing it to that of the control protein (HN) not fused to a MTD.

Figure 7A:
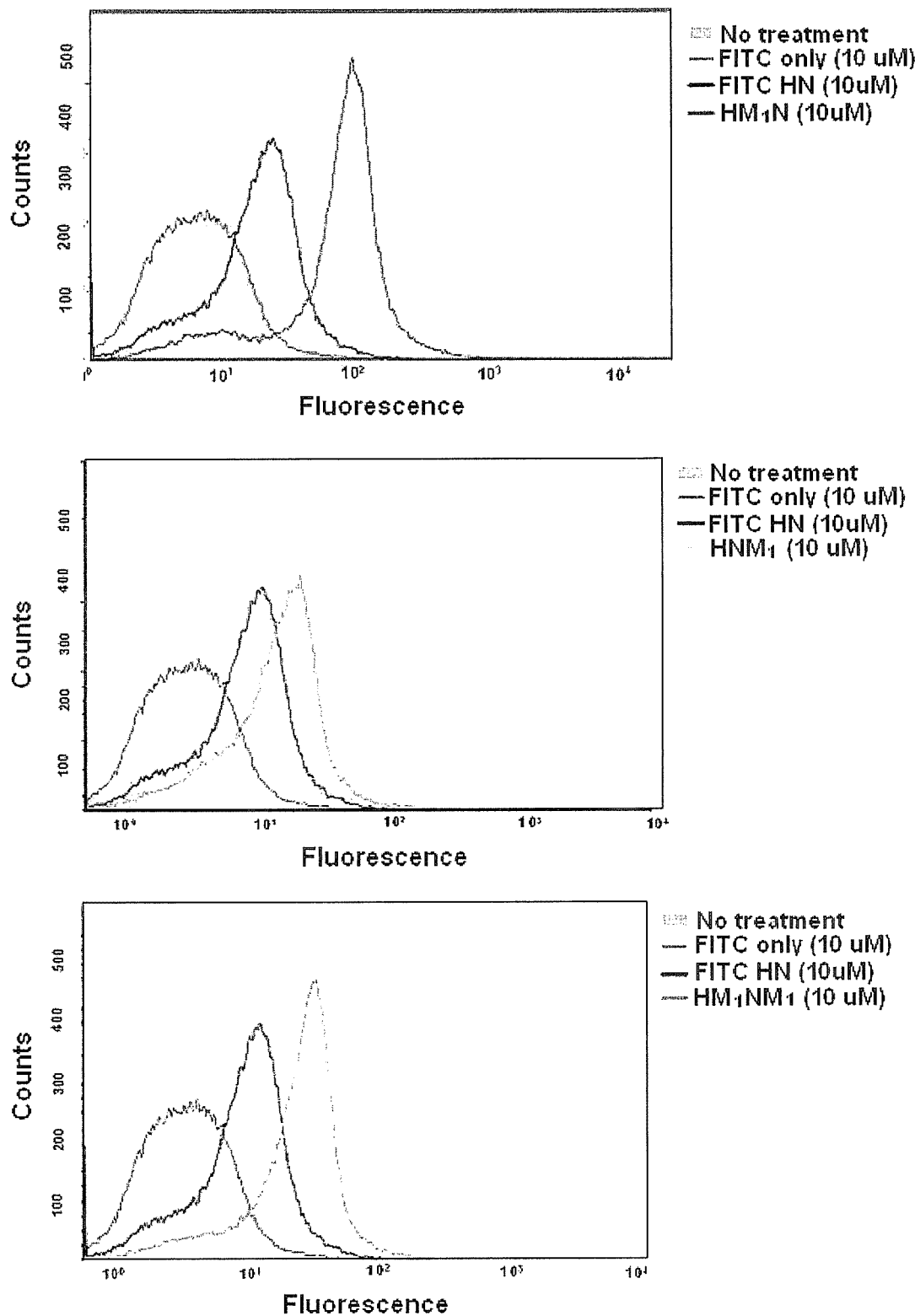
FIGS. 7a and 7b are graphs illustrating the results of flow cytometry analysis of cell permeabilities of cell permeable Nm23 recombinant proteins according to the present invention.
Figure 7B:
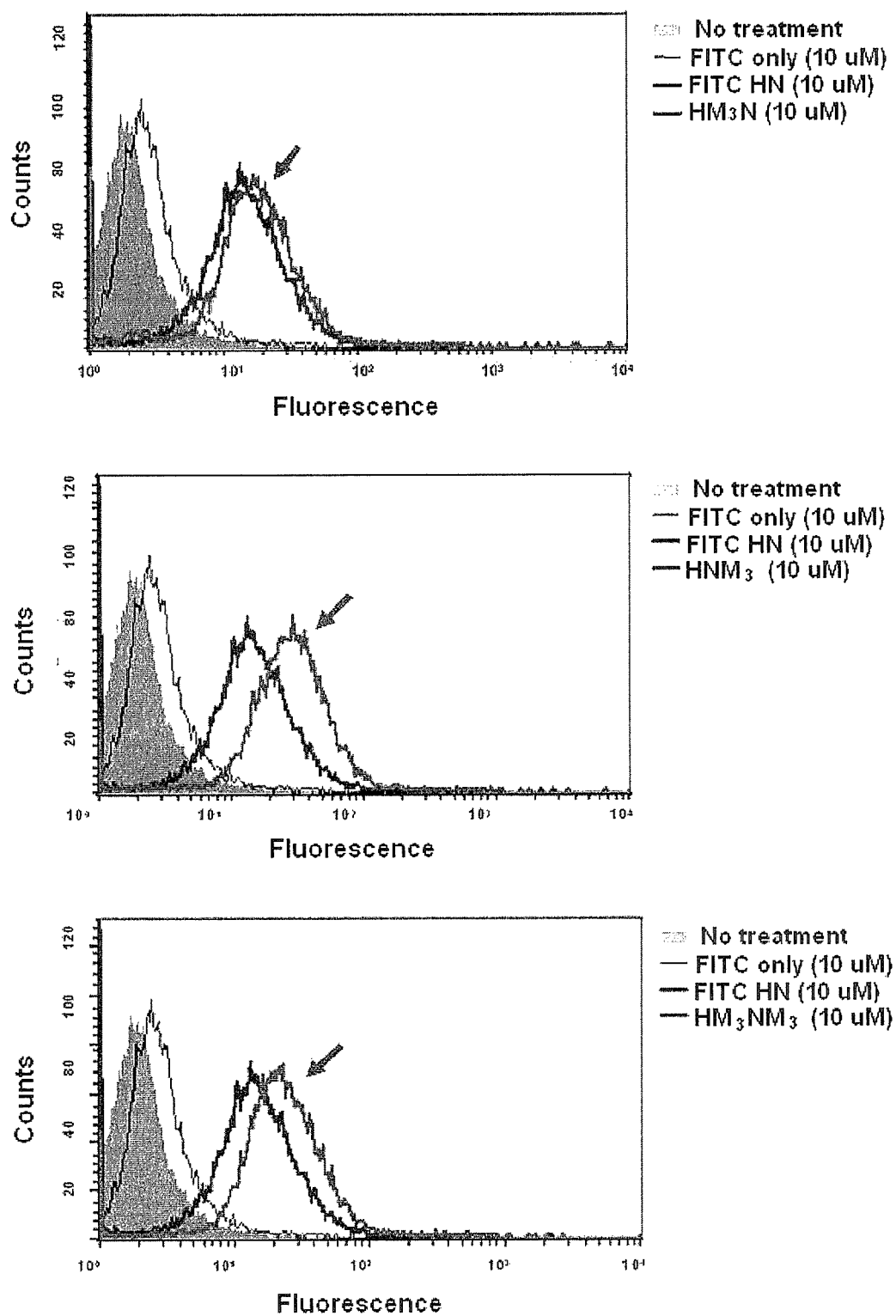

FIGS. 7a and 7b show the results of the flow cytometry analysis where the gray filled curve represents cell only, the black curve represents FITC only, the blue curve represents the cell permeability of the control protein not fused to a MTD (HN), the red curve represents the cell permeability of the cell permeable recombinant proteins $HM_1N$, $HM_3N$, $HNM_3$ and $HM_3NM_3$, the green curve represents the cell permeability of the cell permeable recombinant protein $HNM_1$, and the orange curve represents the cell permeability of the cell permeable recombinant protein $HM_1NM_1$. Referring to the results shown in FIGS. 7a and 7b, it was found that all of the cell permeable Nm23 recombinant proteins showed significantly higher cell permeability than the control protein.

Example 5

Microscopic Cell Permeability Analysis of Nm23 Recombinant Proteins

To visualize the intracellular localization of human Nm23 proteins delivered into a cell, NIH 3T3 cells (Korean Cell Line Bank, Seoul, Republic of Korea) were treated with FITC-conjugated recombinant proteins ($HM_1N$, $HNM_1$, $HM_1NM_1$, $HM_2N$, $HNM_2$, $HM_3N$, $HNM_3$ and $HM_3NM_3$) and visualized by confocal laser scanning microscopy.

First, the NIH 3T3 cells were cultured in an 8-well chamber slide (LabTek, Nalgen Nunc) for 24 hours. The NIH3T3 cells were maintained in DMEM supplemented with 10% fetal bovine serum, 5% penicillin/streptomycin (500 mg/ml) in 5% $CO_2$ at 37° C. After the cells were washed with PBS three times, the cells were treated with serum-free DMEM, serum-free DMEM containing FITC, and serum-free DMEM containing 10 µM of each of FITC-conjugated recombinant proteins, respectively, in 5% $CO_2$ at 37° C. One hour later, the cells were fixed with 4% paraformaldehyde at room temperature for 20 minutes.

For a direct detection of FITC-conjugated recombinant proteins that were internalized, the cells were washed with PBS three times and counterstained with a nuclear fluorescent stain solution, propidium iodide (PI, SIGMA-ALDRICH). The cells were stained with PI at a concentration of 1 µg/ml for 5 minutes, followed by washing with PBS three times. In order to preserve the FITC fluorescence of the recombinant protein, the glass slide was fixed in 10 µl of a polyvinyl alcohol mounting medium containing DABCO (Fluca) for 15 minutes before the observation. The intracellular distribution of the fluorescence was determined at the middle of a single cell analyzed by a confocal laser scanning microscope using a normaski filter. The confocal laser scanning microscopy was employed for observing cell phormology, FITC fluorescence and PI fluorescence. FITC was excited at 488 nm and detected by means of a bandpass filter at 530 nm.

Figure 8A:
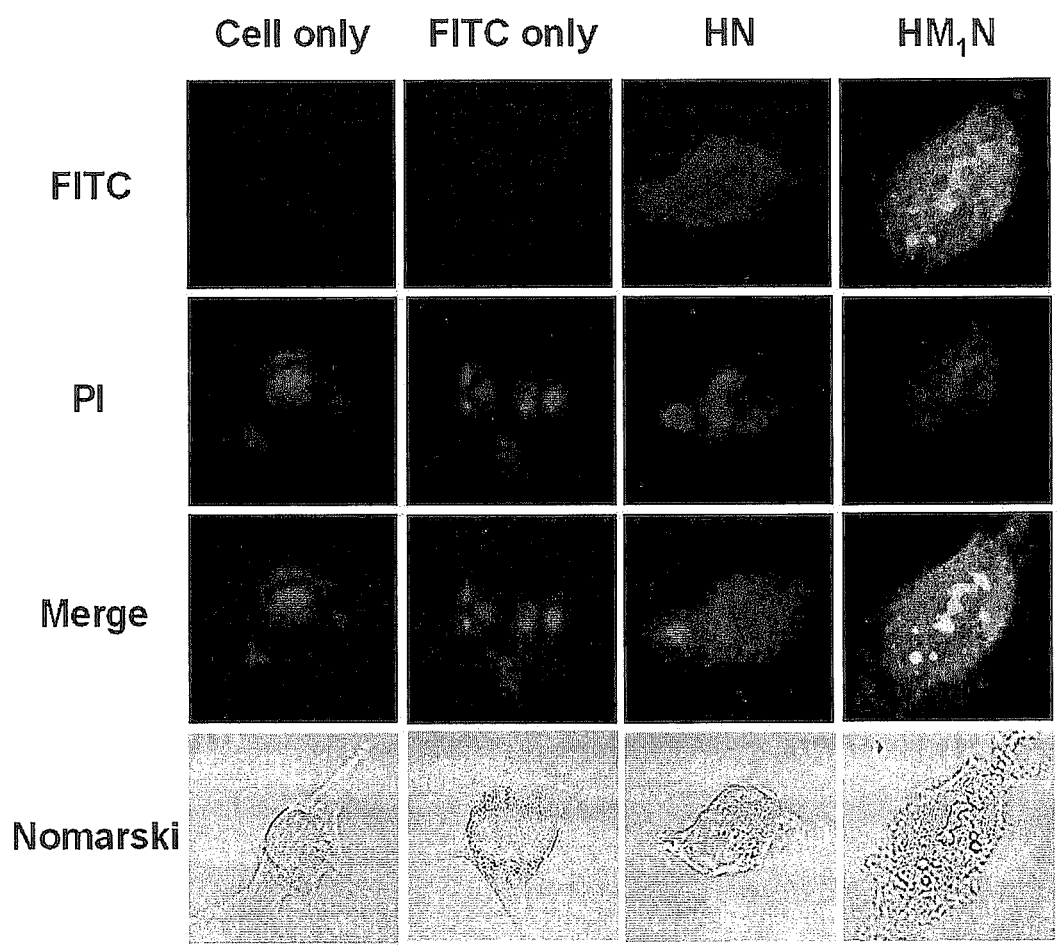
FIGS. 8a to 8c are confocal laser scanning microscopy photographs visualizing the cell permeabilities of cell permeable Nm23 recombinant proteins according to the present invention in mouse fibroblasts.
Figure 8B:
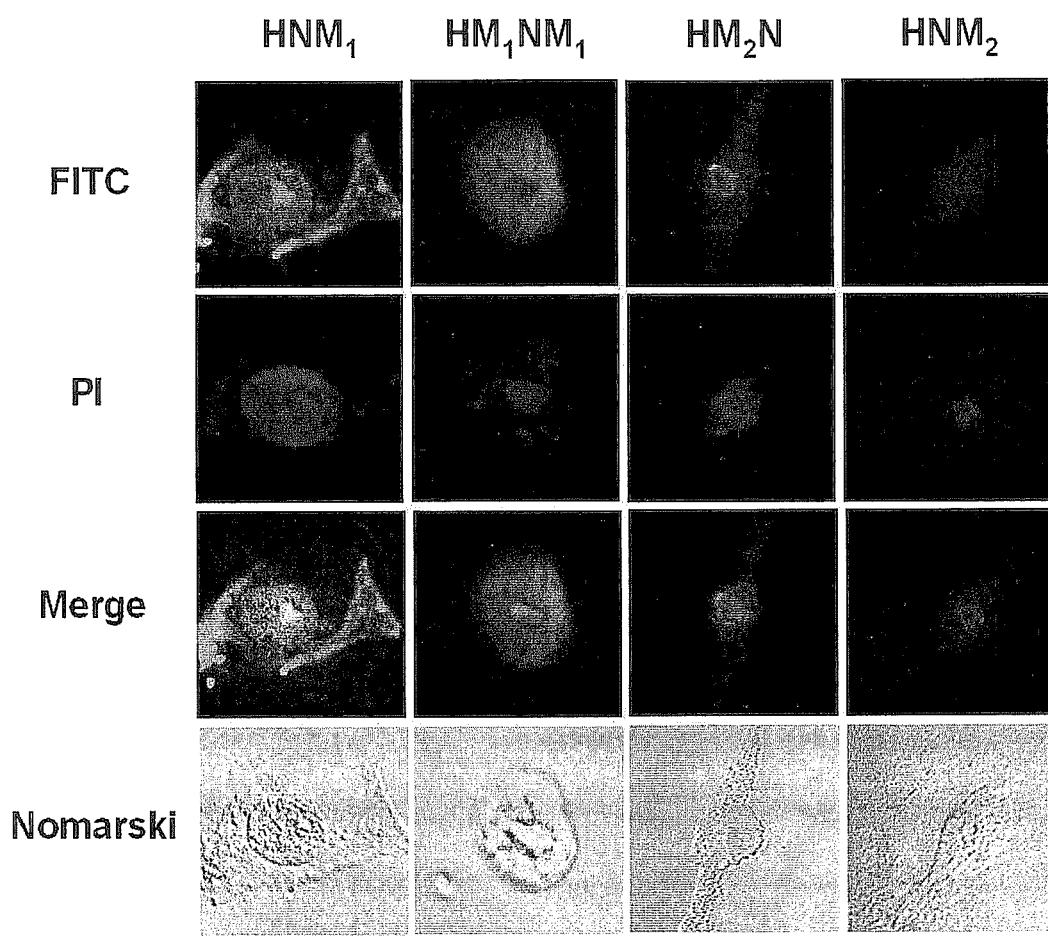
Figure 8C:
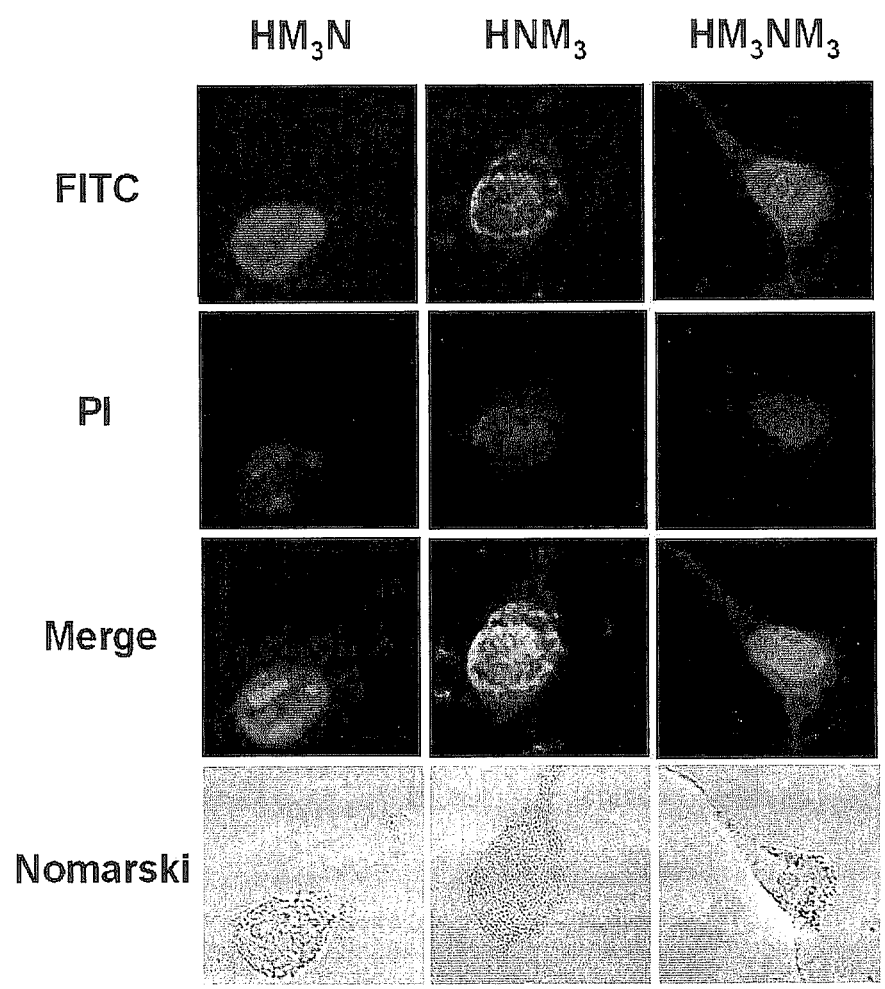

As shown in FIGS. 8a to 8c, it was observed that the cell permeable Nm23 recombinant proteins stained with FITC and PI were well distributed largely in the nucleus as compared with the cell only, FITC only and MTD-lacking control protein. The intracellular localization of the cell permeable Nm23 recombinant proteins fused to one of a kFGF4-derived MTD, a JO-76 MTD and a JO-77 MTD according to the present invention was consistent with the cell permeability of the same determined by flow cytometry above. From these results, it was confirmed that the cell permeable Nm23 recombinant proteins of the present invention exhibited high cell permeability.

Example 6

Inhibitory Effect of Cell Permeable Nm23 Recombinant Proteins on MAPK Signal Transduction In order to confirm the in vivo function of the cell permeable Nm23 recombinant proteins according to the present invention, the biochemical functions of the recombinant proteins were examined on three types of cancer cell lines by Western blot analysis.

MDA-MB-435 and MDA-MB-231 cells, the highly metastatic human breast cancer cell lines used in this experiment, were purchased from Korean Cell Line Bank (Seoul, Republic of Korea). The cell lines were maintained in a RPMI 1640 medium (L-glutamine 300 mg/l, 25 mM HEPES and 25 mM $NaHCO_3$) supplemented with 10% FBS and 1% penicillin/streptomycin in a 5% $CO_2$ incubator at 37° C. CCL-185 cells, a human lung cancer cell line, were obtained from ATCC and maintained in a HamF-12K medium (2 mM L-glutamine, 1500 mg/f sodium bicarbonate) supplemented with 10% FBS and 1% penicillin/streptomycin in a 5% $CO_2$ incubator at 37° C.

After 2 ml of the RPMI 1640 medium supplemented with FBS was added to each well of a 6-well plate, MDA-MB-435, MDA-MB-231, and CCL-185 cells were inoculated thereto at a concentration of $5 \times 10^6$ cells/ml. The well plate was incubated at 37° C. for 1 day so as to allow the cells to grow while adhering to the well plate. After removing the medium, the cells adhered to the well plate were washed with cold PBS. Subsequently, the cells were treated with 500 µl of each of the cell permeable Nm23 recombinant proteins and MTD-lacking Nm23 control protein (HIN) at a concentration of 10 µM, and reacted in a 5% $CO_2$ incubator at 37° C. for 1 hour. The MDA-MB-435 cells were treated with each of $HM_1N$, $HNM_1$, $HM_1NM_1$, $HM_2N$, $HNM_2$, $HM_3N$, $HNM_3$ and $HM_3NM_3$ recombinant proteins, while MDA-MB-231 and CCL-185 cells were treated with each of $HM_3N$, $HNM_3$ and $HM_3NM_3$ recombinant proteins. After the reaction was completed, the cells were washed twice with PBS, and then, cultured in the presence of serum under the same conditions noted above for 2, 4, 6 and 8 hours, respectively.

After the cultivation was completed, the cells were resuspended in 200 µl of a lysis buffer (20 mM HEPES, pH 7.2, 1% Triton-X, 10% glycerol and proteinase inhibitor) and subjected to ultrasonication on ice for 30 minutes, to thereby obtain a cell lysate. The cell lysate was centrifuged at 12,000 rpm for 20 minutes at 4° C. to separate the supernatant. The thus obtained supernatant was subjected to a Bradford protein assay to quantitatively measure the protein concentration. The recombinant protein was resuspended in a SDS-PAGE loading buffer at a concentration of 25 µM to prepare a cell lysate sample. The thus prepared cell lysate sample was heated at 90° C. for 5 minutes, and then, stored at −80° C. until use.

For the Western blot analysis, p21 (21 kDa, CELL SIGNALING TECHNOLOGY), phospho-p53 (Ser15, 53 kDa, Cell Signaling), phospho-MEK (Ser217/221, 45 kDa, CELL SIGNALING TECHNOLOGY), and phospho-Erk (Thr202/Tyr204, 42/44 kDa, CELL SIGNALING TECHNOLOGY) were used as primary antibodies, and goat anti-mouse IgG-HRP (SANTA CRUZ BIOTECHNOLOGY) and goat anti-rabbit IgG-HRP (SANTA CRUZ BIOTECHNOLOGY) were used as secondary antibodies. The cell lysate sample was applied to a 12% SDS-PAGE at 100 V for 2 hours and transferred onto a polyvinylidene fluoride (PDVF) membrane at 100 V for 90 minutes. In order to prevent the nonspecific interaction between the blotted proteins and unrelated antibodies, the PVDF membrane was blocked with 5% non-fat dry milk in TBS/T (10 Mm Tris-Cl, pH 8.0, 150 mM NaCl, 0.05% Tween 20) at room temperature for 1 hour. After removing the blocking buffer, the PVDF membrane was washed with TBS/T, followed by incubation with each of the primary antibodies (diluted with the freshly prepared blocking buffer at a ratio of 1:10000) for 1 hour at 4° C. After removing the primary antibody solution, the membrane was washed with TBS/T five times each for 5 minutes, and incubated with the secondary antibody (diluted with the freshly prepared blocking buffer at a ratio of 1:5000) for 1 hour at room temperature. After washing with TBS/T five times, the membrane was stained using an enhanced chemiluminescence (ECL) detection system (GE HEALTHCARE AMERSHAM UK) to visualize the antigen/antibody interaction.

Figure 9A:
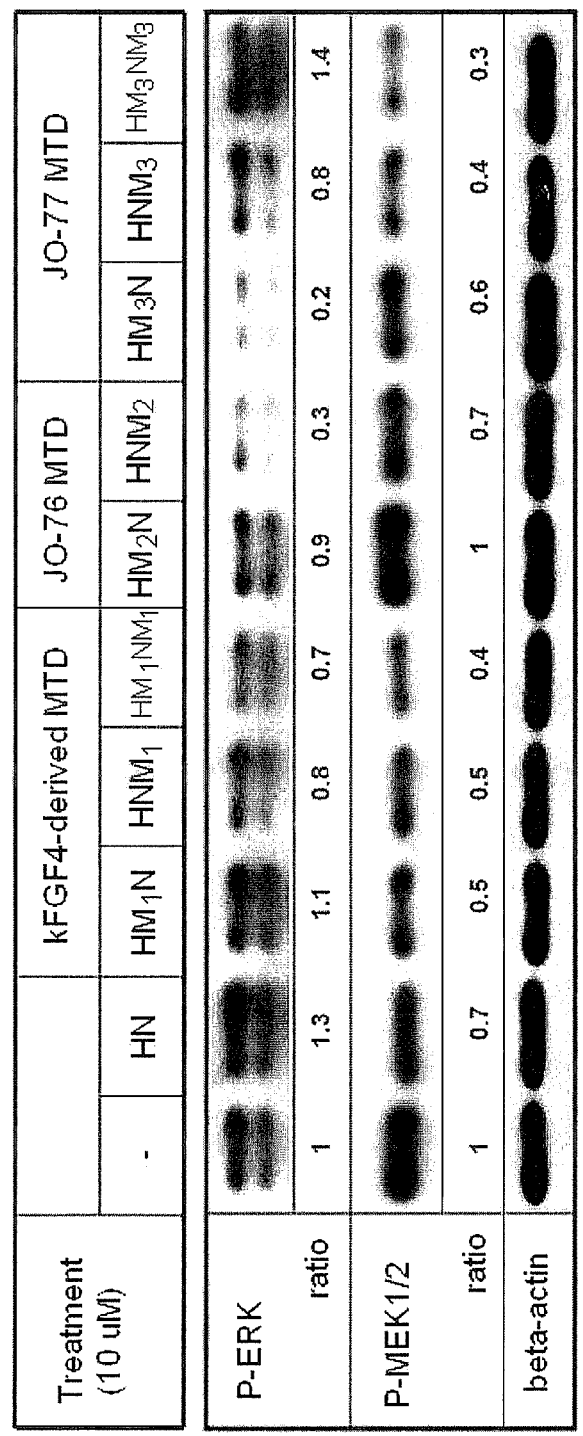
FIGS. 9a and 9b are photographs of a Western blot analysis showing the inhibitory effect of cell permeable Nm23 recombinant proteins according to the present invention on MAPK signal transduction.
Figure 9B:
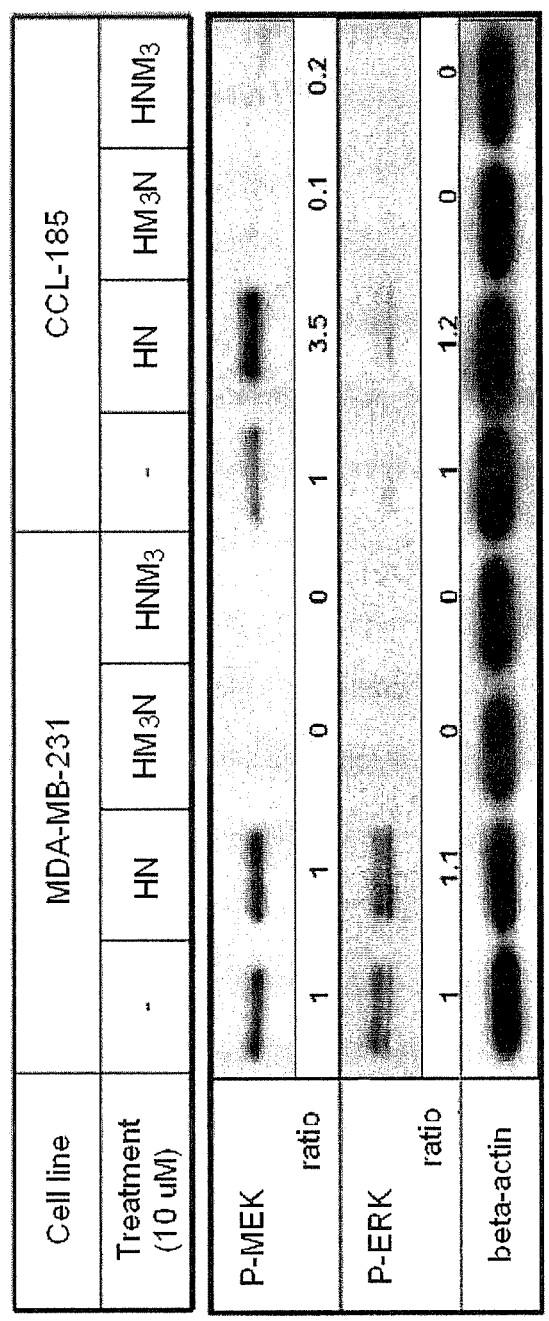

As shown in FIGS. 9a and 9b, in the cells treated with the cell permeable Nm23 recombinant protein as compared with cells treated with the control protein, the phosphorylation of KSR serine 392, which is a scaffold protein of the MAPK cascade, was enhanced, while the phosphorylation of MEK (P-MEK) that induces the activation of tumor cell cycle was reduced. In particular, the $HM_3N$ and $HNM_3$ recombinant proteins where a JO-77 MTD was fused to the N- and C-terminus, respectively, strongly inhibited the phosphorylation of ERK and MEK in all three types of human cancer cell lines.

Example 7

In Vitro Anti-Metastatic Effect of Cell Permeable Nm23 Recombinant Proteins

<7-1>Invasion assay

In order to examine whether tumor metastasis is inhibited by blocking cancer cell migration in cancer cells treated with the cell permeable Nm23 recombinant proteins according to the present invention, an invasion assay was carried out as follows.

First, a human breast cancer cell line, MDA-MB-435 cells, were cultured overnight in a RPMI 1640 medium supplemented with 10% FBS in the absence of growth factors. The next day, the cells were treated with trypsin and harvested, followed by suspension in the same RPMI 1640 medium. The cells were treated with each of the MTD-lacking Nm23 control protein (HN), and cell permeable Nm23 recombinant proteins ($HM_2N$, $HNM_2$, $HM_3N$, $HNM_3$ and $HM_3NM_3$) according to the present invention at a concentration of 10 µM at 37° C. for 1 hour. Meanwhile, the top part of a trans-well polycarbonate membrane filter (BD Falcon) having a pore size of 3 µm was coated with MATRIGEL (40 µg per each well; BD Biosciences). To the lower part of the chamber, a DMEM medium supplemented with 10% FBS was added as an adhesive substrate. The cells treated with the above protein were suspended in a DMEM medium supplemented with 0.1% FBS to prepare a cell suspension. The thus prepared cell suspension was inoculated on the trans-well membrane filter ($1 \times 10^5$ cells per each well), and cultured in a 5% $CO_2$ incubator at 37° C. for 20 to 24 hours. The filters were washed with PBS, and the non-invasive cells remaining on the surface of the upper part were removed by using a cotton swab. The invasive cells that passed through the Matrigel and migrated to the lower part of the filter were fixed with 4% paraformaldehyde for 5 to 10 minutes, and stained with 0.5% (w/v)

hemacolor for 10 to 20 minutes. The number of cells migrated to the base surface of the membrane filter (violet color) was counted by observing with an optical microscope.

Figure 10A:
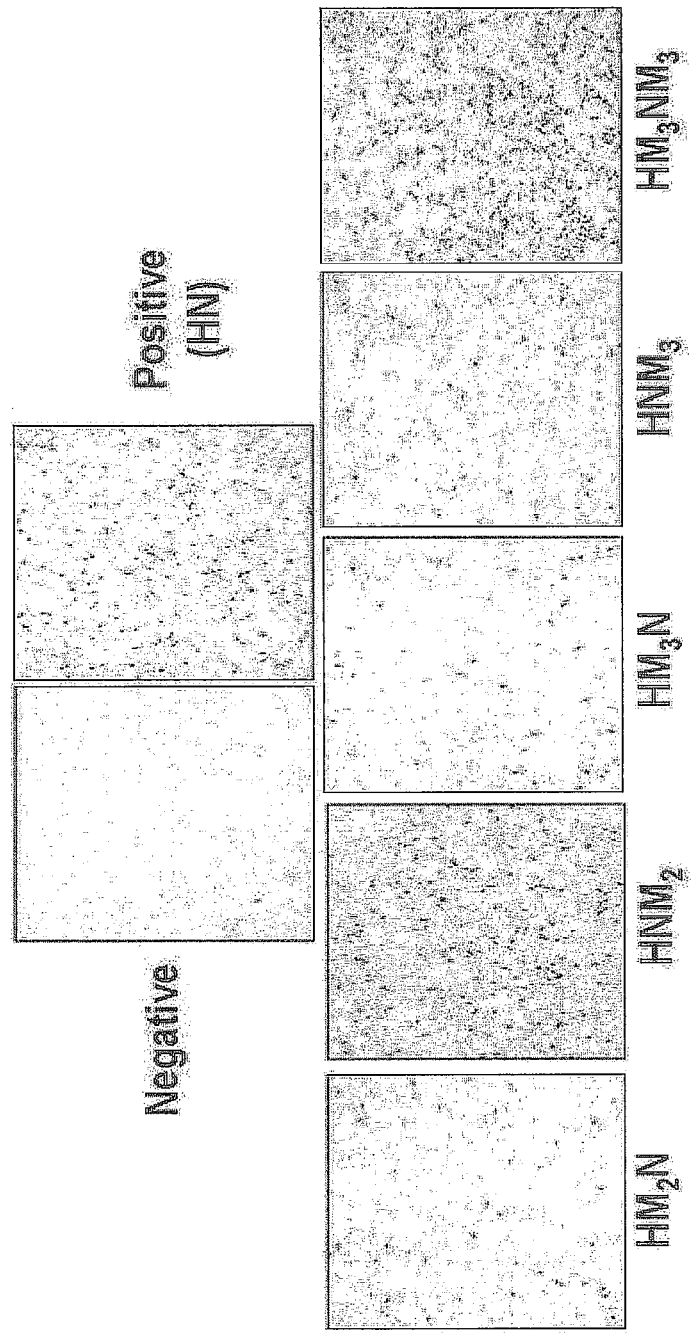
Figure 10B:
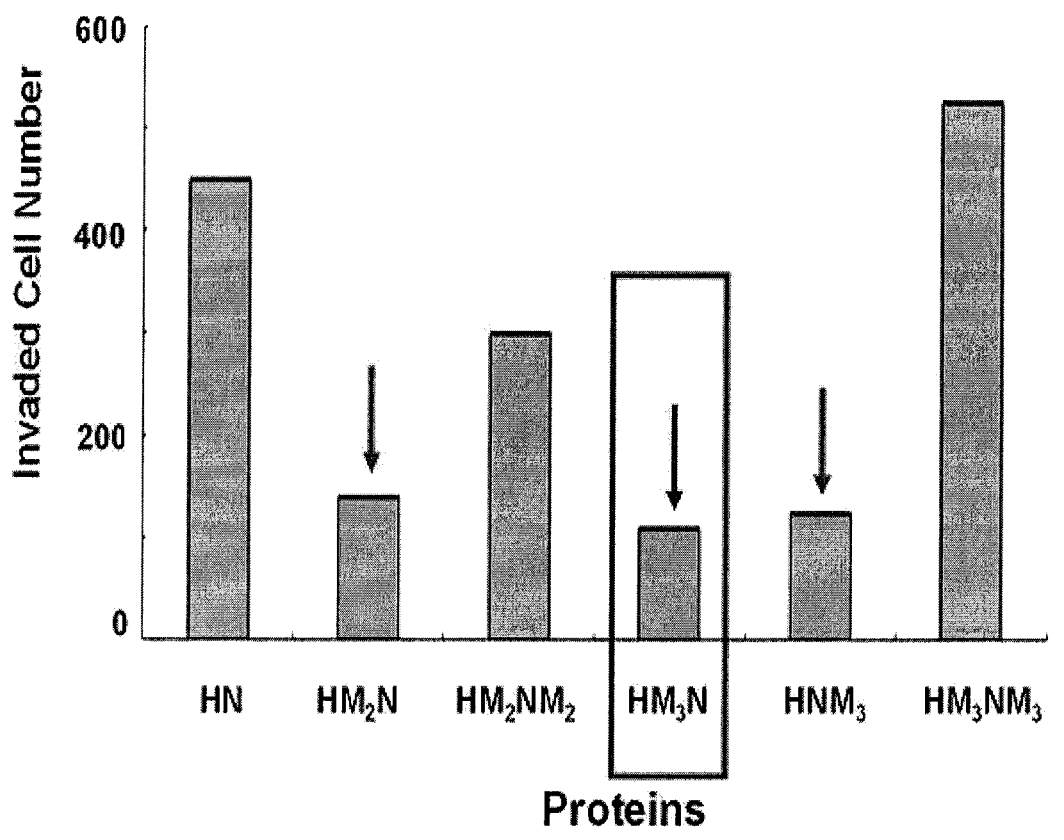

According to the results shown in FIGS. 10a and 10b, in case of the cells treated with most of the cell permeable Nm23 recombinant proteins, $HM_2N$, $HM_3N$ and $HNM_3$ in particular, as compared with the control protein (HN), the invasion of the cells was significantly reduced. From these results, it was found that the cell permeable Nm23 recombinant proteins according to the present invention can effectively inhibit metastatic potential of tumor cells in vivo.

<7-2>Wound migration assay

In order to examine whether the cell permeable Nm23 recombinant proteins according to the present invention can inhibit the migration of a breast cancer cell line, MDA-MB-435 cells, having high migration activity, a wound migration assay was carried out as follows.

MDA-MB-435 cells were cultured in a 60-mm culture dish until they formed a confluent monolayer covering the bottom thereof. After incubation, the cells were treated with each of the MTD-lacking Nm23 control protein (HN) and cell permeable Nm23 recombinant proteins ($HM_2N$, $HNM_2$, $HM_3N$, $HNM_3$ and $HM_3NM_3$) according to the present invention at a concentration of 10 µM at 37° C. for 1 hour. After the cells were washed with PBS, they were wounded with a sterile yellow tip, to thereby form a reference line that separated the confluent area from the bare area. To the cells was added a RPMI medium (3 mL) supplemented with 10% FBS, followed by culturing in a 5% $CO_2$ incubator at 37° C. for 24 hours. The cells were washed with PBS, fixed with methanol for 1 minute, stained with Giemsa (Chameleon Chemical) for 5 minutes, and then, washed with distilled water. The migration was quantified by counting the number of cells that migrated from the wound edge into the bare area with an inverted light microscope at 40× magnification.

Figure 11:
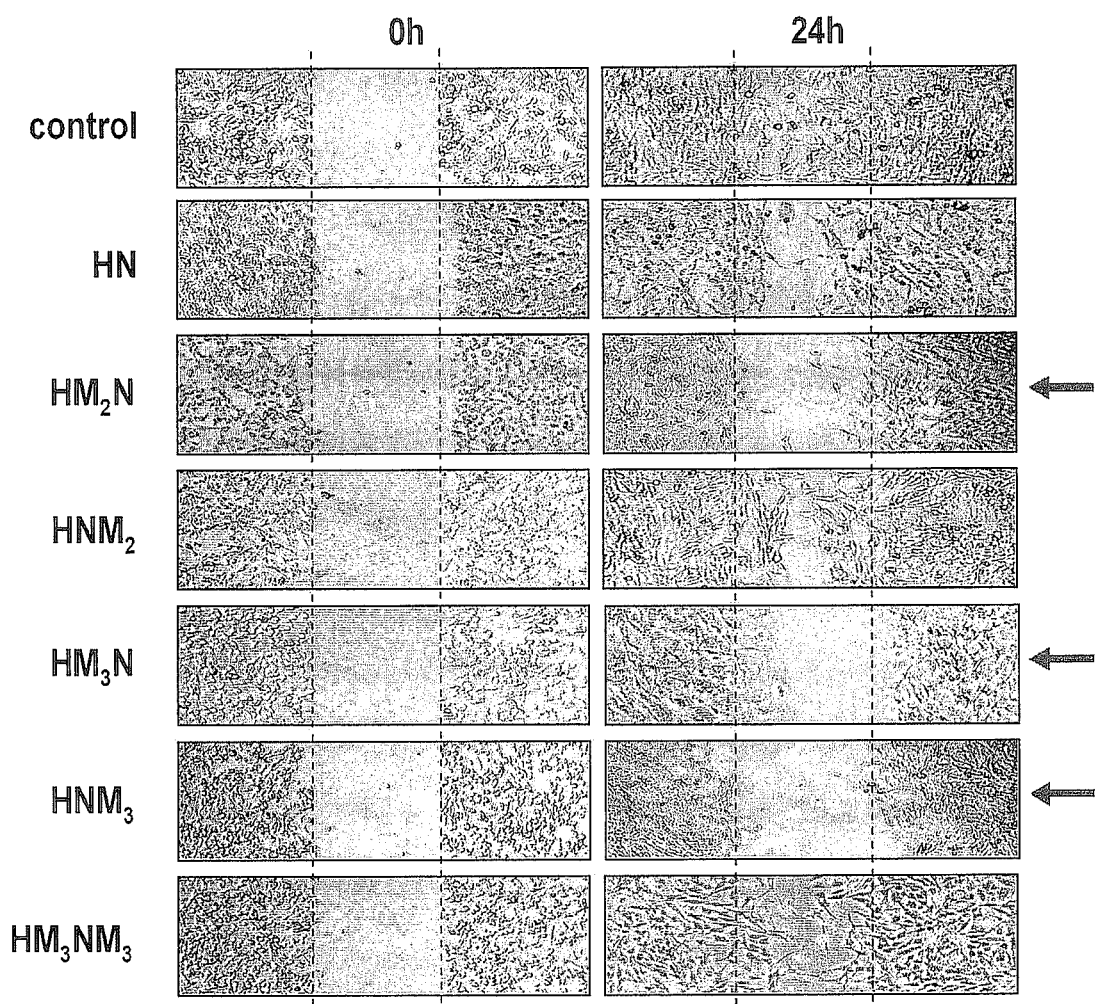
FIG. 11 is a photograph of a wound migration assay showing the inhibitory effect of cell permeable Nm23 recombinant proteins according to the present invention on metastasis.

Referring to the results shown in FIG. 11, the migration of tumor cells was remarkably inhibited in the cells treated with the cell permeable Nm23 recombinant proteins, $HM_2N$, $HM_3N$ and $HNM_3$ in particular, as compared with the control protein, which is consistent with the results from the invasion assay above.

Example 8

In Vivo Anti-Metastatic Effect of Cell Permeable Nm23 Recombinant Proteins

In order to examine the in vivo inhibitory effect of the cell permeable Nm23 recombinant proteins on tumor metastasis which has already been confirmed in vitro, an immunohistochemical analysis was carried out as follows.

First, MDA-MB-435 cells, a highly metastatic human breast cancer cell line, were suspended in 0.1 of PBS at a concentration of $1 \times 10^6$ cells/ml and were injected to the outer tail vein of 5-week old MHC (major histocompatibility complex)-deficient Balb/c nu/nu mice. Twenty mice were subdivided into 4 groups of 5 mice each. Each of the cell permeable Nm23 recombinant protein ($HM_3N$, 300 µg) to which a JO-77 MTD was fused, a vehicle (PBS, 300 µg) and MTD-lacking Nm23 control protein (HN, 300 µg), and an EGFP recombinant protein ($HM_3E$) where a JO-77 MTD was fused to the N-terminus of EGFP was administered to the mice. Here, the MTD-fused EGFP recombinant protein was employed as a control to examine whether the JO-77 MTD being fused to Nm23 had an effect on Nm23 expression. Five weeks after MDA-MB-435 cells were injected to the mice, the proteins were administered daily to the mice of each group via intravenous injection for 21 days. After three mice were selected from each group and sacrificed, lung tissue samples were extracted therefrom. The other two mice remaining in each group had undergone further observation for 14 days after the administration was terminated, and then, lung tissue samples were extracted therefrom. The lung tissue samples were fixed with a Bouin fixation solution overnight for detecting metastatic colonies, washed with distilled water, and then embedded in paraffin to prepare a paraffin block. Thus prepared paraffin block was sliced with a microtome to have a thickness of 4 µm, where the slices were mounted on a glass slide and treated with xylene for 5 minutes three times to remove paraffin. The glass slide was subjected to immunohistochemical staining with vimentin as a metastatic marker.

For the immunohistochemical staining, anti-vimentin antibody (ABCAM) was employed as a primary antibody, and goat anti-mouse IgG-HRP (Santa Cruz Biotechnology) was used as a secondary antibody. In order to prevent the nonspecific interaction between blotted proteins and irrelevant antibodies, the glass slide was blocked with 5% non-fat dry milk in TBS/T (10 mM Tris-Cl, pH 8.0, 150 mM NaCl, 0.05% Tween 20) at room temperature for 1 hour with stirring. After removing the blocking buffer, the glass slide was washed with TBS/T three times, followed by incubating with the anti-vimentin antibody as a primary antibody (diluted with PBS at a ratio of 1:200) for 1 hour at 4° C. After the removing the primary antibody solution, the glass slide was washed with TBS/T five times each for 5 minutes, and incubated with the goat anti-mouse IgG-HRP as a secondary antibody (diluted with PBS at a ratio of 1:200) for 1 hour at room temperature. After washing with TBS/T (0.025% Triton-X 100) twice, the glass slide was stained with a DAB substrate to detect vimentin.

FIG. 12a shows the results of optically observing the lung tissue extracted from the mouse after the cell permeable Nm23 recombinant protein according to the present invention was administered for 21 days, and the same was extracted from the mouse where the administration of the cell permeable Nm23 recombinant protein was terminated for 14 days. As shown in FIG. 12a, in the lung tissues of mice treated with the vehicle, control protein (HN), and MTD-fused EGFP recombinant protein ($HM_3E$), tumor growth was remarkably increased in spite of the treatment with the proteins for 21 days. Further, the tumor size was not reduced after the subsequent non-treatment period of 2 weeks and newly formed tumors were found in other peripheral tissues, showing that metastasis occurred. However, in the lung tissue of the mouse treated with the cell permeable Nm23 recombinant protein ($HM_3N$) according to the present invention, there was no tumor formation not only during the 3-week period of protein treatment, but also during the subsequent 2-week period of the non-treatment, suggesting that the tumor formation and metastasis are effectively inhibited by the cell permeable Nm23 recombinant protein.

Figure 12B:
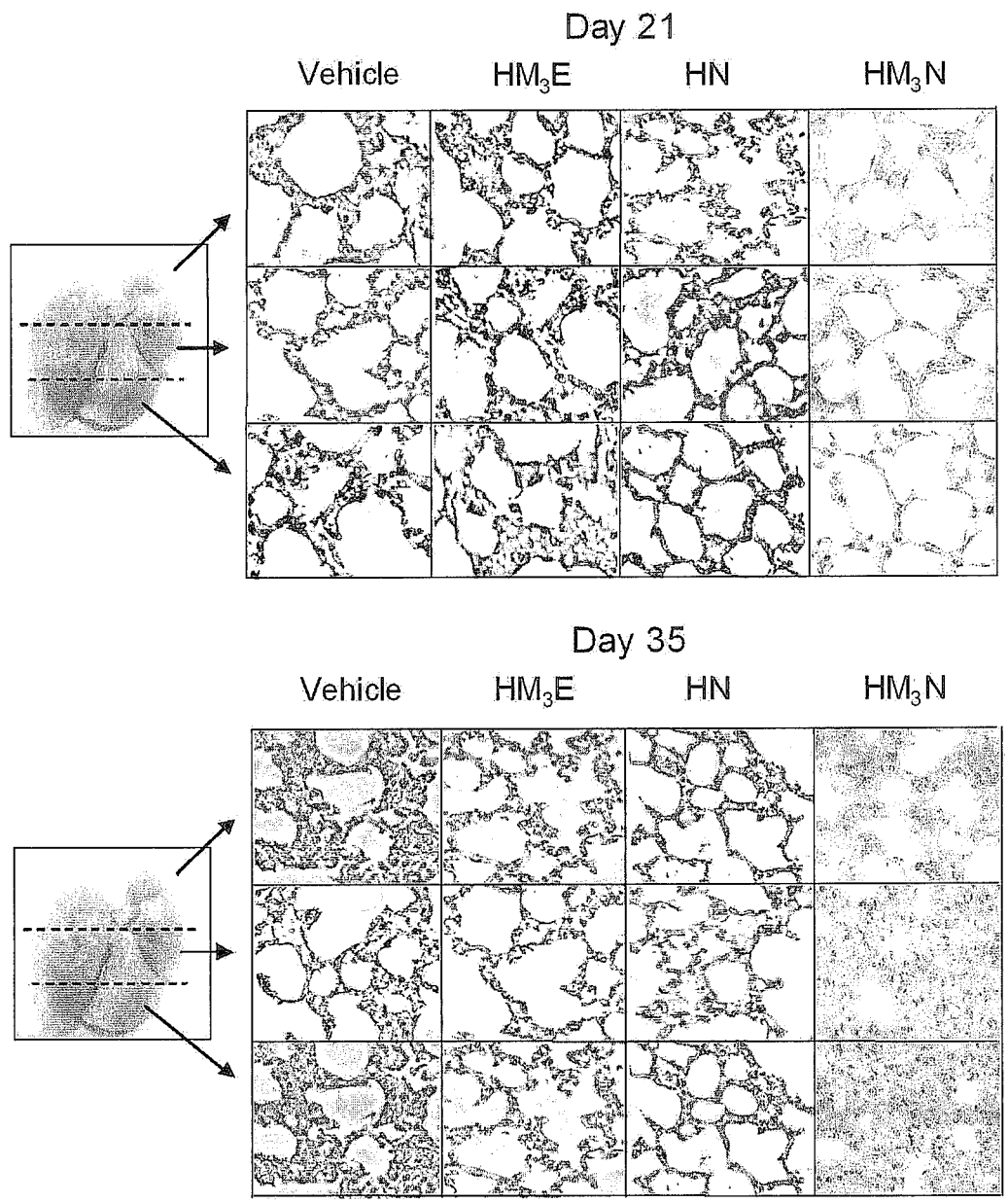
FIG. 12b is a photograph of immunohistochemical staining showing the expression of a metastatic marker, vimentin, in a mouse lung tissue extracted from a mouse administered with the cell permeable Nm23 recombinant protein according to the present invention.

FIG. 12b depicts the results of immunohistochemical staining showing the expression of a metastatic marker, vimentin, in the lung tissue extracted from the mouse after the cell permeable Nm23 recombinant protein according to the present invention was administered for 21 days (Day 21), and the lung tissue extracted from the mouse where the administration of the cell permeable Nm23 recombinant protein was terminated for 14 days (Day 35). As shown in FIG. 12b, vimentin was detected in the lung tissue of the mice treated with the vehicle, control protein (HN), and MTD-fused EGFP recombinant protein ($HM_3E$) both on Day 21 and on Day 35, while vimentin was not detected in the lung tissue of the mouse treated with the cell permeable Nm23 recombinant protein (HM₃N) according to the present invention neither on Day 21 nor on Day 35. From these results, it was confirmed that the cell permeable Nm23 recombinant protein according to the present invention can effectively inhibit tumor metastasis in vivo.

Example 9

In Vivo Apoptosis-Inducing Effect after the Administration of Cell Permeable Nm23 Recombinant Proteins In order to examine the effect of inducing apoptosis in tumor tissues after the administration of the cell permeable Nm23 recombinant proteins, a TUNEL (terminal deoxynucleotidyl transferase-mediated dUTP nick-end labeling) assay was performed by using the same mouse model as described in Example 8. The TUNEL assay was carried out by using an in situ cell death detection kit (TMR red, ROCHE).

In particular, each of the cell permeable Nm23 recombinant protein (HM₃N), vehicle and HN as a control, and MTD-fused EGFE recombinant protein (HM₃E) was daily administered to the mice subdivided into four groups via intravenous injection for 21 days according to the same method as described in Example 8. After three mice were selected from each group and sacrificed, lung tissue samples were extracted therefrom. The other two mice remaining in each group had undergone further observation for 14 days after the administration was terminated, and then, lung tissue samples were extracted therefrom. The lung tissue samples were embedded in paraffin to prepare a paraffin block. Thus prepared paraffin block was sectioned with a microtome to have a thickness of 5 μm and mounted on a glass slide. The glass slide was treated with xylene for 5 minutes three times, to thereby remove paraffin. It was then successively treated with 100% ethanol twice for 5 minutes, and 90%, 80% and 70% ethanol each for 3 minutes so as to dehydrate the lung tissue, followed by incubation in PBS for 5 minutes. The glass slide was treated with 0.1% Trition® X-100 dissolved in a 0.1% sodium citrate solution for 8 minutes, and washed with PBS twice for 2 minutes. After a drop of TUNEL reaction buffer (50 μl, ROCHE, USA) was added to the glass slide, the glass slide was incubated in a humidified incubator at 37° C. for 1 hour, washed with PBS three times, and then, observed with a fluorescence microscope.

Figure 13:
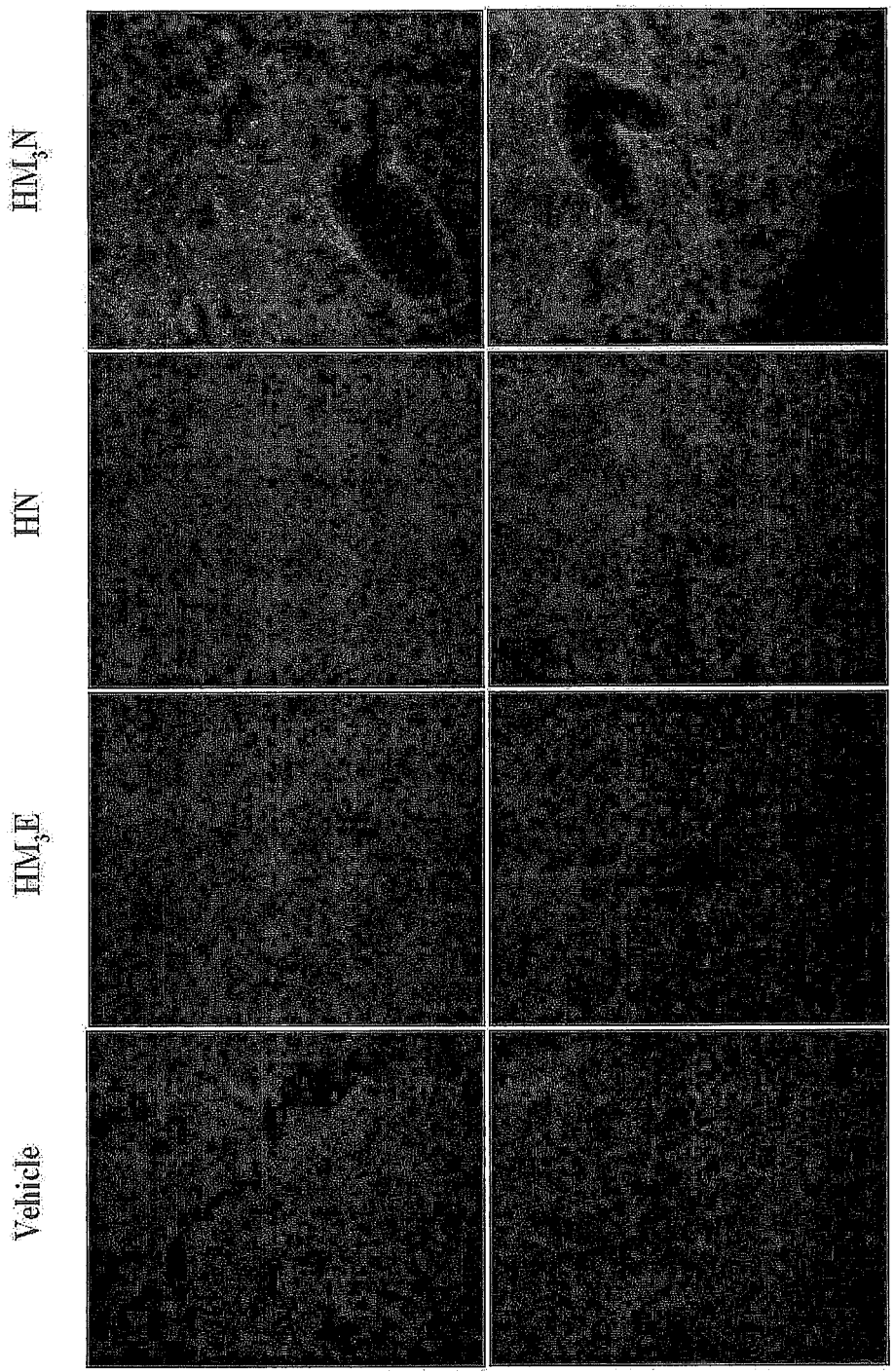
FIG. 13 is a photograph of a terminus deoxynucleotidyl transferase-mediated dUTP nick-end labeling (TUNEL) analysis showing the apoptosis-inducing effect in a mouse lung tissue extracted from a mouse administered with the cell permeable Nm23 recombinant protein according to the present invention.

Referring to the results shown in FIG. 13, there was no significant histological change in the mouse lung tissue treated with the vehicle, control protein (FIN) and MTD-fused EGFP recombinant protein, while in the mouse lung tissue treated with the cell permeable Nm23 recombinant protein (HM₃N), a region stained in red representing the characteristic of apoptosis was observed, confirming the effect of inducing apoptosis of the cell permeable Nm23 recombinant protein according to the present invention. Further, it was also observed that in the mouse lung tissue treated with the cell permeable Nm23 recombinant protein according to the present invention, apoptosis was still induced in cancer cells 14 days after the administration was terminated.

Example 10

Comparison of Protein Expression Pattern after the Administration of Cell Permeable Nm23 Recombinant Proteins In order to examine the change in protein expression pattern in the tumor tissue treated with the cell permeable Nm23 recombinant protein according to the present invention, a microarray assay was performed as follows.

In particular, each of the cell permeable Nm23 recombinant protein (HM₃N), vehicle and HN (control) was administered to the mice subdivided into three groups via intravenous injection for 21 days, and then left alone for 14 days after the administration was terminated, according to the same method as described in Example 9 above. Fourteen days after the administration was terminated, lung tissue samples were extracted from the mouse of each group and freezed with liquid nitrogen. Total RNA was isolated from the lung tissue by using a TRIZOL reagent (INVITROGEN) according to the manufacturer's instruction, and treated with an RNase-free DNase (LIFE TECHNOLOGIES, Inc.), to thereby completely remove the remaining genomic DNA.

The thus isolated RNA was subjected to synthesis and hybridization of a target cRNA probe by using a Low RNA Input Linear Amplification kit (Agilent Technology) according to the manufacturer's instruction. In brief, 1 μg of total RNA was mixed with a T7 promoter specific primer and reacted at 65° C. for 10 minutes. A cDNA master mix was prepared by mixing a first strand buffer (5×), 0.1 M DTT, 10 mM dNTP mix, RNase-Out and MMLV-RT (reverse transcriptase), and added to the reaction mixture. The resulting mixture was reacted at 40° C. for 2 hours, followed by reacting at 65° C. for 15 minutes, to thereby terminate the reverse transcription and dsDNA synthesis. A transcription master mix was prepared by mixing a transcription buffer (4×), 0.1 M DTT, NTP mix, 50% PEG, RNase-Out, inorganic pyrophosphatase, T7-RNA polymerase and cyanine (3/5-CTP) according to the manufacturer's instruction. The thus prepared transcription master mix was added to the dsDNA reaction mixture and reacted at 40° C. for 2 hours so as to perform dsDNA transcription. The thus amplified and labeled cRNA was purified with a cRNA Cleanup Module (AGILENT TECHNOLOGY) according to the manufacturer's instruction. The labeled target cRNA was quantified by using a ND-1000 spectrophotometer (NanoDrop Technologies, Inc.). After the labeling efficiency was examined, cRNA was mixed with a blocking agent (10×) and a fragmentation buffer (25×), and reacted at 60° C. for 30 minutes so as to carry out the fragmentation of cRNA. The fragmented cRNA was resuspended in a hybridization buffer (2×) and directly dropped on a Whole Human Genome Oligo Microarray (44K). The microarray was subjected to hybridization in a hybridization oven (Agilent Technology) at 65° C. for 17 hours, followed by washing according to the manufacturer's instruction (AGILENT Technology).

The hybridization pattern was read by using a DNA microarray scanner (AGILENT Technology) and quantified by using a Feature Extraction Software (AGILENT Technology). Data normalization and selection of fold-changed genes were carried out by using a Gene Spring GX 7.3 soft wear (AGILENT Technology). The average of the normalized ratio was calculated by dividing a normalized signal channel strength by a normalized control channel strength. Functional annotation for a gene was conducted by using a Gene Spring GX 7.3 software (AGILENT Technology) according to the Gene Ontology™ Consortium.

Figure 14:
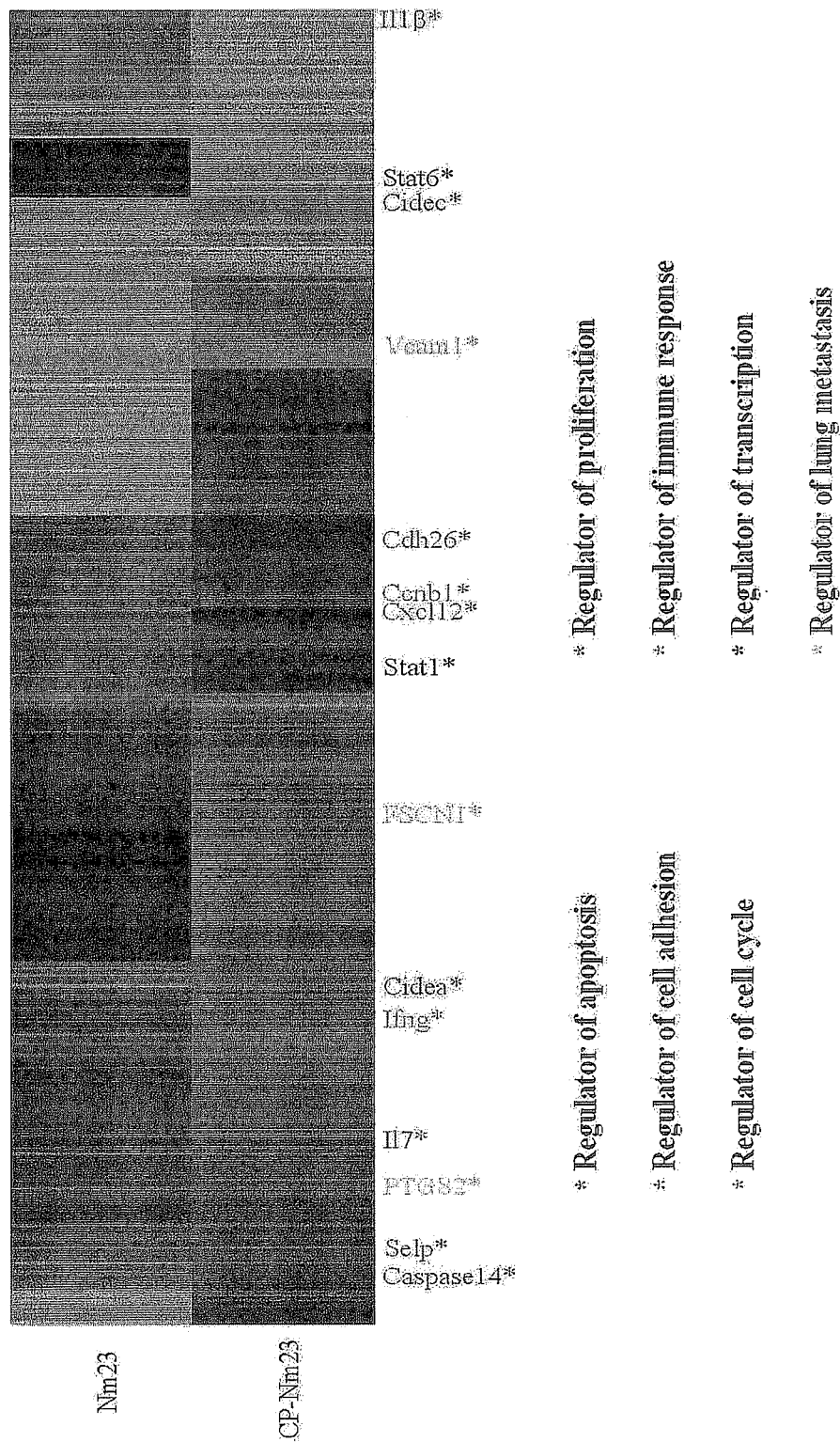
FIG. 14 is a photograph of a microarray analysis showing differential gene expression in a mouse lung tissue extracted from a mouse administered with the cell permeable Nm23 recombinant protein according to the present invention.

The results of the microarray analysis are summarized in FIG. 14 and Tables 3 to 9, where Table 3 shows the expression pattern of apoptosis-relating genes, Table 4 shows that of cell adhesion-relating genes, Table 5 shows that of cell cycle regulation-relating genes, Tables 6a and 6b show that of cell growth-relating genes, Table 7 shows that of cell proliferation-relating genes, Tables 8a and 8b show that of immue response-relating genes, and Table 9 shows that of metastasis-relating genes.

TABLE 3

| Gene | Genbank ID | Exp. pattern Veh. vs Nm23 | Exp. pattern Veh. vs CP-Nm23 | Total relative ratio | t-test/ p-value |
|---|---|---|---|---|---|
| Caspase 14 | NM_009809 | 1.21 | 4.19 | 3.46 | 0.82/0.01 |
| CD5 antigen | NM_007650 | 1.21 | 3.06 | 2.53 | 0.20/0.006 |
| PERP, TP53 apoptosis effector | NM_022032 | 1.04 | 2.51 | 2.41 | 0.72/0.01 |
| CD28 antigen | NM_007642 | 0.81 | 2.70 | 3.32 | 0.29/7.79E−14 |
| ELL associated factor 2 | NM_134111 | 0.72 | 3.85 | 5.33 | 0.08/0.009 |
| Interferon gamma | NM_008337 | 0.76 | 5.73 | 7.55 | 0.33/0.006 |
| Lectin, galactose binding, soluble 7 | NM_008496 | 0.79 | 8.83 | 11.16 | 0.33/0.006 |
| Programmed cell death 1 | NM_008798 | 0.98 | 4.74 | 4.85 | 0.85/0.008 |
| Transformation related protein 63 | NM_011641 | 2.61 | 8.22 | 3.15 | 0.04/0.009 |
| Deoxyribonuclease 1-like 3 | NM_007870 | 1.83 | 7.37 | 4.03 | 0.023/0.006 |
| Fas apoptotic inhibitory molecule 3 | NM_026976 | 0.47 | 1.40 | 2.96 | 0.02/0.08 |
| Interleukin 7 | NM_008371 | 0.82 | 2.36 | 2.86 | 0.028/0.24 |
| Granzyme B | NM_013542 | 0.28 | 0.72 | 2.52 | 0.014/0.09 |
| Cell death-inducing DFFA-like effector c | NM_178373 | 0.64 | 2.70 | 4.21 | 0.01/0.05 |
| Cell death-inducing DNA fragmentation factor, alpha subunit-like effector A | NM_007702 | 0.88 | 2.43 | 2.77 | 0.016/0.31 |

TABLE 4

| Gene | Genbank ID | Exp. pattern Veh. vs Nm23 | Exp. pattern Veh. vs CP-Nm23 | Total relative ratio | t-test/ p-value |
|---|---|---|---|---|---|
| Glycosylation dependent cell adhesion molecule 1 | NM_008134 | 0.92 | 4.48 | 4.88 | 0.82/0.04 |
| Selectin, platelet | NM_011347 | 0.94 | 3.79 | 4.04 | 0.83/0.01 |
| CD226 antigen | NM_178687 | 0.89 | 2.57 | 2.89 | 0.50/0.01 |
| Mucin 4 | NM_080457 | 0.93 | 2.05 | 2.19 | 0.58/0.02 |
| Cell adhesion molecule with homology to L1CAM | NM_007697 | 1.26 | 5.70 | 4.54 | 0.21/0.002 |
| RGM domain family, member B | BC030405 | 0.67 | 3.41 | 5.11 | 0.33/0.01 |
| Leupaxin | NM_134152 | 0.76 | 2.11 | 2.80 | 0.1/0.02 |
| Integrin, alpha E, epithelial-associated | NM_008399 | 0.82 | 2.66 | 3.24 | 0.39/0.02 |
| Coagulation factor VIII | NM_007977 | 0.85 | 2.08 | 2.43 | 0.47/0.03 |
| Corneodesmosin | NM_001008424 | 1.87 | 7.66 | 4.09 | 0.21/0.006 |
| Plakophilin 1 | NM_019645 | 8.26 | 28.39 | 3.44 | 0.02/0.005 |
| Stabilin 2 | NM_138673 | 0.40 | 0.80 | 1.98 | 0.038/0.221 |
| Myeloid/lymphoid or mixed lineage-leukemia translocation to 4 homolog | AK016557 | 0.30 | 0.64 | 2.12 | 0.017/0.071 |
| Kit ligand | NM_013598 | 0.20 | 0.47 | 2.38 | 0.008/0.013 |
| Glycoprotein (transmembrane) nmb | NM_053110 | 0.39 | 1.03 | 2.64 | 0.018/0.814 |
| Hairy and enhancer of split 1 | NM_008235 | 0.44 | 0.98 | 2.23 | 0.022/0.910 |
| CD164 antigen | NM_016898 | 0.33 | 0.89 | 2.74 | 0.012/0.377 |
| Procollagen, type XVII, alpha 1 | NM_007732 | 0.36 | 1.19 | 3.26 | 0.017/0.243 |
| Cysteine rich protein 61 | NM_010516 | 0.42 | 1.14 | 2.68 | 0.017/0.327 |
| Cartilage oligomeric matrix protein | NM_016685 | 3.53 | 0.66 | 0.19 | 0.012/0.127 |
| Cadherin-like 26 | NM_198656 | 2.85 | 0.85 | 0.30 | 0.017/0.298 |
| Aggrecan | NM_007424 | 2.84 | 0.97 | 0.34 | 0.013/0.787 |
| Poliovirus receptor-related 4 | NM_027893 | 2.03 | 0.97 | 0.48 | 0.023/0.758 |
| calsyntenin 1 | NM_023051 | 2.17 | 1.03 | 0.47 | 0.020/0.802 |
| laminin, beta 2 | NM_008483 | 2.10 | 1.05 | 0.50 | 0.022/0.665 |
| dermatopontin | NM_019759 | 3.11 | 1.22 | 0.39 | 0.012/0.187 |
| EGF-like repeats and discoidin I-like domains 3 | NM_010103 | 0.83 | 0.37 | 0.45 | 0.522/0.039 |

TABLE 5

| Gene | Genbank ID | Exp. pattern vs Nm23 | Exp. pattern vs CP-Nm23 | Total relative ratio | t-test/ p-value |
|---|---|---|---|---|---|
| Cell division cycle associated 8 | NM_026560 | 0.42 | 2.63 | 6.23 | 0.265/0.043 |
| Cyclin B1 | NM_172301 | 0.50 | 2.23 | 4.46 | 0.143/0.031 |
| Dedicator of cytokinesis 4 | NM_172803 | 0.66 | 2.71 | 4.13 | 0.174/0.018 |
| Budding uninhibited by benzimidazoles 1 homolog, beta | NM_009773 | 0.73 | 2.95 | 4.07 | 0.2/0.016 |
| Dual specificity phosphatase 1 | NM_013642 | 0.76 | 2.58 | 3.39 | 0.113/0.015 |
| Cell division cycle associated 3 | NM_013538 | 0.68 | 2.23 | 3.27 | 0.071/0.019 |
| FBJ osteosarcoma oncogene | NM_010234 | 0.98 | 3.44 | 3.50 | 0/0 |
| Protamine 1 | NM_013637 | 0.96 | 2.19 | 2.28 | 0.915/0.027 |
| FBJ osteosarcoma oncogene B | NM_008036 | 0.98 | 3.44 | 3.50 | 0.881/0.011 |
| Interleukin 1 beta | NM_008361 | 0.91 | 2.22 | 2.45 | 0.063/0 |
| M-phase phosphoprotein 1 | XM_193936 | 0.40 | 0.84 | 2.09 | 0.03/0.258 |
| Bridging integrator 1 | NM_009668 | 0.29 | 1.02 | 3.47 | 0.012/0.866 |
| Jun-B oncogene | NM_008416 | 0.43 | 1.00 | 2.34 | 0.017/0.977 |
| Calmodulin 1 | NM_009790 | 0.30 | 1.22 | 4.11 | 0.01/0.189 |
| Stratifin | NM_018754 | 2.68 | 1.03 | 0.38 | 0.014/0.883 |
| Avian erythroblastosis virus E-26 (v-ets) oncogene related | NM_133659 | 2.10 | 0.49 | 0.23 | 0.022/0.023 |

TABLE 6a

| Gene | Genbank ID | Exp. pattern Veh. vs Nm23 | Exp. pattern Veh. vs CP-Nm23 | Total relative ratio | t-test/ p-value |
|---|---|---|---|---|---|
| Keratin 5 | NM_027011 | 2.71 | 8.04 | 2.96 | 0.015/0.006 |
| Myosin, heavy polypeptide 8, skeletal muscle, perinatal | AK081482 | 1.45 | 2.91 | 2.00 | 0.2/0.02 |
| Paired box gene 9 | NM_011041 | 1.58 | 4.49 | 2.84 | 0.059/0.009 |
| Troponin T3, skeletal, fast | NM_011620 | 2.74 | 6.65 | 2.43 | 0.007/0.007 |
| Serine (or cysteine) peptidase inhibitor, clade B, member 3C | AK003650 | 1.04 | 9.02 | 8.71 | 0.26/0.006 |
| B-cell leukemia/lymphoma 2 related protein A1c | NM_007535 | 1.08 | 2.43 | 2.26 | 0.538/0.011 |
| OVO homolog-like 1 | NM_019935 | 1.08 | 2.26 | 2.09 | 0.553/0.014 |
| Junctophilin 2 | NM_021566 | 1.54 | 14.08 | 9.12 | 0.115/0.006 |
| Myosin, light polypeptide 1 | NM_021285 | 1.30 | 2.65 | 2.05 | 0.127/0.014 |
| Histocompatibility 2, class II antigen A, beta 1 | NM_207105 | 1.23 | 3.27 | 2.66 | 0.101/0.011 |
| Troponin I, skeletal, slow 1 | NM_021467 | 0.96 | 2.24 | 2.33 | 0.814/0.025 |
| Growth arrest specific 7 | NM_008088 | 0.94 | 3.02 | 3.22 | 0.619/0.012 |
| Tumor necrosis factor (ligand) superfamily, member 8 | NM_009403 | 0.91 | 2.89 | 3.16 | 0.719/0.016 |
| Frizzled homolog 10 | NM_175284 | 0.99 | 2.31 | 2.33 | 0.946/0.020 |
| Chemokine (C—X—C motif) ligand 13 | NM_018866 | 1.02 | 5.12 | 5.02 | 0.854/0.008 |
| RAB27A, member RAS oncogene family | NM_023635 | 0.71 | 2.24 | 3.15 | 0.326/0.033 |
| Tumor necrosis factor, alpha-induced protein 8-like 1 | NM_025566 | 0.74 | 2.15 | 2.88 | 0.122/0.021 |
| RAB32, member RAS oncogene family | NM_026405 | 0.71 | 2.41 | 3.38 | 0.08/0.017 |
| Tumor necrosis factor, alpha-induced protein 2 | NM_009396 | 0.74 | 2.37 | 3.22 | 0.096/0.017 |

TABLE 6b

| | | | | | |
|---|---|---|---|---|---|
| Tumor necrosis factor receptor superfamily, member 17 | NM_011608 | 0.65 | 4.42 | 6.81 | 0.083/0.009 |
| V-maf musculoaponeurotic fibrosarcoma oncogene family, protein B (avian) | NM_010658 | 0.83 | 2.03 | 2.45 | 0.203/0.023 |

TABLE 6b-continued

| | | | | | |
|---|---|---|---|---|---|
| Interleukin 7 receptor | NM_008372 | 0.82 | 2.36 | 2.86 | 0.195/0.017 |
| Fgfr1 oncogene partner | NM_201230 | 0.49 | 1.15 | 2.33 | 0.031/0.328 |
| Tescalcin | NM_021344 | 0.50 | 1.16 | 2.34 | 0.025/0.272 |
| Burkitt lymphoma receptor 1 | NM_007551 | 0.42 | 1.93 | 4.60 | 0.031/0.031 |
| Protein phosphatase 1, regulatory (inhibitor) subunit 14c | AK082372 | 0.18 | 0.40 | 2.22 | 0.019/0.184 |
| Eyes absent 4 homolog | NM_010167 | 1.07 | 0.46 | 0.43 | 0.721/0.046 |
| Sema domain, transmembrane domain (TM), and cytoplasmic domain, (semaphorin) 6D | AK052232 | 1.12 | 0.48 | 0.43 | 0.367/0.022 |
| Mutated in colorectal cancers | AK086823 | 0.87 | 0.41 | 0.47 | 0.347/0.019 |
| Sema domain, immunoglobulin domain (Ig), short basic domain, secreted, (semaphorin) 3E | AK049580 | 0.95 | 0.38 | 0.40 | 0.713/0.18 |
| Sine oculis-related homeobox 2 homolog | NM_011380 | 4.18 | 1.60 | 0.38 | 0.022/0.094 |
| Early B-cell factor 3 | AK220542 | 4.49 | 1.70 | 0.38 | 0.008/0.049 |
| V-abl Abelson murine leukemia viral oncogene 2 (arg, Abelson-related gene) | NM_009595 | 3.90 | 1.35 | 0.35 | 0.021/0.201 |
| Early B-cell factor 2 | NM_010095 | 2.88 | 1.30 | 0.45 | 0.015/0.152 |
| HtrA serine peptidase 3 | NM_030127 | 3.50 | 1.41 | 0.40 | 0.011/0.089 |
| Troponin T2, cardiac | NM_011619 | 2.33 | 1.13 | 0.49 | 0.018/0.34 |
| Developmental pluripotency associated 5 | NM_025274 | 2.30 | 0.85 | 0.37 | 0.027/0.414 |
| Receptor tyrosine kinase-like orphan receptor 1 | NM_013845 | 2.33 | 1.06 | 0.46 | 0.022/0.654 |
| Phospholipase C, gamma 1 | AF027185 | 3.05 | 0.99 | 0.33 | 0.012/0.951 |
| Deleted in lung and esophageal cancer 1 | AK045848 | 2.34 | 0.95 | 0.41 | 0.018/0.641 |
| Palate, lung, and nasal epithelium carcinoma associated | NM_011126 | 3.68 | 0.14 | 0.04 | 0.007/0/007 |

TABLE 7

| Gene | Genbank ID | Exp. pattern | | Total relative ratio | t-test/ p-value |
|---|---|---|---|---|---|
| | | Veh. vs Nm23 | Veh. vs CP-Nm23 | | |
| Protein kinase, cAMP dependent regulatory, type I beta | NM_008923 | 0.87 | 2.02 | 2.31 | 0.494/0.049 |
| B-cell translocation gene 1, anti-proliferative | NM_007569 | 0.90 | 2.02 | 2.25 | 0.406/0.024 |
| Fc receptor, IgG, low affinity IIb | NM_010187 | 0.77 | 2.16 | 2.82 | 0.112/0.018 |
| Immunoglobulin heavy chain 6 (heavy chain of IgM) | AJ294737 | 0.71 | 2.11 | 2.97 | 0.079/0.021 |
| Neutrophil cytosolic factor 1 | NM_010876 | 1.02 | 2.35 | 2.30 | 0.888/0.019 |
| complement factor B | NM_008198 | 1.12 | 3.27 | 2.91 | 0.365/0.011 |
| B-cell translocation gene 2, anti-proliferative | NM_007570 | 0.30 | 0.68 | 2.28 | 0.548/0.02 |
| Signal transducer and activator of transcription 6 | NM_009284 | 0.48 | 2.34 | 4.88 | 0.04/0.019 |
| Protein tyrosine phosphatase, receptor type, C | NM_011210 | 0.48 | 1.35 | 2.79 | 0.022/0.1 |
| Protein-kinase, interferon-inducible double stranded RNA dependent inhibitor, repressor of (P58 repressor) | NM_028410 | 0.31 | 0.83 | 2.71 | 0.011/0.266 |
| Pleckstrin homology domain containing, family K member 1 | AK045134 | 0.70 | 0.25 | 0.36 | 0.08/0.011 |

TABLE 8a

| Gene | Genbank ID | Exp. pattern Veh. Vs Nm23 | Exp. pattern Veh. Vs CP-Nm23 | Total Relative ratio | t-test/ p-value |
|---|---|---|---|---|---|
| Immunoglobulin heavy chain (J558 family) | AF296432 | 0.86 | 16.25 | 18.85 | 0.905/ 0.011 |
| Immunoglobulin heavy chain complex | BC004786 | 0.96 | 15.09 | 15.69 | 0.736/ 0.006 |
| Histocompatibility 2, T region locus 22 | NM_010397 | 1.00 | 2.87 | 2.89 | 0.966/ 0.013 |
| Lymphocyte antigen 86 | NM_010745 | 0.99 | 2.42 | 2.44 | 0.936/ 0.016 |
| Defensin beta 6 | NM_054074 | 0.97 | 2.19 | 2.26 | 0.863/ 0.025 |
| Immunoglobulin joining chain | NM_152839 | 0.84 | 26.49 | 31.61 | 0.219/ 0.005 |
| Histocompatibility 2, class II antigen E beta | NM_010382 | 0.93 | 3.65 | 3.92 | 0.55/ 0.01 |
| Lymphocyte antigen 6 complex, locus F | NM_008530 | 1.04 | 3.53 | 3.41 | 0.784/ 0.01 |
| Thymus cell antigen 1, theta | NM_009382 | 1.04 | 2.47 | 2.38 | 0.762/ 0.016 |
| CD8 antigen, alpha chain | BC030679 | 0.78 | 6.62 | 8.51 | 0.142/ 0.007 |
| Chemokine (C-C motif) receptor 5 | NM_009917 | 0.86 | 2.65 | 3.09 | 0.265/ 0.014 |
| Proteoglycan 2, bone marrow | NM_008920 | 0.88 | 3.64 | 4.13 | 0.373/ 0.01 |
| Histocompatibility 2, class II, locus Mb2 | NM_010388 | 0.93 | 2.68 | 2.90 | 0.518/ 0.014 |
| Defensin beta 3 | NM_013756 | 1.21 | 5.89 | 4.89 | 0.364/ 0.007 |
| Histocompatibility 2, class II, locus Mb2 | NM_010388 | 1.08 | 2.79 | 2.57 | 0.53/ 0.013 |
| Histocompatibility 2, O region beta locus | NM_010389 | 1.06 | 2.45 | 2.31 | 0.647/ 0.017 |
| Histocompatibility 2, class II antigen E alpha | NM_010381 | 1.11 | 4.12 | 3.73 | 0.423/ 0.009 |
| Transporter 1, ATP - binding cassette, sub - family B (MDR/TAP) | NM_013683 | 1.21 | 3.38 | 2.80 | 0.226/ 0.011 |
| Peptidoglycan recognition protein 1 | NM_009402 | 1.25 | 2.71 | 2.17 | 0.159/ 0.014 |
| T - cell receptor beta, variable 13 | BC030075 | 0.60 | 2.08 | 3.47 | 0.148/ 0.012 |
| Indoleamine - pyrrole 2,3 dioxygenase | NM_008324 | 0.68 | 5.91 | 8.68 | 0.079/ 0.007 |
| Histocompatibility 2, class II, locus Mb1 | NM_010387 | 0.83 | 2.20 | 2.64 | 0.214/ 0.019 |

TABLE 8b

| Gene | Genbank ID | Veh. Vs Nm23 | Veh. Vs CP-Nm23 | Total Relative ratio | t-test/p-value |
|---|---|---|---|---|---|
| CD3 antigen, gamma polypeptide | NM_009850 | 0.68 | 5.05 | 7.46 | 0.063/0.008 |
| CD96 antigen | NM_032465 | 0.79 | 2.39 | 3.02 | 0.148/0.017 |
| Histocompatibility 2, class II antigen A, alpha | NM_010378 | 0.72 | 2.75 | 3.82 | 0.12/0.014 |
| Histocompatibility 2, 0 region alpha locus | NM_008206 | 0.65 | 2.81 | 4.31 | 0.053/0.013 |
| Chemokine (C-X-C motif) receptor 3 | NM_009910 | 0.63 | 3.25 | 5.12 | 0.048/0.008 |
| CD8 antigen, beta chain 1 | NM_009858 | 0.75 | 2.15 | 2.86 | 0.107/0.021 |
| CD86 antigen | NM_019388 | 0.83 | 2.29 | 2.77 | 0.066/0.01 |
| CD3 antigen, delta polypeptide | NM_013487 | 0.56 | 3.42 | 6.16 | 0.031/0.011 |
| Interferon gamma inducible protein 47 | NM_008330 | 0.67 | 2.23 | 3.33 | 0.06/0.019 |
| Immunoglobulin lambda chain, variable 1 | AK008094 | 0.40 | 2.85 | 7.15 | 0.044/0.015 |
| CD180 antigen | NM_008533 | 0.42 | 2.19 | 5.22 | 0.107/0.042 |
| Coiled-coil domain containing 85A | AK087049 | 1.00 | 0.44 | 0.44 | 0.984/0.019 |
| Cathelicidin antimicrobial peptide | NM_009921 | 1.19 | 0.37 | 0.31 | 0.243/0.016 |
| Neutrophilic granule protein | NM_008694 | 1.41 | 0.36 | 0.25 | 0.083/0.007 |

TABLE 9

| Gene | Genbank ID | Exp. pattern Veh. vs Nm23 | Exp. pattern Veh. vs CP-Nm23 | Total relative ratio | t-test/ p-value |
|---|---|---|---|---|---|
| Fascin homolog 1, actin bundling protein | NM_007984 | 1.31 | 3.56 | 2.72 | 0.118/0.01 |
| Prostaglandin-endoperoxide synthase 2 | NM_011198 | 0.81 | 2.09 | 2.59 | 0.459/0.047 |
| Vascular cell adhesion molecule 1 | NM_011693 | 0.79 | 1.62 | 2.05 | 0.146/0.044 |

As described in Table 3 above, in case of the apoptosis-relating genes, while the expressions of Caspase 14, cell death-inducing DFFA-like effector c (Cidec), cell death-inducing DNA fragmentation factor and alpha subunit-like effector A (Cidea) were up-regulated by about 3.5-, 4.0-, 2.5- and 2.5-fold, respectively, in the mouse group treated with the cell permeable Nm23 recombinant protein compared to that treated with the control protein.

As described in Table 4 above, in case of the cell adhesion-relating genes, the expression of cadherin-like 26 was down-regulated by about 3.0-fold in the mouse group treated with the cell permeable Nm23 recombinant protein compared to that treated with the control protein.

As described in Table 5 above, in case of the cell cycle regulation-relating genes, the expression of Avian erythroblastosis virus E-26 (v-ets) oncogene was down-regulated by about 4.0-fold in the mouse group treated with the cell permeable Nm23 recombinant protein compared to that treated with the control protein.

As described in Tables 6a and 6b above, in case of the cell growth-relating genes, while the expression of member 17 of a tumor necrosis factor receptor superfamily was up-regulated by about 6.8-fold, the expressions of palate, lung and nasal epithelium carcinoma associated genes were down-regulated by about 26.0-fold in the mouse group treated with the cell permeable Nm23 recombinant protein compared to that treated with the control protein.

As described in Table 7 above, in case of the cell proliferation-relating genes, the expression of signal transducer and activator of transcription 6 was up-regulated by about 5-fold in the mouse group treated with the cell permeable Nm23 recombinant protein compared to that treated with the control protein.

As described in Tables 8a and 8b above, in case of immune response-relating genes, the expressions of immunoglobulin heavy chain (J558 family), immunoglobulin heavy chain complex and immunoglobulin joining chain were up-regulated by about 18-, 15- and 30-fold, respectively, in the mouse group treated with the cell permeable Nm23 recombinant protein compared to that treated with the control protein.

As described in Table 9 above, in case of metastasis-relating genes, the expressions of fascin homolog 1 (actin bundling protein), prostaglandin-endoperoxide synthase 2 and vascular cell adhesion molecule 1 were up-regulated by about 2.5-, 2.5- and 2.0-fold, respectively, in the mouse group treated with the cell permeable Nm23 recombinant protein compared to that treated with the control protein.

Although the invention has been described in detail for the purpose of illustration, it is understood that such detail is solely for that purpose, and variations can be made therein by those skilled in the art without departing from the spirit and scope of the invention which is defined by the following claims.

INDUSTRIAL APPLICABILITY

The cell permeable Nm23 recombinant proteins of the present invention can induce the KSR phosphorylation and inactivation and inhibit the Ras-mediated MAPK cascade by efficiently introducing a metastasis suppressor Nm23 into a cell. Therefore, the cell permeable Nm23 recombinant proteins of the present invention can be effectively used as an anti-metastatic agent capable of preventing cancer metastasis by suppressing the proliferation, differentiation and migration of cancer cells.

The invention claimed is:

1. A cell permeable Nm23 recombinant protein comprising:
a macromolecule transduction domain(MTD) fused to the N-terminus or C-terminus of a human metastasis suppressor Nm23, wherein the MTD comprises SEQ ID NO: 6 or 8, and the Nm23 comprises SEQ ID NO: 2.

2. A cell permeable Nm23 recombinant protein comprising:
a first MTD fused to the N-terminus of a human metastasis suppressor Nm23 and a second MTD fused to the C-terminus of said human metastasis suppressor, wherein the first and second MTDs comprise SEQ ID NO: 6 or 8 and the Nm23 comprises SEQ ID NO: 2.

3. The cell permeable Nm23 recombinant protein according to claim 1, wherein the recombinant protein is selected from the group consisting of: a recombinant protein wherein the MTD comprises SEQ ID NO:6 and is fused to the N-terminus of the Nm23; a recombinant protein wherein the MTD comprises SEQ ID NO:6 and is fused to the C-terminus of the Nm23; a recombinant protein wherein the MTD comprises SEQ ID NO: 8 and is fused to the N-terminus of the Nm23; and a recombinant protein wherein the MTD comprises SEQ ID NO:8 and is fused to the C-terminus of the Nm23.

4. The cell permeable Nm23 recombinant protein according to claim 1, wherein the recombinant protein has an amino acid sequence selected from the group consisting of SEQ ID NOS: 28, 30, 32, and 34.

5. A polynucleotide encoding the cell permeable Nm23 recombinant protein according to claim 1.

6. The polynucleotide according to claim 5, wherein the polynucleotide has a nucleotide sequence selected form the group consisting of SEQ ID NOS: 27, 29, 31, and 33.

7. An expression vector comprising the polynucleotide according to claim 5.

8. The expression vector according to claim 7, wherein the expression vector is selected from the group consisting of pET28a(+)-HM₂N, pET28a(+)-HNM₂, and pET28(+)-HM₃N, pET28a(+) -HNM.

9. A transformant comprising the expression vector according to claim 7.

10. The transformant according to claim 9, wherein the transformant is *E. coli* DH5α/HM₃Nm23 (Accession No. KCTC- 11380BP).

11. The transformant according to claim 9, wherein the transformant is *E. coli* DH5α/HNm23M₃ (Accession No. KCTC- 11381 BP).

12. A method of producing a cell permeable Nm23 recombinant protein comprising culturing the transformant according to claim 1 or 2.

13. The cell permeable Nm23 recombinant protein according to claim 1 or 2, further comprising: a nuclear localization sequence(NLS) and a histidine-tag affinity domain, said nuclear localization sequence and histidine-tag affinity domain being covalently coupled to one end of the recombinant protein.

14. The cell permeable Nm23 recombinant protein of claim 2 wherein the first and second MTDs comprise SEQ ID NO 8.

15. The cell permeable Nm23 recombinant protein according to claim 2, wherein the recombinant protein has an amino acid sequence of SEQ ID NO: 36.

16. A polynucleotide encoding the cell permeable Nm23 recombinant protein according to claim 2.

17. The polynucleotide according to claim 16, wherein the polynucleotide has a nucleotide sequence of SEQ ID NO: 35.

18. An expression vector comprising the polynucleotide according to claim 16.

19. The expression vector according to claim 18, wherein the expression vector is pET28(+)-HM₃NM₃.

20. A transformant comprising the expression vector according to claim 18.

21. A pharmaceutical composition comprising the cell permeable Nm23 recombinant protein according to claim 1 or 2 as an effective ingredient and a pharmaceutically acceptable carrier, which if effective for preventing metastasis by inhibiting proliferation, differentiation or migration of cancer cells.

* * * * *

SEQUENCE LISTING

```
<160> NUMBER OF SEQ ID NOS: 228

<210> SEQ ID NO 1
<211> LENGTH: 459
<212> TYPE: DNA
<213> ORGANISM: Homo sapiens
<220> FEATURE:
<223> OTHER INFORMATION: Human Nm23 cDNA sequence
<220> FEATURE:
<221> NAME/KEY: CDS
<222> LOCATION: (1)..(456)

<400> SEQUENCE: 1 atg gcc aac tgt gag cgt acc ttc att gcg atc aaa cca gat ggg gtc      48
Met Ala Asn Cys Glu Arg Thr Phe Ile Ala Ile Lys Pro Asp Gly Val
1               5                   10                  15 cag cgg ggt ctt gtg gga gag att atc aag cgt ttt gag cag aaa gga      96
Gln Arg Gly Leu Val Gly Glu Ile Ile Lys Arg Phe Glu Gln Lys Gly
            20                  25                  30 ttc cgc ctt gtt ggt ctg aaa ttc atg caa gct tcc gaa gat ctt ctc     144
Phe Arg Leu Val Gly Leu Lys Phe Met Gln Ala Ser Glu Asp Leu Leu
        35                  40                  45 aag gaa cac tac gtt gac ctg aag gac cgt cca ttc ttt gcc ggc ctg     192
Lys Glu His Tyr Val Asp Leu Lys Asp Arg Pro Phe Phe Ala Gly Leu
    50                  55                  60 gtg aaa tac atg cac tca ggg ccg gta gtt gcc atg gtc tgg gag ggg     240
Val Lys Tyr Met His Ser Gly Pro Val Val Ala Met Val Trp Glu Gly
65                  70                  75                  80 ctg aat gtg gtg aag acg ggc cga gtc atg ctc ggg gag acc aac cct     288
```

```
Leu Asn Val Val Lys Thr Gly Arg Val Met Leu Gly Glu Thr Asn Pro
                85                  90                  95 gca gac tcc aag cct ggg acc atc cgt gga gac ttc tgc ata caa gtt    336
Ala Asp Ser Lys Pro Gly Thr Ile Arg Gly Asp Phe Cys Ile Gln Val
            100                 105                 110 ggc agg aac att ata cat ggc agt gat tct gtg gag agt gca gag aag    384
Gly Arg Asn Ile Ile His Gly Ser Asp Ser Val Glu Ser Ala Glu Lys
        115                 120                 125 gag atc ggc ttg tgg ttt cac cct gag gaa ctg gta gat tac acg agc    432
Glu Ile Gly Leu Trp Phe His Pro Glu Glu Leu Val Asp Tyr Thr Ser
    130                 135                 140 tgt gct cag aac tgg atc tat gaa tga                                459
Cys Ala Gln Asn Trp Ile Tyr Glu
145                 150

<210> SEQ ID NO 2
<211> LENGTH: 152
<212> TYPE: PRT
<213> ORGANISM: Homo sapiens
<220> FEATURE:
<223> OTHER INFORMATION: Human Nm23 cDNA coded peptide sequence

<400> SEQUENCE: 2

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Gly Leu Trp Phe His Pro Glu Glu Leu Val Asp Tyr Thr Ser
    130                 135                 140

Cys Ala Gln Asn Trp Ile Tyr Glu
145                 150

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: kFGF-4 derived MTD cDNA sequence
<220> FEATURE:
<221> NAME/KEY: CDS
<222> LOCATION: (1)..(36)

<400> SEQUENCE: 3 gca gcc gtt ctt ctc cct gtt ctt ctt gcc gca ccc                    36
Ala Ala Val Leu Leu Pro Val Leu Leu Ala Ala Pro
1               5                   10
```

```
<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ala Val Leu Leu Pro Val Leu Leu Ala Ala Pro
1               5                   10

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JO-76 MTD cDNA sequence
<220> FEATURE:
<221> NAME/KEY: CDS
<222> LOCATION: (1)..(24)

<400> SEQUENCE: 5 gcg ctg gtg ctg ccg ctg gcg ccg                                         24
Ala Leu Val Leu Pro Leu Ala Pro
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Leu Val Leu Pro Leu Ala Pro
1               5

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: JO-77 MTD cDNA sequence
<220> FEATURE:
<221> NAME/KEY: CDS
<222> LOCATION: (1)..(27)

<400> SEQUENCE: 7 gcg gtg gcg ctg ctg att ctg gcg gtg                                     27
Ala Val Ala Leu Leu Ile Leu Ala Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Val Ala Leu Leu Ile Leu Ala Val
1               5
```

```
<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SV40 large T antigen-derived NLS
<220> FEATURE:
<221> NAME/KEY: CDS
<222> LOCATION: (1)..(15)

<400> SEQUENCE: 9 aag aag aag agg aag                                                     15
Lys Lys Lys Arg Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Lys Lys Arg Lys
1               5

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      HN-5' primer

<400> SEQUENCE: 11
ccgcatatgg ccaactgtga gcgtaccttc                                        30

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      HN-3' primer

<400> SEQUENCE: 12
ccgcatatgt cattcataga tccagttctg agc                                    33

<210> SEQ ID NO 13
<211> LENGTH: 72
<212> TYPE: DNA
<213> ORGANISM: Artificial Sequence
<220> FEATURE:
<223> OTHER INFORMATION: Description of Artificial Sequence: Synthetic
      HM1N-5' primer

<400> SEQUENCE: 13
ccgcatatgg cagccgttct tctccctgtt cttcttgccg cacccgccaa ctgtgagcgt       60
accttcattg cg                                                           72

<210> SEQ ID NO 14
<211> LENGTH: 72
<212> TYPE: DNA
```

```
<213> ORGANISM: Artificial Sequence
<220> FEATURE:
<223> OTHER INFORMATION: Description of Artificial Sequence: Synthetic
      HNM1-3' primer

<400> SEQUENCE: 14
ccgcatatgt cagggtgcgg caagaagaac agggagaaga acggctgctt catagatcca    60
gttctgagca ca                                                       72

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
      HM2N-5' primer

<400> SEQUENCE: 15
ccgcatatgg cgctggtgct gccgctggcg ccggccaact gtgagcgtac cttcattgcg    60

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      HNM2-3' primer

<400> SEQUENCE: 16
ccgcatatgt cacggcgcca gcggcagcac cagcgcttca tagatccagt tctgagcaca    60

<210> SEQ ID NO 17
<211> LENGTH: 63
<212> TYPE: DNA
<213> ORGANISM: Artificial Sequence
<220> FEATURE:
<223> OTHER INFORMATION: Description of Artificial Sequence: Synthetic
      HM3N-5' primer

<400> SEQUENCE: 17
ccgcatatgg cggtggcgct gctgattctg gcggtggcca actgtgagcg taccttcatt    60
gcg                                                                 63

<210> SEQ ID NO 18
<211> LENGTH: 63
<212> TYPE: DNA
<213> ORGANISM: Artificial Sequence
<220> FEATURE:
<223> OTHER INFORMATION: Description of Artificial Sequence: Synthetic
      HNM3-3' primer

<400> SEQUENCE: 18
ccgcatatgt cacaccgcca gaatcagcag cgccaccgct tcatagatcc agttctgagc    60
aca                                                                 63

<210> SEQ ID NO 19
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-Nm23 cDNA sequence
<220> FEATURE:
<221> NAME/KEY: CDS
<222> LOCATION: (1)..(516)
```

<400> SEQUENCE: 19

```
atg ggc agc agc cat cat cat cat cat cac agc agc ggc ctg gtg ccg    48
Met Gly Ser Ser His His His His His His Ser Ser Gly Leu Val Pro
1               5                  10                  15 cgc ggc agc cat atg gcc aac tgt gag cgt acc ttc att gcg atc aaa    96
Arg Gly Ser His Met Ala Asn Cys Glu Arg Thr Phe Ile Ala Ile Lys
            20                  25                  30 cca gat ggg gtc cag cgg ggt ctt gtg gga gag att atc aag cgt ttt   144
Pro Asp Gly Val Gln Arg Gly Leu Val Gly Glu Ile Ile Lys Arg Phe
        35                  40                  45 gag cag aaa gga ttc cgc ctt gtt ggt ctg aaa ttc atg caa gct tcc   192
Glu Gln Lys Gly Phe Arg Leu Val Gly Leu Lys Phe Met Gln Ala Ser
    50                  55                  60 gaa gat ctt ctc aag gaa cac tac gtt gac ctg aag gac cgt cca ttc   240
Glu Asp Leu Leu Lys Glu His Tyr Val Asp Leu Lys Asp Arg Pro Phe
65                  70                  75                  80 ttt gcc ggc ctg gtg aaa tac atg cac tca ggg ccg gta gtt gcc atg   288
Phe Ala Gly Leu Val Lys Tyr Met His Ser Gly Pro Val Val Ala Met
                85                  90                  95 gtc tgg gag ggg ctg aat gtg gtg aag acg ggc cga gtc atg ctc ggg   336
Val Trp Glu Gly Leu Asn Val Val Lys Thr Gly Arg Val Met Leu Gly
            100                 105                 110 gag acc aac cct gca gac tcc aag cct ggg acc atc cgt gga gac ttc   384
Glu Thr Asn Pro Ala Asp Ser Lys Pro Gly Thr Ile Arg Gly Asp Phe
        115                 120                 125 tgc ata caa gtt ggc agg aac att ata cat ggc agt gat tct gtg gag   432
Cys Ile Gln Val Gly Arg Asn Ile Ile His Gly Ser Asp Ser Val Glu
    130                 135                 140 agt gca gag aag gag atc ggc ttg tgg ttt cac cct gag gaa ctg gta   480
Ser Ala Glu Lys Glu Ile Gly Leu Trp Phe His Pro Glu Glu Leu Val
145                 150                 155                 160 gat tac acg agc tgt gct cag aac tgg atc tat gaa tga               519
Asp Tyr Thr Ser Cys Ala Gln Asn Trp Ile Tyr Glu
                165                 170
```

<210> SEQ ID NO 20
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Gly Ser Ser His His His His His His Ser Ser Gly Leu Val Pro
1               5                  10                  15

Arg Gly Ser His Met Ala Asn Cys Glu Arg Thr Phe Ile Ala Ile Lys
            20                  25                  30

Pro Asp Gly Val Gln Arg Gly Leu Val Gly Glu Ile Ile Lys Arg Phe
        35                  40                  45

Glu Gln Lys Gly Phe Arg Leu Val Gly Leu Lys Phe Met Gln Ala Ser
    50                  55                  60

Glu Asp Leu Leu Lys Glu His Tyr Val Asp Leu Lys Asp Arg Pro Phe
65                  70                  75                  80

Phe Ala Gly Leu Val Lys Tyr Met His Ser Gly Pro Val Val Ala Met
                85                  90                  95

Val Trp Glu Gly Leu Asn Val Val Lys Thr Gly Arg Val Met Leu Gly
            100                 105                 110

Glu Thr Asn Pro Ala Asp Ser Lys Pro Gly Thr Ile Arg Gly Asp Phe
```

```
                        115                 120                 125
Cys Ile Gln Val Gly Arg Asn Ile Ile His Gly Ser Asp Ser Val Glu
            130                 135                 140

Ser Ala Glu Lys Glu Ile Gly Leu Trp Phe His Pro Glu Glu Leu Val
145                 150                 155                 160

Asp Tyr Thr Ser Cys Ala Gln Asn Trp Ile Tyr Glu
                165                 170

<210> SEQ ID NO 21
<211> LENGTH: 555
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-MTD1-Nm23 cDNA sequence
<220> FEATURE:
<221> NAME/KEY: CDS
<222> LOCATION: (1)..(552)

<400> SEQUENCE: 21 atg ggc agc agc cat cat cat cat cat cac agc agc ggc ctg gtg ccg       48
Met Gly Ser Ser His His His His His His Ser Ser Gly Leu Val Pro
1               5                   10                  15 cgc ggc agc cat atg gca gcc gtt ctt ctc cct gtt ctt ctt gcc gca       96
Arg Gly Ser His Met Ala Ala Val Leu Leu Pro Val Leu Leu Ala Ala
            20                  25                  30 ccc gcc aac tgt gag cgt acc ttc att gcg atc aaa cca gat ggg gtc      144
Pro Ala Asn Cys Glu Arg Thr Phe Ile Ala Ile Lys Pro Asp Gly Val
        35                  40                  45 cag cgg ggt ctt gtg gga gag att atc aag cgt ttt gag cag aaa gga      192
Gln Arg Gly Leu Val Gly Glu Ile Ile Lys Arg Phe Glu Gln Lys Gly
    50                  55                  60 ttc cgc ctt gtt ggt ctg aaa ttc atg caa gct tcc gaa gat ctt ctc      240
Phe Arg Leu Val Gly Leu Lys Phe Met Gln Ala Ser Glu Asp Leu Leu
65                  70                  75                  80 aag gaa cac tac gtt gac ctg aag gac cgt cca ttc ttt gcc ggc ctg      288
Lys Glu His Tyr Val Asp Leu Lys Asp Arg Pro Phe Phe Ala Gly Leu
                85                  90                  95 gtg aaa tac atg cac tca ggg ccg gta gtt gcc atg gtc tgg gag ggg      336
Val Lys Tyr Met His Ser Gly Pro Val Val Ala Met Val Trp Glu Gly
            100                 105                 110 ctg aat gtg gtg aag acg ggc cga gtc atg ctc ggg gag acc aac cct      384
Leu Asn Val Val Lys Thr Gly Arg Val Met Leu Gly Glu Thr Asn Pro
        115                 120                 125 gca gac tcc aag cct ggg acc atc cgt gga gac ttc tgc ata caa gtt      432
Ala Asp Ser Lys Pro Gly Thr Ile Arg Gly Asp Phe Cys Ile Gln Val
    130                 135                 140 ggc agg aac att ata cat ggc agt gat tct gtg gag agt gca gag aag      480
Gly Arg Asn Ile Ile His Gly Ser Asp Ser Val Glu Ser Ala Glu Lys
145                 150                 155                 160 gag atc ggc ttg tgg ttt cac cct gag gaa ctg gta gat tac acg agc      528
Glu Ile Gly Leu Trp Phe His Pro Glu Glu Leu Val Asp Tyr Thr Ser
                165                 170                 175 tgt gct cag aac tgg atc tat gaa tga                                  555
Cys Ala Gln Asn Trp Ile Tyr Glu
            180

<210> SEQ ID NO 22
<211> LENGTH: 184
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 22

Met Gly Ser Ser His His His His His His Ser Ser Gly Leu Val Pro
1               5                   10                  15

Arg Gly Ser His Met Ala Ala Val Leu Leu Pro Val Leu Leu Ala Ala
            20                  25                  30

Pro Ala Asn Cys Glu Arg Thr Phe Ile Ala Ile Lys Pro Asp Gly Val
        35                  40                  45

Gln Arg Gly Leu Val Gly Glu Ile Ile Lys Arg Phe Glu Gln Lys Gly
50                  55                  60

Phe Arg Leu Val Gly Leu Lys Phe Met Gln Ala Ser Glu Asp Leu Leu
65                  70                  75                  80

Lys Glu His Tyr Val Asp Leu Lys Asp Arg Pro Phe Phe Ala Gly Leu
                85                  90                  95

Val Lys Tyr Met His Ser Gly Pro Val Val Ala Met Val Trp Glu Gly
            100                 105                 110

Leu Asn Val Val Lys Thr Gly Arg Val Met Leu Gly Glu Thr Asn Pro
        115                 120                 125

Ala Asp Ser Lys Pro Gly Thr Ile Arg Gly Asp Phe Cys Ile Gln Val
    130                 135                 140

Gly Arg Asn Ile Ile His Gly Ser Asp Ser Val Glu Ser Ala Glu Lys
145                 150                 155                 160

Glu Ile Gly Leu Trp Phe His Pro Glu Glu Leu Val Asp Tyr Thr Ser
                165                 170                 175

Cys Ala Gln Asn Trp Ile Tyr Glu
            180

<210> SEQ ID NO 23
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-Nm23-MTD1 cDNA sequence
<220> FEATURE:
<221> NAME/KEY: CDS
<222> LOCATION: (1)..(516)

<400> SEQUENCE: 23 atg ggc agc agc cat cat cat cat cat cac agc agc ggc ctg gtg ccg    48
Met Gly Ser Ser His His His His His His Ser Ser Gly Leu Val Pro
1               5                   10                  15 cgc ggc agc cat atg gcc aac tgt gag cgt acc ttc att gcg atc aaa    96
Arg Gly Ser His Met Ala Asn Cys Glu Arg Thr Phe Ile Ala Ile Lys
            20                  25                  30 cca gat ggg gtc cag cgg ggt ctt gtg gga gag att atc aag cgt ttt   144
Pro Asp Gly Val Gln Arg Gly Leu Val Gly Glu Ile Ile Lys Arg Phe
        35                  40                  45 gag cag aaa gga ttc cgc ctt gtt ggt ctg aaa ttc atg caa gct tcc   192
Glu Gln Lys Gly Phe Arg Leu Val Gly Leu Lys Phe Met Gln Ala Ser
50                  55                  60 gaa gat ctt ctc aag gaa cac tac gtt gac ctg aag gac cgt cca ttc   240
Glu Asp Leu Leu Lys Glu His Tyr Val Asp Leu Lys Asp Arg Pro Phe
65                  70                  75                  80 ttt gcc ggc ctg gtg aaa tac atg cac tca ggg ccg gta gtt gcc atg   288
Phe Ala Gly Leu Val Lys Tyr Met His Ser Gly Pro Val Val Ala Met

```
                            85                  90                  95
gtc tgg gag ggg ctg aat gtg gtg aag acg ggc cga gtc atg ctc ggg      336
Val Trp Glu Gly Leu Asn Val Val Lys Thr Gly Arg Val Met Leu Gly
                100                 105                 110 gag acc aac cct gca gac tcc aag cct ggg acc atc cgt gga gac ttc      384
Glu Thr Asn Pro Ala Asp Ser Lys Pro Gly Thr Ile Arg Gly Asp Phe
            115                 120                 125 tgc ata caa gtt ggc agg aac att ata cat ggc agt gat tct gtg gag      432
Cys Ile Gln Val Gly Arg Asn Ile Ile His Gly Ser Asp Ser Val Glu
        130                 135                 140 agt gca gag aag gag atc ggc ttg tgg ttt cac cct gag gaa ctg gta      480
Ser Ala Glu Lys Glu Ile Gly Leu Trp Phe His Pro Glu Glu Leu Val
145                 150                 155                 160 gat tac acg agc tgt gct cag aac tgg atc tat gaa tgagcagccg           526
Asp Tyr Thr Ser Cys Ala Gln Asn Trp Ile Tyr Glu
                165                 170 ttcttctccc tgttcttctt gccgcaccct ga                                  558

<210> SEQ ID NO 24
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Ser Ser His His His His His His Ser Ser Gly Leu Val Pro
1               5                   10                  15

Arg Gly Ser His Met Ala Asn Cys Glu Arg Thr Phe Ile Ala Ile Lys
            20                  25                  30

Pro Asp Gly Val Gln Arg Gly Leu Val Gly Glu Ile Ile Lys Arg Phe
        35                  40                  45

Glu Gln Lys Gly Phe Arg Leu Val Gly Leu Lys Phe Met Gln Ala Ser
    50                  55                  60

Glu Asp Leu Leu Lys Glu His Tyr Val Asp Leu Lys Asp Arg Pro Phe
65                  70                  75                  80

Phe Ala Gly Leu Val Lys Tyr Met His Ser Gly Pro Val Val Ala Met
                85                  90                  95

Val Trp Glu Gly Leu Asn Val Val Lys Thr Gly Arg Val Met Leu Gly
            100                 105                 110

Glu Thr Asn Pro Ala Asp Ser Lys Pro Gly Thr Ile Arg Gly Asp Phe
        115                 120                 125

Cys Ile Gln Val Gly Arg Asn Ile Ile His Gly Ser Asp Ser Val Glu
    130                 135                 140

Ser Ala Glu Lys Glu Ile Gly Leu Trp Phe His Pro Glu Glu Leu Val
145                 150                 155                 160

Asp Tyr Thr Ser Cys Ala Gln Asn Trp Ile Tyr Glu
                165                 170

<210> SEQ ID NO 25
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-MTD1-Nm23-MTD1 cDNA sequence
<220> FEATURE:
<221> NAME/KEY: CDS
```

<222> LOCATION: (1)..(588)

<400> SEQUENCE: 25

```
atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg gca gcc gtt ctt ctc cct gtt ctt ctt gcc gca      96
Arg Gly Ser His Met Ala Ala Val Leu Leu Pro Val Leu Leu Ala Ala
                20                  25                  30 ccc gcc aac tgt gag cgt acc ttc att gcg atc aaa cca gat ggg gtc     144
Pro Ala Asn Cys Glu Arg Thr Phe Ile Ala Ile Lys Pro Asp Gly Val
            35                  40                  45 cag cgg ggt ctt gtg gga gag att atc aag cgt ttt gag cag aaa gga     192
Gln Arg Gly Leu Val Gly Glu Ile Ile Lys Arg Phe Glu Gln Lys Gly
        50                  55                  60 ttc cgc ctt gtt ggt ctg aaa ttc atg caa gct tcc gaa gat ctt ctc     240
Phe Arg Leu Val Gly Leu Lys Phe Met Gln Ala Ser Glu Asp Leu Leu
65                  70                  75                  80 aag gaa cac tac gtt gac ctg aag gac cgt cca ttc ttt gcc ggc ctg     288
Lys Glu His Tyr Val Asp Leu Lys Asp Arg Pro Phe Phe Ala Gly Leu
                85                  90                  95 gtg aaa tac atg cac tca ggg ccg gta gtt gcc atg gtc tgg gag ggg     336
Val Lys Tyr Met His Ser Gly Pro Val Val Ala Met Val Trp Glu Gly
            100                 105                 110 ctg aat gtg gtg aag acg ggc cga gtc atg ctc ggg gag acc aac cct     384
Leu Asn Val Val Lys Thr Gly Arg Val Met Leu Gly Glu Thr Asn Pro
        115                 120                 125 gca gac tcc aag cct ggg acc atc cgt gga gac ttc tgc ata caa gtt     432
Ala Asp Ser Lys Pro Gly Thr Ile Arg Gly Asp Phe Cys Ile Gln Val
    130                 135                 140 ggc agg aac att ata cat ggc agt gat tct gtg gag agt gca gag aag     480
Gly Arg Asn Ile Ile His Gly Ser Asp Ser Val Glu Ser Ala Glu Lys
145                 150                 155                 160 gag atc ggc ttg tgg ttt cac cct gag gaa ctg gta gat tac acg agc     528
Glu Ile Gly Leu Trp Phe His Pro Glu Glu Leu Val Asp Tyr Thr Ser
                165                 170                 175 tgt gct cag aac tgg atc tat gaa gca gcc gtt ctt ctc cct gtt ctt     576
Cys Ala Gln Asn Trp Ile Tyr Glu Ala Ala Val Leu Leu Pro Val Leu
            180                 185                 190 ctt gcc gca ccc tga                                                 591
Leu Ala Ala Pro
        195
```

<210> SEQ ID NO 26
<211> LENGTH: 196
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Gly Ser Ser His His His His His His Ser Ser Gly Leu Val Pro
1               5                   10                  15

Arg Gly Ser His Met Ala Ala Val Leu Leu Pro Val Leu Leu Ala Ala
                20                  25                  30

Pro Ala Asn Cys Glu Arg Thr Phe Ile Ala Ile Lys Pro Asp Gly Val
            35                  40                  45

Gln Arg Gly Leu Val Gly Glu Ile Ile Lys Arg Phe Glu Gln Lys Gly
        50                  55                  60

Phe Arg Leu Val Gly Leu Lys Phe Met Gln Ala Ser Glu Asp Leu Leu
```

```
                65                  70                  75                  80
Lys Glu His Tyr Val Asp Leu Lys Asp Arg Pro Phe Phe Ala Gly Leu
                    85                  90                  95

Val Lys Tyr Met His Ser Gly Pro Val Val Ala Met Val Trp Glu Gly
                100                 105                 110

Leu Asn Val Val Lys Thr Gly Arg Val Met Leu Gly Glu Thr Asn Pro
                115                 120                 125

Ala Asp Ser Lys Pro Gly Thr Ile Arg Gly Asp Phe Cys Ile Gln Val
            130                 135                 140

Gly Arg Asn Ile Ile His Gly Ser Asp Ser Val Glu Ser Ala Glu Lys
145                 150                 155                 160

Glu Ile Gly Leu Trp Phe His Pro Glu Glu Leu Val Asp Tyr Thr Ser
                165                 170                 175

Cys Ala Gln Asn Trp Ile Tyr Glu Ala Ala Val Leu Leu Pro Val Leu
                180                 185                 190

Leu Ala Ala Pro
        195

<210> SEQ ID NO 27
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-MTD2-Nm23 cDNA sequence
<220> FEATURE:
<221> NAME/KEY: CDS
<222> LOCATION: (1)..(540)

<400> SEQUENCE: 27 atg ggc agc agc cat cat cat cat cac agc agc ggc ctg gtg ccg        48
Met Gly Ser Ser His His His His His His Ser Ser Gly Leu Val Pro
1               5                   10                  15 cgc ggc agc cat atg gcg ctg gtg ctg ccg ctg gcg ccg gcc aac tgt    96
Arg Gly Ser His Met Ala Leu Val Leu Pro Leu Ala Pro Ala Asn Cys
                20                  25                  30 gag cgt acc ttc att gcg atc aaa cca gat ggg gtc cag cgg ggt ctt    144
Glu Arg Thr Phe Ile Ala Ile Lys Pro Asp Gly Val Gln Arg Gly Leu
            35                  40                  45 gtg gga gag att atc aag cgt ttt gag cag aaa gga ttc cgc ctt gtt    192
Val Gly Glu Ile Ile Lys Arg Phe Glu Gln Lys Gly Phe Arg Leu Val
        50                  55                  60 ggt ctg aaa ttc atg caa gct tcc gaa gat ctt ctc aag gaa cac tac    240
Gly Leu Lys Phe Met Gln Ala Ser Glu Asp Leu Leu Lys Glu His Tyr
65                  70                  75                  80 gtt gac ctg aag gac cgt cca ttc ttt gcc ggc ctg gtg aaa tac atg    288
Val Asp Leu Lys Asp Arg Pro Phe Phe Ala Gly Leu Val Lys Tyr Met
                85                  90                  95 cac tca ggg ccg gta gtt gcc atg gtc tgg gag ggg ctg aat gtg gtg    336
His Ser Gly Pro Val Val Ala Met Val Trp Glu Gly Leu Asn Val Val
                100                 105                 110 aag acg ggc cga gtc atg ctc ggg gag acc aac cct gca gac tcc aag    384
Lys Thr Gly Arg Val Met Leu Gly Glu Thr Asn Pro Ala Asp Ser Lys
            115                 120                 125 cct ggg acc atc cgt gga gac ttc tgc ata caa gtt ggc agg aac att    432
Pro Gly Thr Ile Arg Gly Asp Phe Cys Ile Gln Val Gly Arg Asn Ile
        130                 135                 140 ata cat ggc agt gat tct gtg gag agt gca gag aag gag atc ggc ttg    480
Ile His Gly Ser Asp Ser Val Glu Ser Ala Glu Lys Glu Ile Gly Leu
```

```
                      145                 150                 155                 160
tgg ttt cac cct gag gaa ctg gta gat tac acg agc tgt gct cag aac     528
Trp Phe His Pro Glu Glu Leu Val Asp Tyr Thr Ser Cys Ala Gln Asn
                      165                 170                 175 tgg atc tat gaa tga                                                 543
Trp Ile Tyr Glu
        180

<210> SEQ ID NO 28
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Ser Ser His His His His His His Ser Ser Gly Leu Val Pro
1               5                   10                  15

Arg Gly Ser His Met Ala Leu Val Leu Pro Leu Ala Pro Ala Asn Cys
            20                  25                  30

Glu Arg Thr Phe Ile Ala Ile Lys Pro Asp Gly Val Gln Arg Gly Leu
        35                  40                  45

Val Gly Glu Ile Ile Lys Arg Phe Glu Gln Lys Gly Phe Arg Leu Val
    50                  55                  60

Gly Leu Lys Phe Met Gln Ala Ser Glu Asp Leu Leu Lys Glu His Tyr
65                  70                  75                  80

Val Asp Leu Lys Asp Arg Pro Phe Phe Ala Gly Leu Val Lys Tyr Met
                85                  90                  95

His Ser Gly Pro Val Val Ala Met Val Trp Glu Gly Leu Asn Val Val
            100                 105                 110

Lys Thr Gly Arg Val Met Leu Gly Glu Thr Asn Pro Ala Asp Ser Lys
        115                 120                 125

Pro Gly Thr Ile Arg Gly Asp Phe Cys Ile Gln Val Gly Arg Asn Ile
    130                 135                 140

Ile His Gly Ser Asp Ser Val Glu Ser Ala Glu Lys Glu Ile Gly Leu
145                 150                 155                 160

Trp Phe His Pro Glu Glu Leu Val Asp Tyr Thr Ser Cys Ala Gln Asn
                165                 170                 175

Trp Ile Tyr Glu
        180

<210> SEQ ID NO 29
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-Nm23-MTD2 cDNA sequence
<220> FEATURE:
<221> NAME/KEY: CDS
<222> LOCATION: (1)..(540)

<400> SEQUENCE: 29 atg ggc agc agc cat cat cat cat cat cac agc agc ggc ctg gtg ccg     48
Met Gly Ser Ser His His His His His His Ser Ser Gly Leu Val Pro
1               5                   10                  15 cgc ggc agc cat atg gcc aac tgt gag cgt acc ttc att gcg atc aaa     96
Arg Gly Ser His Met Ala Asn Cys Glu Arg Thr Phe Ile Ala Ile Lys
            20                  25                  30
```

```
cca gat ggg gtc cag cgg ggt ctt gtg gga gag att atc aag cgt ttt      144
Pro Asp Gly Val Gln Arg Gly Leu Val Gly Glu Ile Ile Lys Arg Phe
         35                  40                  45 gag cag aaa gga ttc cgc ctt gtt ggt ctg aaa ttc atg caa gct tcc      192
Glu Gln Lys Gly Phe Arg Leu Val Gly Leu Lys Phe Met Gln Ala Ser
 50                  55                  60 gaa gat ctt ctc aag gaa cac tac gtt gac ctg aag gac cgt cca ttc      240
Glu Asp Leu Leu Lys Glu His Tyr Val Asp Leu Lys Asp Arg Pro Phe
65                  70                  75                  80 ttt gcc ggc ctg gtg aaa tac atg cac tca ggg ccg gta gtt gcc atg      288
Phe Ala Gly Leu Val Lys Tyr Met His Ser Gly Pro Val Val Ala Met
                 85                  90                  95 gtc tgg gag ggg ctg aat gtg gtg aag acg ggc cga gtc atg ctc ggg      336
Val Trp Glu Gly Leu Asn Val Val Lys Thr Gly Arg Val Met Leu Gly
            100                 105                 110 gag acc aac cct gca gac tcc aag cct ggg acc atc cgt gga gac ttc      384
Glu Thr Asn Pro Ala Asp Ser Lys Pro Gly Thr Ile Arg Gly Asp Phe
        115                 120                 125 tgc ata caa gtt ggc agg aac att ata cat ggc agt gat tct gtg gag      432
Cys Ile Gln Val Gly Arg Asn Ile Ile His Gly Ser Asp Ser Val Glu
    130                 135                 140 agt gca gag aag gag atc ggc ttg tgg ttt cac cct gag gaa ctg gta      480
Ser Ala Glu Lys Glu Ile Gly Leu Trp Phe His Pro Glu Glu Leu Val
145                 150                 155                 160 gat tac acg agc tgt gct cag aac tgg atc tat gaa gcg ctg gtg ctg      528
Asp Tyr Thr Ser Cys Ala Gln Asn Trp Ile Tyr Glu Ala Leu Val Leu
                165                 170                 175 ccg ctg gcg ccg tga                                                  543
Pro Leu Ala Pro
            180

<210> SEQ ID NO 30
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Ser Ser His His His His His His Ser Ser Gly Leu Val Pro
1               5                   10                  15

Arg Gly Ser His Met Ala Asn Cys Glu Arg Thr Phe Ile Ala Ile Lys
            20                  25                  30

Pro Asp Gly Val Gln Arg Gly Leu Val Gly Glu Ile Ile Lys Arg Phe
        35                  40                  45

Glu Gln Lys Gly Phe Arg Leu Val Gly Leu Lys Phe Met Gln Ala Ser
    50                  55                  60

Glu Asp Leu Leu Lys Glu His Tyr Val Asp Leu Lys Asp Arg Pro Phe
65                  70                  75                  80

Phe Ala Gly Leu Val Lys Tyr Met His Ser Gly Pro Val Val Ala Met
                85                  90                  95

Val Trp Glu Gly Leu Asn Val Val Lys Thr Gly Arg Val Met Leu Gly
            100                 105                 110

Glu Thr Asn Pro Ala Asp Ser Lys Pro Gly Thr Ile Arg Gly Asp Phe
        115                 120                 125

Cys Ile Gln Val Gly Arg Asn Ile Ile His Gly Ser Asp Ser Val Glu
    130                 135                 140

Ser Ala Glu Lys Glu Ile Gly Leu Trp Phe His Pro Glu Glu Leu Val
```

```
                    145                 150                 155                 160
Asp Tyr Thr Ser Cys Ala Gln Asn Trp Ile Tyr Glu Ala Leu Val Leu
                165                 170                 175

Pro Leu Ala Pro
            180

<210> SEQ ID NO 31
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-MTD3-Nm23 cDNA sequence
<220> FEATURE:
<221> NAME/KEY: CDS
<222> LOCATION: (1)..(543)

<400> SEQUENCE: 31 atg ggc agc agc cat cat cat cat cat cac agc agc ggc ctg gtg ccg       48
Met Gly Ser Ser His His His His His His Ser Ser Gly Leu Val Pro
1               5                   10                  15 cgc ggc agc cat atg gcg gtg gcg ctg ctg att ctg gcg gtg gcc aac       96
Arg Gly Ser His Met Ala Val Ala Leu Leu Ile Leu Ala Val Ala Asn
            20                  25                  30 tgt gag cgt acc ttc att gcg atc aaa cca gat ggg gtc cag cgg ggt      144
Cys Glu Arg Thr Phe Ile Ala Ile Lys Pro Asp Gly Val Gln Arg Gly
        35                  40                  45 ctt gtg gga gag att atc aag cgt ttt gag cag aaa gga ttc gcc ctt      192
Leu Val Gly Glu Ile Ile Lys Arg Phe Glu Gln Lys Gly Phe Arg Leu
    50                  55                  60 gtt ggt ctg aaa ttc atg caa gct tcc gaa gat ctt ctc aag gaa cac      240
Val Gly Leu Lys Phe Met Gln Ala Ser Glu Asp Leu Leu Lys Glu His
65                  70                  75                  80 tac gtt gac ctg aag gac cgt cca ttc ttt gcc ggc ctg gtg aaa tac      288
Tyr Val Asp Leu Lys Asp Arg Pro Phe Phe Ala Gly Leu Val Lys Tyr
                85                  90                  95 atg cac tca ggg ccg gta gtt gcc atg gtc tgg gag ggg ctg aat gtg      336
Met His Ser Gly Pro Val Val Ala Met Val Trp Glu Gly Leu Asn Val
            100                 105                 110 gtg aag acg ggc cga gtc atg ctc ggg gag acc aac cct gca gac tcc      384
Val Lys Thr Gly Arg Val Met Leu Gly Glu Thr Asn Pro Ala Asp Ser
        115                 120                 125 aag cct ggg acc atc cgt gga gac ttc tgc ata caa gtt ggc agg aac      432
Lys Pro Gly Thr Ile Arg Gly Asp Phe Cys Ile Gln Val Gly Arg Asn
    130                 135                 140 att ata cat ggc agt gat tct gtg gag agt gca gag aag gag atc ggc      480
Ile Ile His Gly Ser Asp Ser Val Glu Ser Ala Glu Lys Glu Ile Gly
145                 150                 155                 160 ttg tgg ttt cac cct gag gaa ctg gta gat tac acg agc tgt gct cag      528
Leu Trp Phe His Pro Glu Glu Leu Val Asp Tyr Thr Ser Cys Ala Gln
                165                 170                 175 aac tgg atc tat gaa tga                                              546
Asn Trp Ile Tyr Glu
            180

<210> SEQ ID NO 32
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 32

| Met | Gly | Ser | Ser | His | His | His | His | His | Ser | Ser | Gly | Leu | Val | Pro |
|---|---|---|---|---|---|---|---|---|---|---|---|---|---|---|
| 1 | | | | 5 | | | | | 10 | | | | | 15 |

| Arg | Gly | Ser | His | Met | Ala | Val | Ala | Leu | Leu | Ile | Leu | Ala | Val | Ala | Asn |
|---|---|---|---|---|---|---|---|---|---|---|---|---|---|---|---|
| | | | 20 | | | | | 25 | | | | | 30 | | |

| Cys | Glu | Arg | Thr | Phe | Ile | Ala | Ile | Lys | Pro | Asp | Gly | Val | Gln | Arg | Gly |
|---|---|---|---|---|---|---|---|---|---|---|---|---|---|---|---|
| | | 35 | | | | | 40 | | | | | 45 | | | |

| Leu | Val | Gly | Glu | Ile | Ile | Lys | Arg | Phe | Glu | Gln | Lys | Gly | Phe | Arg | Leu |
|---|---|---|---|---|---|---|---|---|---|---|---|---|---|---|---|
| | 50 | | | | | 55 | | | | | 60 | | | | |

| Val | Gly | Leu | Lys | Phe | Met | Gln | Ala | Ser | Glu | Asp | Leu | Leu | Lys | Glu | His |
|---|---|---|---|---|---|---|---|---|---|---|---|---|---|---|---|
| 65 | | | | | 70 | | | | | 75 | | | | | 80 |

| Tyr | Val | Asp | Leu | Lys | Asp | Arg | Pro | Phe | Phe | Ala | Gly | Leu | Val | Lys | Tyr |
|---|---|---|---|---|---|---|---|---|---|---|---|---|---|---|---|
| | | | | 85 | | | | | 90 | | | | | 95 | |

| Met | His | Ser | Gly | Pro | Val | Val | Ala | Met | Val | Trp | Glu | Gly | Leu | Asn | Val |
|---|---|---|---|---|---|---|---|---|---|---|---|---|---|---|---|
| | | | | 100 | | | | | 105 | | | | | 110 | |

| Val | Lys | Thr | Gly | Arg | Val | Met | Leu | Gly | Glu | Thr | Asn | Pro | Ala | Asp | Ser |
|---|---|---|---|---|---|---|---|---|---|---|---|---|---|---|---|
| | | | 115 | | | | | 120 | | | | | 125 | | |

| Lys | Pro | Gly | Thr | Ile | Arg | Gly | Asp | Phe | Cys | Ile | Gln | Val | Gly | Arg | Asn |
|---|---|---|---|---|---|---|---|---|---|---|---|---|---|---|---|
| | 130 | | | | | 135 | | | | | 140 | | | | |

| Ile | Ile | His | Gly | Ser | Asp | Ser | Val | Glu | Ser | Ala | Glu | Lys | Glu | Ile | Gly |
|---|---|---|---|---|---|---|---|---|---|---|---|---|---|---|---|
| 145 | | | | | 150 | | | | | 155 | | | | | 160 |

| Leu | Trp | Phe | His | Pro | Glu | Glu | Leu | Val | Asp | Tyr | Thr | Ser | Cys | Ala | Gln |
|---|---|---|---|---|---|---|---|---|---|---|---|---|---|---|---|
| | | | | 165 | | | | | 170 | | | | | 175 | |

| Asn | Trp | Ile | Tyr | Glu |
|---|---|---|---|---|
| | | | | 180 |

<210> SEQ ID NO 33
<211> LENGTH: 546
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: His-Nm23-MTD3 cDNA sequence
<220> FEATURE:
<221> NAME/KEY: CDS
<222> LOCATION: (1)..(543)

<400> SEQUENCE: 33

| atg | ggc | agc | agc | cat | cat | cat | cat | cat | cac | agc | agc | ggc | ctg | gtg | ccg | 48 |
|---|---|---|---|---|---|---|---|---|---|---|---|---|---|---|---|---|
| Met | Gly | Ser | Ser | His | His | His | His | His | His | Ser | Ser | Gly | Leu | Val | Pro | |
| 1 | | | | 5 | | | | | 10 | | | | | 15 | | |

| cgc | ggc | agc | cat | atg | gcc | aac | tgt | gag | cgt | acc | ttc | att | gcg | atc | aaa | 96 |
|---|---|---|---|---|---|---|---|---|---|---|---|---|---|---|---|---|
| Arg | Gly | Ser | His | Met | Ala | Asn | Cys | Glu | Arg | Thr | Phe | Ile | Ala | Ile | Lys | |
| | | | 20 | | | | | 25 | | | | | 30 | | | |

| cca | gat | ggg | gtc | cag | cgg | ggt | ctt | gtg | gga | gag | att | atc | aag | cgt | ttt | 144 |
|---|---|---|---|---|---|---|---|---|---|---|---|---|---|---|---|---|
| Pro | Asp | Gly | Val | Gln | Arg | Gly | Leu | Val | Gly | Glu | Ile | Ile | Lys | Arg | Phe | |
| | | 35 | | | | | 40 | | | | | 45 | | | | |

| gag | cag | aaa | gga | ttc | cgc | ctt | gtt | ggt | ctg | aaa | ttc | atg | caa | gct | tcc | 192 |
|---|---|---|---|---|---|---|---|---|---|---|---|---|---|---|---|---|
| Glu | Gln | Lys | Gly | Phe | Arg | Leu | Val | Gly | Leu | Lys | Phe | Met | Gln | Ala | Ser | |
| | 50 | | | | | 55 | | | | | 60 | | | | | |

| gaa | gat | ctt | ctc | aag | gaa | cac | tac | gtt | gac | ctg | aag | gac | cgt | cca | ttc | 240 |
|---|---|---|---|---|---|---|---|---|---|---|---|---|---|---|---|---|
| Glu | Asp | Leu | Leu | Lys | Glu | His | Tyr | Val | Asp | Leu | Lys | Asp | Arg | Pro | Phe | |
| 65 | | | | | 70 | | | | | 75 | | | | | 80 | |

| ttt | gcc | ggc | ctg | gtg | aaa | tac | atg | cac | tca | ggg | ccg | gta | gtt | gcc | atg | 288 |
|---|---|---|---|---|---|---|---|---|---|---|---|---|---|---|---|---|
| Phe | Ala | Gly | Leu | Val | Lys | Tyr | Met | His | Ser | Gly | Pro | Val | Val | Ala | Met | |
| | | | | 85 | | | | | 90 | | | | | 95 | | |

| gtc | tgg | gag | ggg | ctg | aat | gtg | gtg | aag | acg | ggc | cga | gtc | atg | ctc | ggg | 336 |

```
                                                                                      384
gag acc aac cct gca gac tcc aag cct ggg acc atc cgt gga gac ttc
Glu Thr Asn Pro Ala Asp Ser Lys Pro Gly Thr Ile Arg Gly Asp Phe
            115                 120                 125

432
tgc ata caa gtt ggc agg aac att ata cat ggc agt gat tct gtg gag
Cys Ile Gln Val Gly Arg Asn Ile Ile His Gly Ser Asp Ser Val Glu
130                 135                 140

480
agt gca gag aag gag atc ggc ttg tgg ttt cac cct gag gaa ctg gta
Ser Ala Glu Lys Glu Ile Gly Leu Trp Phe His Pro Glu Glu Leu Val
145                 150                 155                 160

528
gat tac acg agc tgt gct cag aac tgg atc tat gaa gcg gtg gcg ctg
Asp Tyr Thr Ser Cys Ala Gln Asn Trp Ile Tyr Glu Ala Val Ala Leu
            165                 170                 175

546
ctg att ctg gcg gtg tga
Leu Ile Leu Ala Val
            180
```

Val Trp Glu Gly Leu Asn Val Val Lys Thr Gly Arg Val Met Leu Gly
            100                 105                 110

<210> SEQ ID NO 34
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gly Ser Ser His His His His His His Ser Ser Gly Leu Val Pro
1               5                   10                  15

Arg Gly Ser His Met Ala Asn Cys Glu Arg Thr Phe Ile Ala Ile Lys
            20                  25                  30

Pro Asp Gly Val Gln Arg Gly Leu Val Gly Glu Ile Ile Lys Arg Phe
        35                  40                  45

Glu Gln Lys Gly Phe Arg Leu Val Gly Leu Lys Phe Met Gln Ala Ser
    50                  55                  60

Glu Asp Leu Leu Lys Glu His Tyr Val Asp Leu Lys Asp Arg Pro Phe
65                  70                  75                  80

Phe Ala Gly Leu Val Lys Tyr Met His Ser Gly Pro Val Val Ala Met
                85                  90                  95

Val Trp Glu Gly Leu Asn Val Val Lys Thr Gly Arg Val Met Leu Gly
            100                 105                 110

Glu Thr Asn Pro Ala Asp Ser Lys Pro Gly Thr Ile Arg Gly Asp Phe
        115                 120                 125

Cys Ile Gln Val Gly Arg Asn Ile Ile His Gly Ser Asp Ser Val Glu
    130                 135                 140

Ser Ala Glu Lys Glu Ile Gly Leu Trp Phe His Pro Glu Glu Leu Val
145                 150                 155                 160

Asp Tyr Thr Ser Cys Ala Gln Asn Trp Ile Tyr Glu Ala Val Ala Leu
                165                 170                 175

Leu Ile Leu Ala Val
            180

<210> SEQ ID NO 35
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: His-MTD3-Nm23-MTD3 cDNA sequence

```
<220> FEATURE:
<221> NAME/KEY: CDS
<222> LOCATION: (1)..(570)

<400> SEQUENCE: 35 atg ggc agc agc cat cat cat cat cat cac agc agc ggc ctg gtg ccg       48
Met Gly Ser Ser His His His His His His Ser Ser Gly Leu Val Pro
1               5                   10                  15 cgc ggc agc cat atg gcg gtg gcg ctg ctg att ctg gcg gtg gcc aac       96
Arg Gly Ser His Met Ala Val Ala Leu Leu Ile Leu Ala Val Ala Asn
            20                  25                  30 tgt gag cgt acc ttc att gcg atc aaa cca gat ggg gtc cag cgg ggt      144
Cys Glu Arg Thr Phe Ile Ala Ile Lys Pro Asp Gly Val Gln Arg Gly
        35                  40                  45 ctt gtg gga gag att atc aag cgt ttt gag cag aaa gga ttc cgc ctt      192
Leu Val Gly Glu Ile Ile Lys Arg Phe Glu Gln Lys Gly Phe Arg Leu
    50                  55                  60 gtt ggt ctg aaa ttc atg caa gct tcc gaa gat ctt ctc aag gaa cac      240
Val Gly Leu Lys Phe Met Gln Ala Ser Glu Asp Leu Leu Lys Glu His
65                  70                  75                  80 tac gtt gac ctg aag gac cgt cca ttc ttt gcc ggc ctg gtg aaa tac      288
Tyr Val Asp Leu Lys Asp Arg Pro Phe Phe Ala Gly Leu Val Lys Tyr
                85                  90                  95 atg cac tca ggg ccg gta gtt gcc atg gtc tgg gag ggg ctg aat gtg      336
Met His Ser Gly Pro Val Val Ala Met Val Trp Glu Gly Leu Asn Val
            100                 105                 110 gtg aag acg ggc cga gtc atg ctc ggg gag acc aac cct gca gac tcc      384
Val Lys Thr Gly Arg Val Met Leu Gly Glu Thr Asn Pro Ala Asp Ser
        115                 120                 125 aag cct ggg acc atc cgt gga gac ttc tgc ata caa gtt ggc agg aac      432
Lys Pro Gly Thr Ile Arg Gly Asp Phe Cys Ile Gln Val Gly Arg Asn
    130                 135                 140 att ata cat ggc agt gat tct gtg gag agt gca gag aag gag atc ggc      480
Ile Ile His Gly Ser Asp Ser Val Glu Ser Ala Glu Lys Glu Ile Gly
145                 150                 155                 160 ttg tgg ttt cac cct gag gaa ctg gta gat tac acg agc tgt gct cag      528
Leu Trp Phe His Pro Glu Glu Leu Val Asp Tyr Thr Ser Cys Ala Gln
                165                 170                 175 aac tgg atc tat gaa gcg gtg gcg ctg ctg att ctg gcg gtg tga          573
Asn Trp Ile Tyr Glu Ala Val Ala Leu Leu Ile Leu Ala Val
                180                 185                 190

<210> SEQ ID NO 36
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gly Ser Ser His His His His His His Ser Ser Gly Leu Val Pro
1               5                   10                  15

Arg Gly Ser His Met Ala Val Ala Leu Leu Ile Leu Ala Val Ala Asn
            20                  25                  30

Cys Glu Arg Thr Phe Ile Ala Ile Lys Pro Asp Gly Val Gln Arg Gly
        35                  40                  45

Leu Val Gly Glu Ile Ile Lys Arg Phe Glu Gln Lys Gly Phe Arg Leu
    50                  55                  60

Val Gly Leu Lys Phe Met Gln Ala Ser Glu Asp Leu Leu Lys Glu His
65                  70                  75                  80
```

```
Tyr Val Asp Leu Lys Asp Arg Pro Phe Phe Ala Gly Leu Val Lys Tyr
                85                  90                  95

Met His Ser Gly Pro Val Val Ala Met Val Trp Glu Gly Leu Asn Val
            100                 105                 110

Val Lys Thr Gly Arg Val Met Leu Gly Glu Thr Asn Pro Ala Asp Ser
        115                 120                 125

Lys Pro Gly Thr Ile Arg Gly Asp Phe Cys Ile Gln Val Gly Arg Asn
    130                 135                 140

Ile Ile His Gly Ser Asp Ser Val Glu Ser Ala Glu Lys Glu Ile Gly
145                 150                 155                 160

Leu Trp Phe His Pro Glu Glu Leu Val Asp Tyr Thr Ser Cys Ala Gln
                165                 170                 175

Asn Trp Ile Tyr Glu Ala Val Ala Leu Leu Ile Leu Ala Val
                180                 185                 190

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-01

<400> SEQUENCE: 37

Ala Val Val Val Cys Ala Ile Val Leu Ala Ala Pro
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-02

<400> SEQUENCE: 38

Pro Leu Ala Leu Leu Val Leu Leu Leu Leu Gly Pro
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-03

<400> SEQUENCE: 39

Leu Leu Leu Ala Phe Ala Leu Leu Cys Leu Pro
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-04
```

-continued

```
<400> SEQUENCE: 40

Leu Leu Gly Ala Leu Ala Ala Val Leu Leu Ala Leu Ala
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-05

<400> SEQUENCE: 41

Pro Val Leu Leu Ala Leu Gly Val Gly Leu Val Leu Leu Gly Leu Ala
1               5                   10                  15

Val

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-06

<400> SEQUENCE: 42

Ala Ala Ala Ala Val Leu Leu Ala Ala
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-07

<400> SEQUENCE: 43

Ile Val Val Ala Val Val Val Ile
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-08

<400> SEQUENCE: 44

Ala Val Leu Ala Pro Val Val Ala Val
1               5

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: MTD JO-09

<400> SEQUENCE: 45

Leu Ala Val Cys Gly Leu Pro Val Val Ala Leu Leu Ala
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-10

<400> SEQUENCE: 46

Leu Gly Gly Ala Val Val Ala Ala Pro Val Ala Ala Ala Val Ala Pro
1               5                   10                  15

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-11

<400> SEQUENCE: 47

Leu Leu Leu Val Leu Ala Val Leu Leu Ala Val Leu Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-12

<400> SEQUENCE: 48

Leu Leu Ile Leu Leu Leu Leu Pro Leu Leu Ile Val
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-13

<400> SEQUENCE: 49

Leu Ala Ala Ala Ala Leu Ala Val Leu Pro Leu
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: MTD JO-14

<400> SEQUENCE: 50

Phe Leu Met Leu Leu Leu Pro Leu Leu Leu Leu Val Ala
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-15

<400> SEQUENCE: 51

Ala Ala Ala Ala Ala Ala Leu Gly Leu Ala Ala Ala Val Pro Ala
1               5                   10                  15

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-16

<400> SEQUENCE: 52

Leu Leu Leu Ala Ala Leu Leu Leu Ile Ala Phe Ala Ala Val
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-17

<400> SEQUENCE: 53

Ala Leu Ala Ala Val Val Leu Ile Pro Leu Gly Ile Ala Ala
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-18

<400> SEQUENCE: 54

Ala Ala Leu Ala Leu Gly Val Ala Ala Ala Pro Ala Ala Ala Pro Ala
1               5                   10                  15

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: MTD JO-19

<400> SEQUENCE: 55

Ala Ala Leu Ile Gly Ala Val Leu Ala Pro Val Val Ala Val
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-20

<400> SEQUENCE: 56

Ala Ala Gly Ile Ala Val Ala Ile Ala Ala Ile Val Pro Leu Ala
1               5                   10                  15

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-21

<400> SEQUENCE: 57

Ile Ala Val Ala Ile Ala Ala Ile Val Pro Leu Ala
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-22

<400> SEQUENCE: 58

Val Ala Met Ala Ala Ala Ala Val Leu Ala Ala Pro Ala Leu Ala
1               5                   10                  15

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-23

<400> SEQUENCE: 59

Leu Ala Val Leu Val Leu Leu Val Leu Leu Pro
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: MTD JO-24

<400> SEQUENCE: 60

Val Val Ala Val Leu Ala Pro Val Leu
1               5

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-25

<400> SEQUENCE: 61

Ala Ala Leu Leu Leu Pro Leu Leu Leu Leu Leu Pro
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-26

<400> SEQUENCE: 62

Pro Ala Ala Val Ala Ala Leu Leu Val Ile
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-27

<400> SEQUENCE: 63

Leu Leu Ile Ala Ala Leu Leu Pro
1               5

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-28

<400> SEQUENCE: 64

Ala Ala Val Val Leu Leu Pro Leu Ala Ala Ala Pro
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: MTD JO-29

<400> SEQUENCE: 65

Ala Ala Ala Ala Ala Ala Leu Leu Val Pro
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-30

<400> SEQUENCE: 66

Leu Pro Val Val Ala Leu Leu Ala
1               5

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-31

<400> SEQUENCE: 67

Ala Ala Ala Leu Ala Ala Pro Leu Ala Leu Pro
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-32

<400> SEQUENCE: 68

Leu Leu Leu Ala Leu Leu Leu Ala Ala
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-33

<400> SEQUENCE: 69

Ala Val Ala Val Val Ala Leu Leu
1               5

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: MTD JO-34

<400> SEQUENCE: 70

Leu Leu Leu Ile Ile Val Leu Leu Ile Val Pro
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-35

<400> SEQUENCE: 71

Leu Ala Leu Ala Ala Ala Val Val Pro
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-36

<400> SEQUENCE: 72

Pro Ala Ala Leu Ala Leu Leu Leu Val Ala
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-37

<400> SEQUENCE: 73

Ile Val Ala Leu Leu Leu Val Pro Leu Val Leu Ala Ile Ala Ala Val
1               5                   10                  15

Leu

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-38

<400> SEQUENCE: 74

Ile Val Ala Leu Leu Leu Val Pro
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic

```
              peptide
<220> FEATURE:
<223> OTHER INFORMATION: MTD JO-39

<400> SEQUENCE: 75

Pro Leu Val Leu Ala Ile Ala Ala Val Leu
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-40

<400> SEQUENCE: 76

Pro Leu Val Leu Ala Ala Leu Val Ala
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-41

<400> SEQUENCE: 77

Ala Ala Ala Leu Leu Ala Val Ala
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-42

<400> SEQUENCE: 78

Pro Leu Leu Leu Leu Ala Leu Ala
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-43

<400> SEQUENCE: 79

Ala Leu Ala Leu Val Val Ala
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: MTD JO-44

<400> SEQUENCE: 80

Val Ala Ala Val Val Ala Ala
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-45

<400> SEQUENCE: 81

Pro Leu Leu Pro Leu Leu Leu Leu Val
1               5

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-46

<400> SEQUENCE: 82

Val Val Leu Val Val Val Leu Pro Leu Ala Val Leu Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-47

<400> SEQUENCE: 83

Ala Ala Ala Val Pro Val Leu Val Ala Ala
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-48

<400> SEQUENCE: 84

Pro Ala Leu Leu Leu Leu Leu Leu Ala Ala Val Val
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic -continued

```
      peptide
<220> FEATURE:
<223> OTHER INFORMATION: MTD JO-49

<400> SEQUENCE: 85

Pro Leu Ala Ile Leu Leu Leu Leu Ile Ala Pro
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-50

<400> SEQUENCE: 86

Pro Leu Leu Ala Leu Val Leu Leu Ala Leu Ile Ala
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-51

<400> SEQUENCE: 87

Val Val Ala Val Leu Ala Leu Val Leu Ala Ala Leu
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-52

<400> SEQUENCE: 88

Pro Leu Leu Leu Leu Leu Pro Ala Leu
1               5

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-53

<400> SEQUENCE: 89

Leu Ala Ala Val Ala Ala Leu Ala Val Val Val Pro
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
                       peptide
<220> FEATURE:
<223> OTHER INFORMATION: MTD JO-54

<400> SEQUENCE: 90

Leu Leu Leu Leu Val Leu Ile Leu Pro Leu Ala Ala
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-55

<400> SEQUENCE: 91

Leu Ala Val Val Val Val Ala Ala Val
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-56

<400> SEQUENCE: 92

Val Leu Leu Ala Ala Ala Leu Ile Ala
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-57

<400> SEQUENCE: 93

Leu Ile Ala Leu Leu Ala Ala Pro Leu Ala
1               5                   10

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-58

<400> SEQUENCE: 94

Leu Ala Leu Leu Leu Leu Ala Ala
1               5

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
                      peptide
<220> FEATURE:
<223> OTHER INFORMATION: MTD JO-59

<400> SEQUENCE: 95

Leu Leu Ala Ala Ala Leu Leu Leu Leu Leu Ala
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-60

<400> SEQUENCE: 96

Val Ile Ile Ala Leu Ile Val Ile Val Ala
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-61

<400> SEQUENCE: 97

Val Val Leu Val Val Ala Ala Val Leu Ala Leu
1               5                   10

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-62

<400> SEQUENCE: 98

Val Ala Val Ala Ile Ala Val Val Leu
1               5

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-63

<400> SEQUENCE: 99

Pro Leu Ile Val Val Val Ala Ala Ala Val Val Ala Val
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: MTD JO-64

<400> SEQUENCE: 100

Pro Leu Ala Val Ala Val Ala Val Ala Ala
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-65

<400> SEQUENCE: 101

Ala Ala Ile Ala Leu Val Ala Val Val Leu
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-66

<400> SEQUENCE: 102

Ala Ala Ala Leu Ala Ala Ile Ala Val Ile
1               5                   10

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-67

<400> SEQUENCE: 103

Ala Ala Ala Pro Ala Val Ala Ala
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-68

<400> SEQUENCE: 104

Leu Leu Leu Ala Ala Leu Pro
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<223> OTHER INFORMATION: MTD JO-69

<400> SEQUENCE: 105

Ala Leu Leu Ala Val Val Ala Ala
1               5

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-70

<400> SEQUENCE: 106

Ala Val Val Val Val Leu Pro Ile Leu Leu
1               5                   10

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-71

<400> SEQUENCE: 107

Ala Leu Ala Leu Leu Leu Leu Val Pro
1               5

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-72

<400> SEQUENCE: 108

Leu Val Val Leu Leu Ala Ala Leu Leu Val Leu
1               5                   10

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-73

<400> SEQUENCE: 109

Pro Val Leu Leu Leu Leu Ala Pro
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                            peptide
<220> FEATURE:
<223> OTHER INFORMATION: MTD JO-74

<400> SEQUENCE: 110

Ala Leu Ala Val Val Ala Ala Pro
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-75

<400> SEQUENCE: 111

Val Ile Val Ala Leu Leu Ala Val
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-78

<400> SEQUENCE: 112

Val Leu Leu Ala Val Ile Pro
1               5

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-79

<400> SEQUENCE: 113

Leu Ile Val Ala Ala Val Val Val Ala Val Leu Ile
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-80

<400> SEQUENCE: 114

Ala Val Val Val Ala Ala Pro
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                            peptide
<220> FEATURE:
<223> OTHER INFORMATION: MTD JO-81

<400> SEQUENCE: 115

Leu Ala Ala Val Leu Leu Leu Ile Pro
1               5

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-82

<400> SEQUENCE: 116

Leu Leu Leu Leu Leu Leu Ala Val Val Pro
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-83

<400> SEQUENCE: 117

Ala Val Ala Leu Val Ala Val Val Ala Val Ala
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-84

<400> SEQUENCE: 118

Leu Val Ala Ala Leu Leu Ala Val Leu
1               5

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-85

<400> SEQUENCE: 119

Leu Leu Ala Ala Ala Ala Ala Leu Leu Leu Ala
1               5                   10

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: MTD JO-86

<400> SEQUENCE: 120

Leu Ala Val Leu Ala Ala Ala Pro
1               5

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-87

<400> SEQUENCE: 121

Val Val Val Leu Leu Val Leu Leu Ala Leu Val Val Val
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-88

<400> SEQUENCE: 122

Val Val Ile Ala Val Val Pro
1               5

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-89

<400> SEQUENCE: 123

Leu Ala Ala Val Ala Ala Leu Ala Val Val
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-90

<400> SEQUENCE: 124

Val Leu Leu Val Leu Leu Ala Leu Val
1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: MTD JO-91

<400> SEQUENCE: 125

Pro Val Leu Val Pro Ala Val Pro
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-92

<400> SEQUENCE: 126

Pro Ala Leu Ala Leu Ala Leu Ala
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-93

<400> SEQUENCE: 127

Ala Ala Ala Ala Pro Ala Leu Ala
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-94

<400> SEQUENCE: 128

Ile Val Leu Pro Val Leu Ala Ala Pro
1               5

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-95

<400> SEQUENCE: 129

Leu Val Leu Leu Leu Leu Pro Leu Leu Ile
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: MTD JO-96

<400> SEQUENCE: 130

Leu Ala Ala Val Ala Pro Ala Leu Ala Val Val
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-97

<400> SEQUENCE: 131

Ile Leu Val Leu Val Leu Pro Ile
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-98

<400> SEQUENCE: 132

Ile Leu Leu Pro Leu Leu Leu Leu Pro
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-99

<400> SEQUENCE: 133

Ile Ala Pro Ala Val Val Ala Ala Leu Pro
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-100

<400> SEQUENCE: 134

Leu Leu Leu Val Ala Val Val Pro Leu Leu Val Pro
1               5                   10

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: MTD JO-101

<400> SEQUENCE: 135

Leu Ile Leu Leu Leu Leu Pro Ile Ile
1               5

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-102

<400> SEQUENCE: 136

Ala Val Leu Ala Ala Pro Ala Val Leu Val
1               5                   10

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-103

<400> SEQUENCE: 137

Leu Ala Leu Pro Val Leu Leu Leu Ala
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-104

<400> SEQUENCE: 138

Leu Ala Leu Ala Leu Leu Leu
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-105

<400> SEQUENCE: 139

Val Ala Val Pro Leu Leu Val Val Ala
1               5

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                                    peptide
<220> FEATURE:
<223> OTHER INFORMATION: MTD JO-106

<400> SEQUENCE: 140

Ala Val Ala Val Ala Pro Val Ala Ala Ala
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-107

<400> SEQUENCE: 141

Ala Ala Ala Val Val Ala Ala Val Pro Ala Ala
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-108

<400> SEQUENCE: 142

Ala Leu Leu Ala Ala Leu Leu Ala Pro
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-109

<400> SEQUENCE: 143

Leu Leu Ala Leu Leu Val Pro
1               5

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-110

<400> SEQUENCE: 144

Ala Leu Leu Ala Ala Leu Leu Ala Leu Leu Ala Leu Leu Val
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<223> OTHER INFORMATION: MTD JO-111

<400> SEQUENCE: 145

Ala Ala Ala Leu Pro Leu Leu Val Leu Leu Pro
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-112

<400> SEQUENCE: 146

Ala Ala Ala Val Pro Ala Ala Leu Ala Pro
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-113

<400> SEQUENCE: 147

Ala Ala Leu Ala Val Ala Ala Leu Ala Ala
1               5                   10

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-114

<400> SEQUENCE: 148

Ala Val Leu Ala Ala Ala Val Pro
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-115

<400> SEQUENCE: 149

Val Ala Ala Leu Pro Ala Pro Ala
1               5

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
```

-continued

```
       peptide
<220> FEATURE:
<223> OTHER INFORMATION: MTD JO-116

<400> SEQUENCE: 150

Ala Leu Ala Leu Ala Val Pro Ala Val Leu Pro
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<223> OTHER INFORMATION: MTD JO-117

<400> SEQUENCE: 151

Ala Ala Leu Leu Pro Ala Ala Val Ala Val Pro
1               5                   10

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<223> OTHER INFORMATION: MTD JO-118

<400> SEQUENCE: 152

Ala Val Val Val Ala Leu Ala Pro
1               5

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<223> OTHER INFORMATION: MTD JO-119

<400> SEQUENCE: 153

Ala Ala Ala Val Ala Leu Pro Ala Ala Ala Ala Leu Leu Ala
1               5                   10

<210> SEQ ID NO 154
<211> LENGTH: 13
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<223> OTHER INFORMATION: MTD JO-120

<400> SEQUENCE: 154

Ala Val Val Leu Pro Leu Ala Leu Val Ala Val Ala Pro
1               5                   10

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: MTD JO-121

<400> SEQUENCE: 155

Leu Val Ala Leu Pro Leu Leu Pro
1               5

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-122

<400> SEQUENCE: 156

Val Val Val Pro Leu Leu Leu Ile Val Pro
1               5                   10

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-123

<400> SEQUENCE: 157

Leu Ala Val Val Leu Ala Val Pro
1               5

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-124

<400> SEQUENCE: 158

Leu Leu Ala Val Pro Ile Leu Leu Val Pro
1               5                   10

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-125

<400> SEQUENCE: 159

Leu Val Ala Leu Val Leu Leu Pro
1               5

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic -continued

```
      peptide
<220> FEATURE:
<223> OTHER INFORMATION: MTD JO-126

<400> SEQUENCE: 160

Leu Val Leu Leu Leu Ala Val Leu Leu Ala Val Leu Pro
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-127

<400> SEQUENCE: 161

Leu Leu Ala Pro Val Val Ala Leu Val Ile Leu Pro
1               5                   10

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-128

<400> SEQUENCE: 162

Val Leu Ala Val Leu Ala Val Pro Val Leu Leu Leu Pro
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-129

<400> SEQUENCE: 163

Val Val Ile Ala Val Val Pro Val Val Val
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-130

<400> SEQUENCE: 164

Leu Leu Val Leu Leu Ala Leu Val Val Val Pro
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                       peptide
<220> FEATURE:
<223> OTHER INFORMATION: MTD JO-131

<400> SEQUENCE: 165

Val Leu Leu Ala Leu Pro Val Val Ala Ala Pro
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-132

<400> SEQUENCE: 166

Ala Val Val Val Pro Ala Ile Val Leu Ala Ala Pro
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-133

<400> SEQUENCE: 167

Ala Val Leu Val Pro Ala Ala Ala Leu Val Pro
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-134

<400> SEQUENCE: 168

Val Val Ala Ala Leu Pro Leu Val Leu Pro
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-135

<400> SEQUENCE: 169

Ala Ala Val Ala Leu Pro Ala Ala Ala Pro
1               5                   10

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: MTD JO-136

<400> SEQUENCE: 170

Leu Ile Ala Leu Pro Leu Leu Pro
1               5

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: MTD JO-137

<400> SEQUENCE: 171

Leu Leu Ala Leu Pro Leu Val Leu Val Leu Ala Leu Pro
1               5                   10

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: MTD JO-138

<400> SEQUENCE: 172

Ile Val Pro Leu Leu Leu Ala Ala Pro
1               5

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: MTD JO-139

<400> SEQUENCE: 173

Leu Leu Leu Ala Pro Leu Leu Leu Ala Pro
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: MTD JO-140

<400> SEQUENCE: 174

Leu Ala Ala Leu Pro Val Ala Ala Val Pro
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                       peptide
<220> FEATURE:
<223> OTHER INFORMATION: MTD JO-141

<400> SEQUENCE: 175

Ala Leu Ala Val Ile Val Leu Val Leu Leu
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-142

<400> SEQUENCE: 176

Leu Ala Leu Leu Leu Pro Ala Ala Leu Ile
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-143

<400> SEQUENCE: 177

Ala Leu Leu Pro Leu Leu Ala Val Val Leu Pro
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-144

<400> SEQUENCE: 178

Ala Ile Ala Val Pro Val Leu Ala Ala Pro
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-145

<400> SEQUENCE: 179

Ala Ala Ala Pro Val Leu Leu Leu Leu Leu
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                       peptide
<220> FEATURE:
<223> OTHER INFORMATION: MTD JO-146

<400> SEQUENCE: 180

Ala Ala Ala Val Ala Val Leu Ala Leu Ala Pro
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE
<223> OTHER INFORMATION: MTD JO-147

<400> SEQUENCE: 181

Ala Ala Leu Ala Ala Leu Val Val Ala Ala Pro
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-148

<400> SEQUENCE: 182

Ala Ala Leu Ala Ala Val Pro Leu Ala Leu Ala Pro
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-149

<400> SEQUENCE: 183

Ala Leu Ala Val Ala Ala Pro Ala Leu Ala Leu Leu Pro
1               5                   10

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-150

<400> SEQUENCE: 184

Ala Ala Leu Pro Ala Ala Ala Pro
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: MTD JO-151

<400> SEQUENCE: 185

Ala Ala Ala Pro Val Ala Ala Val Pro
1               5

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-152

<400> SEQUENCE: 186

Leu Leu Ala Val Leu Leu Ala Leu Leu Pro
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-153

<400> SEQUENCE: 187

Val Leu Ala Leu Leu Val Ala Val Val Pro
1               5                   10

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-154

<400> SEQUENCE: 188

Ala Leu Val Val Pro Ala Ala Val Pro
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-155

<400> SEQUENCE: 189

Ala Val Val Leu Pro Leu Leu Leu Pro
1               5

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic

```
                          peptide
<220> FEATURE:
<223> OTHER INFORMATION: MTD JO-156

<400> SEQUENCE: 190

Ala Val Ile Pro Val Ala Val Leu Val Pro
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-157

<400> SEQUENCE: 191

Ala Ala Ala Val Pro Ala Ala Val Leu Ala Pro
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-158

<400> SEQUENCE: 192

Val Ala Val Pro Val Val Leu Ala Ile Leu Pro
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-159

<400> SEQUENCE: 193

Ile Ala Ile Ala Ala Ile Pro Ala Ile Leu Ala Leu
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-160

<400> SEQUENCE: 194

Ala Leu Ile Ala Pro Ala Leu Ala Ala Pro
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: MTD JO-161

<400> SEQUENCE: 195

Ala Ala Ile Ala Leu Val Ala Pro Ala Leu
1               5                   10

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-162

<400> SEQUENCE: 196

Leu Ala Pro Ala Val Ala Ala Ala Pro
1               5

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-163

<400> SEQUENCE: 197

Val Ala Ile Ile Val Pro Ala Val Val Ala Ile Ala Leu Ile Ile
1               5                   10                  15

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-164

<400> SEQUENCE: 198

Ala Val Val Ala Ile Ala Leu Ile Ile
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-165

<400> SEQUENCE: 199

Leu Ala Ala Val Pro Ala Ala Ala Pro
1               5

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<223> OTHER INFORMATION: MTD JO-166

<400> SEQUENCE: 200

Ala Val Ala Ala Leu Pro Leu Ala Ala Pro
 1               5                  10

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-167

<400> SEQUENCE: 201

Leu Ala Ala Pro Ala Ala Ala Ala Pro
 1               5

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-168

<400> SEQUENCE: 202

Leu Ala Ala Val Val Pro Val Ala Ala Ala Val Pro
 1               5                  10

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-169

<400> SEQUENCE: 203

Val Ala Ala Pro Ala Ala Ala Ala Pro
 1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-170

<400> SEQUENCE: 204

Ala Val Pro Val Pro Val Pro Leu
 1               5

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<223> OTHER INFORMATION: MTD JO-171

<400> SEQUENCE: 205

Leu Leu Ile Leu Pro Ile Val Leu Leu Pro
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-172

<400> SEQUENCE: 206

Ala Leu Ala Leu Pro Ala Leu Ala Ile Ala Pro
1               5                   10

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-173

<400> SEQUENCE: 207

Ala Val Ile Pro Ile Leu Ala Val Pro
1               5

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-174

<400> SEQUENCE: 208

Leu Ile Leu Leu Leu Pro Ala Val Ala Leu Pro
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-175

<400> SEQUENCE: 209

Ile Val Leu Ala Pro Val Pro Ala Ala Ala
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: MTD JO-176

<400> SEQUENCE: 210

Val Val Val Val Pro Val Leu Ala Ala Ala Ala
1               5                   10

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-177

<400> SEQUENCE: 211

Leu Val Ala Val Ala Ala Pro
1               5

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-178

<400> SEQUENCE: 212

Leu Val Leu Ala Ala Pro Ala Ala Leu Pro
1               5                   10

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-179

<400> SEQUENCE: 213

Leu Ile Ala Pro Ala Ala Ala Val Pro
1               5

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-180

<400> SEQUENCE: 214

Ala Leu Ala Ala Leu Pro Ile Ala Leu Pro
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                                peptide
<220> FEATURE:
<223> OTHER INFORMATION: MTD JO-181

<400> SEQUENCE: 215

Ala Val Leu Leu Leu Pro Ala Ala Ala
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-182

<400> SEQUENCE: 216

Ile Ala Leu Ala Leu Leu Pro Leu Leu
1               5

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-183

<400> SEQUENCE: 217

Val Leu Leu Ala Ala Ala Leu Ile Ala Pro
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-184

<400> SEQUENCE: 218

Ala Pro Ala Val Leu Pro Pro Val Val Val Ile
1               5                   10

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-185

<400> SEQUENCE: 219

Val Val Gly Leu Leu Val Ala Ala Leu
1               5

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: MTD JO-186

<400> SEQUENCE: 220

Ala Ala Ile Ala Ala Ala Ala Pro Leu Ala Ala
1               5                   10

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-187

<400> SEQUENCE: 221

Leu Leu Leu Ala Val Ala Pro
1               5

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-188

<400> SEQUENCE: 222

Leu Ile Leu Leu Leu Pro Leu Ala Ala Leu
1               5                   10

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-189

<400> SEQUENCE: 223

Ala Leu Leu Leu Leu Val Leu Ala
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-190

<400> SEQUENCE: 224

Leu Leu Leu Leu Leu Leu Pro Leu Ala
1               5

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: MTD JO-191

<400> SEQUENCE: 225

Leu Ala Leu Pro Leu Leu Leu Pro
1               5

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-192

<400> SEQUENCE: 226

Leu Leu Val Leu Pro Leu Leu Ile
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MTD JO-193

<400> SEQUENCE: 227

Leu Pro Leu Leu Pro Ala Ala Leu Val
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 228

His His His His His His
1               5
```